(12) United States Patent
Karavany et al.

(10) Patent No.: US 12,409,024 B2
(45) Date of Patent: Sep. 9, 2025

(54) FLOW MODIFICATION DEVICES IN BODY LUMENS

(71) Applicant: Nephronyx Ltd., Modiin (IL)

(72) Inventors: Sagy Karavany, Kibbutz Dvir (IL); Oren Moshe Rotman, Holon (IL); Eyal Teichman, Hod-Hasharon (IL); Tanhum Feld, Moshav Merhavya (IL); Menashe Yacoby, Shoham (IL); Boaz Nishri, Maagan Michael (IL)

(73) Assignee: Nephronyx Ltd., Modiin (IL)

( * ) Notice: Subject to any disclaimer, the term of this patent is extended or adjusted under 35 U.S.C. 154(b) by 1083 days.

(21) Appl. No.: 17/296,199

(22) PCT Filed: Nov. 25, 2019

(86) PCT No.: PCT/IB2019/060142
§ 371 (c)(1),
(2) Date: May 21, 2021

(87) PCT Pub. No.: WO2020/109979
PCT Pub. Date: Jun. 4, 2020

(65) Prior Publication Data
US 2022/0039938 A1    Feb. 10, 2022

Related U.S. Application Data

(60) Provisional application No. 62/873,755, filed on Jul. 12, 2019, provisional application No. 62/771,559, filed on Nov. 26, 2018.

(51) Int. Cl.
*A61F 2/06* (2013.01)
*A61F 2/966* (2013.01)
(Continued)

(52) U.S. Cl.
CPC ........... *A61F 2/06* (2013.01); *A61F 2/966* (2013.01); *A61M 60/135* (2021.01);
(Continued)

(58) Field of Classification Search
CPC ...... A61F 2/06; A61F 2/966; A61F 2002/068; A61F 2250/0039; A61F 2/07;
(Continued)

(56) References Cited

U.S. PATENT DOCUMENTS

| 5,134,890 A | 8/1992 | Abrams |
|---|---|---|
| 5,540,712 A | 7/1996 | Kleshinski et al. |

(Continued)

FOREIGN PATENT DOCUMENTS

| CN | 1174016 A | 2/1998 |
|---|---|---|
| CN | 101024098 A | 8/2007 |

(Continued)

OTHER PUBLICATIONS

International Search Report & Written Opinion dated Feb. 24, 2023 in Int'l PCT Patent Appl. Serial No. PCT/IB2022/06573 (0710).

(Continued)

*Primary Examiner* — Jerrah Edwards
*Assistant Examiner* — Jose H. Trevino, III
(74) *Attorney, Agent, or Firm* — Greenberg Traurig, LLP; Christopher C. Bolten; Albert K. Heng

(57) ABSTRACT

The devices and methods described herein include a body lumen fluid flow modulator including an upstream flow accelerator and a downstream flow decelerator. The fluid flow modulator preferably includes one or more openings that define a gap/entrainment region that provides a pathway through which additional fluid from a branch lumen(s) is entrained into the fluid stream flowing from the upstream flow accelerator to the downstream flow decelerator.

28 Claims, 52 Drawing Sheets

(51) Int. Cl.
*A61M 60/135* (2021.01)
*A61M 60/216* (2021.01)

(52) U.S. Cl.
CPC ..... *A61M 60/216* (2021.01); *A61F 2002/068* (2013.01); *A61F 2250/0039* (2013.01)

(58) Field of Classification Search
CPC .............. A61M 60/135; A61M 60/216; A61M 60/139; A61M 60/211; A61M 60/861
See application file for complete search history.

(56) References Cited

U.S. PATENT DOCUMENTS

| | | | |
|---|---|---|---|
| 6,120,534 | A | 9/2000 | Ruiz |
| 6,743,196 | B2 | 6/2004 | Barbut et al. |
| 7,048,702 | B2 | 5/2006 | Hui |
| 7,384,389 | B2 | 6/2008 | Anzellini |
| 9,204,958 | B2 | 12/2015 | LaDuca et al. |
| 9,764,113 | B2 | 9/2017 | Tuval et al. |
| 10,195,406 | B2 | 2/2019 | Karavany et al. |
| 11,324,619 | B1 | 5/2022 | Yacoby et al. |
| 11,607,532 | B2 | 3/2023 | Karavany et al. |
| 2001/0021872 | A1 | 9/2001 | Bailey et al. |
| 2004/0133260 | A1 | 7/2004 | Schwartz et al. |
| 2004/0143319 | A1 | 7/2004 | Schwartz et al. |
| 2004/0210236 | A1 | 10/2004 | Allers et al. |
| 2005/0043790 | A1 | 2/2005 | Seguin |
| 2005/0055082 | A1* | 3/2005 | Ben Muvhar ............. A61F 2/91 623/1.15 |
| 2005/0197687 | A1* | 9/2005 | Molaei .................. A61L 31/088 623/1.2 |
| 2005/0222674 | A1 | 10/2005 | Paine |
| 2006/0047334 | A1 | 3/2006 | Houston et al. |
| 2006/0064151 | A1 | 3/2006 | Guterman et al. |
| 2006/0106449 | A1 | 5/2006 | Ben Muvhar |
| 2006/0149360 | A1 | 7/2006 | Schwammenthal |
| 2007/0185565 | A1 | 8/2007 | Schwammenthal et al. |
| 2007/0293808 | A1 | 12/2007 | Williams et al. |
| 2009/0270965 | A1 | 10/2009 | Sinha et al. |
| 2010/0036307 | A1 | 2/2010 | Von Segesser |
| 2010/0063578 | A1 | 3/2010 | Ren et al. |
| 2010/0145433 | A1 | 6/2010 | Anukhin et al. |
| 2011/0015723 | A1 | 1/2011 | Batiste et al. |
| 2011/0282274 | A1 | 11/2011 | Fulton, III |
| 2011/0306916 | A1 | 12/2011 | Nitzan et al. |
| 2012/0095547 | A1 | 4/2012 | Chuter |
| 2012/0165928 | A1 | 6/2012 | Nitzan et al. |
| 2013/0338761 | A1 | 12/2013 | Plowiecki et al. |
| 2014/0350565 | A1 | 11/2014 | Yacoby et al. |
| 2014/0350658 | A1 | 11/2014 | Benary et al. |
| 2015/0039020 | A1 | 2/2015 | Cragg et al. |
| 2015/0045874 | A1* | 2/2015 | McMahon ............... D04C 3/12 623/1.22 |
| 2015/0073470 | A1 | 3/2015 | Andersen et al. |
| 2015/0119633 | A1* | 4/2015 | Haselby .................... A61F 2/86 600/16 |
| 2015/0164662 | A1 | 6/2015 | Tuval |
| 2015/0238315 | A1 | 8/2015 | Rabito et al. |
| 2015/0313603 | A1 | 11/2015 | Bodewadt et al. |
| 2016/0113764 | A1 | 4/2016 | Sheahan et al. |
| 2016/0128983 | A1 | 5/2016 | Djonov et al. |
| 2017/0112986 | A1 | 4/2017 | Heuring et al. |
| 2017/0128705 | A1 | 5/2017 | Forcucci et al. |
| 2017/0156845 | A1 | 6/2017 | Florescu |
| 2018/0014829 | A1 | 1/2018 | Tal et al. |
| 2018/0140448 | A1 | 5/2018 | Arbefeuille et al. |
| 2018/0280667 | A1 | 10/2018 | Keren |
| 2018/0344994 | A1* | 12/2018 | Karavany ............. A61M 60/33 |
| 2019/0008628 | A1 | 1/2019 | Eigler et al. |
| 2019/0069903 | A1 | 3/2019 | Deshmukh et al. |
| 2019/0167878 | A1 | 6/2019 | Rowe |
| 2019/0183629 | A1* | 6/2019 | Karavany ............... A61F 2/966 |
| 2019/0239998 | A1* | 8/2019 | Tuval ........................ A61F 2/06 |
| 2019/0298509 | A1 | 10/2019 | Sohn |
| 2020/0138560 | A1 | 5/2020 | Karavany et al. |
| 2021/0236727 | A1 | 8/2021 | Levin et al. |
| 2021/0244381 | A1 | 8/2021 | Sweeney et al. |
| 2021/0290356 | A1* | 9/2021 | Brinkmann ............... A61F 2/07 |
| 2022/0287831 | A1 | 9/2022 | Thornton |

FOREIGN PATENT DOCUMENTS

| | | | |
|---|---|---|---|
| CN | 102448406 | A | 5/2012 |
| CN | 102462565 | A | 5/2012 |
| CN | 105899141 | A | 8/2016 |
| CN | 107898532 | A | 4/2018 |
| CN | 110891522 | A | 3/2020 |
| WO | WO-0197717 | A1 | 12/2001 |
| WO | WO-2005048871 | A2 | 6/2005 |
| WO | WO-2013183060 | A2 | 12/2013 |
| WO | WO-2014141284 | A2 | 9/2014 |
| WO | WO-2015177793 | A2 | 11/2015 |
| WO | WO-2016128983 | A1 | 8/2016 |
| WO | WO-2016185473 | A1 | 11/2016 |
| WO | WO-2017115267 | A1 | 7/2017 |
| WO | WO-2018029688 | A1 | 2/2018 |
| WO | WO-2018061002 | A1 | 4/2018 |
| WO | WO-2018220589 | A1 | 12/2018 |
| WO | WO-2019097424 | A2 | 5/2019 |
| WO | WO-2019186538 | A1 | 10/2019 |
| WO | WO-2020109979 | A1 | 6/2020 |
| WO | WO-2021226014 | A2 | 11/2021 |
| WO | WO-2021240411 | A1 | 12/2021 |

OTHER PUBLICATIONS

International Search Report & Written Opinion dated Mar. 18, 2024 in Int'l PCT Patent Appl. Serial No. PCT/IB2023/061404 (0810).
International Search Report & Written Opinion dated Aug. 18, 2021 in Int'l PCT Patent Appl. Serial No. PCT/IB2021/054612 (0610).
International Search Report & Written Opinion dated Feb. 13, 2020 in Int'l PCT Patent Appl. Serial No. PCT/IB2019/060142 (0510).
Int'l Search Report & Written Opinion dated Sep. 17, 2018 in Int'l PCT Patent Appl. Serial No. PCT/IB2018/053925 (0410).
Supplementary EP Search Report and Opinion dated May 3, 2024 in EP Patent Appl. No. 21811863.6 (0630).
U.S. Appl. No. 15/995,101 / U.S. Pat. No. 10,195,406, filed May 31, 2018 / Feb. 5, 2019.
U.S. Appl. No. 16/617,479, filed Nov. 26, 2019.

* cited by examiner

Deployment

Retrieval

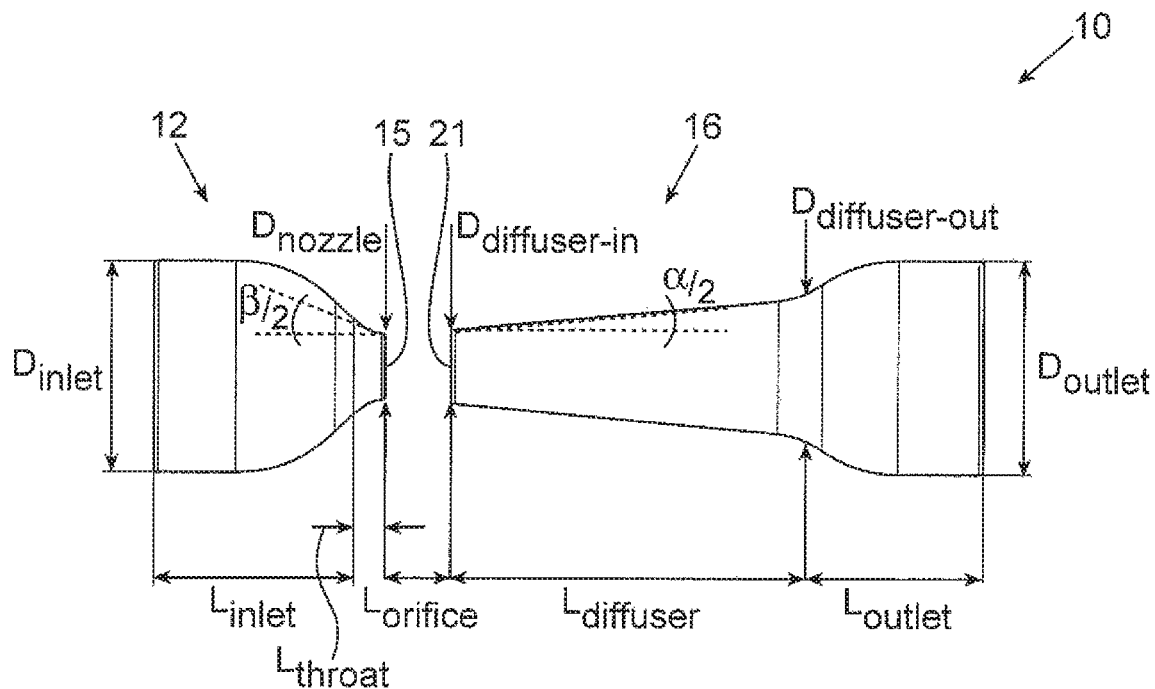
FIG. 51A
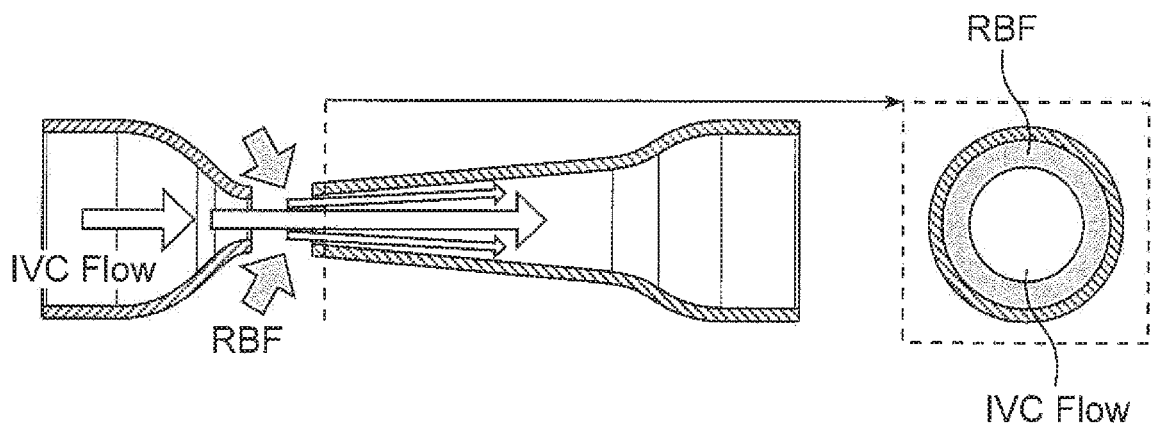
FIG. 51B
FIG. 51C

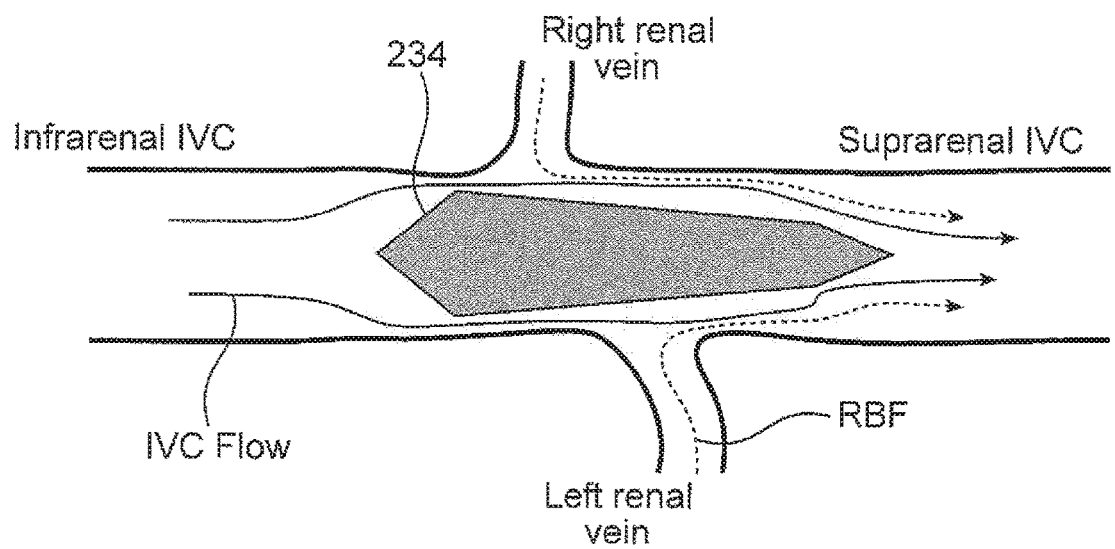
FIG. 57A
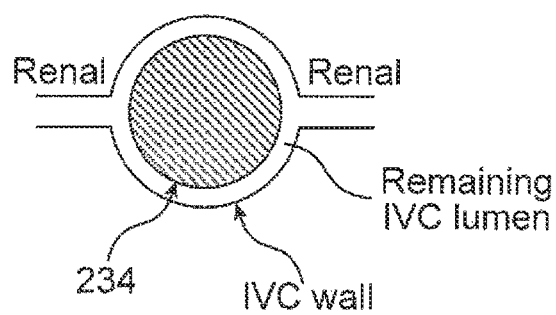 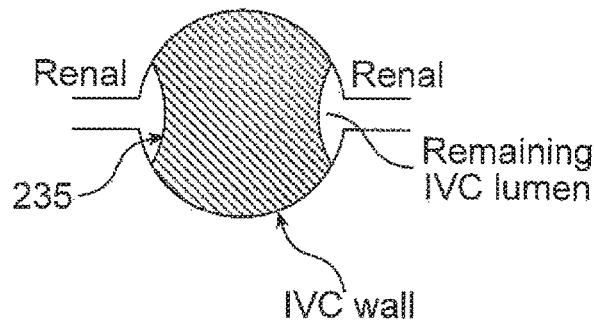
FIG. 57B  FIG. 57C

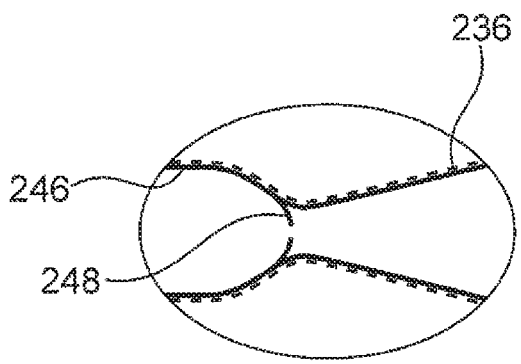 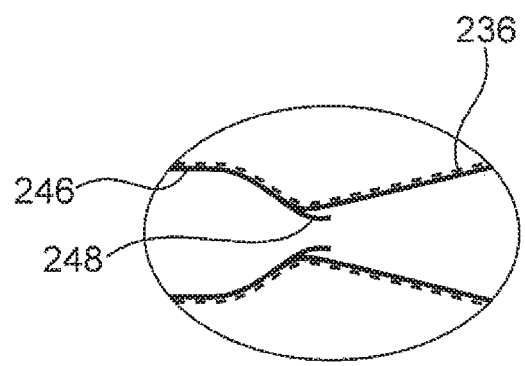
FIG. 61A  FIG. 61B
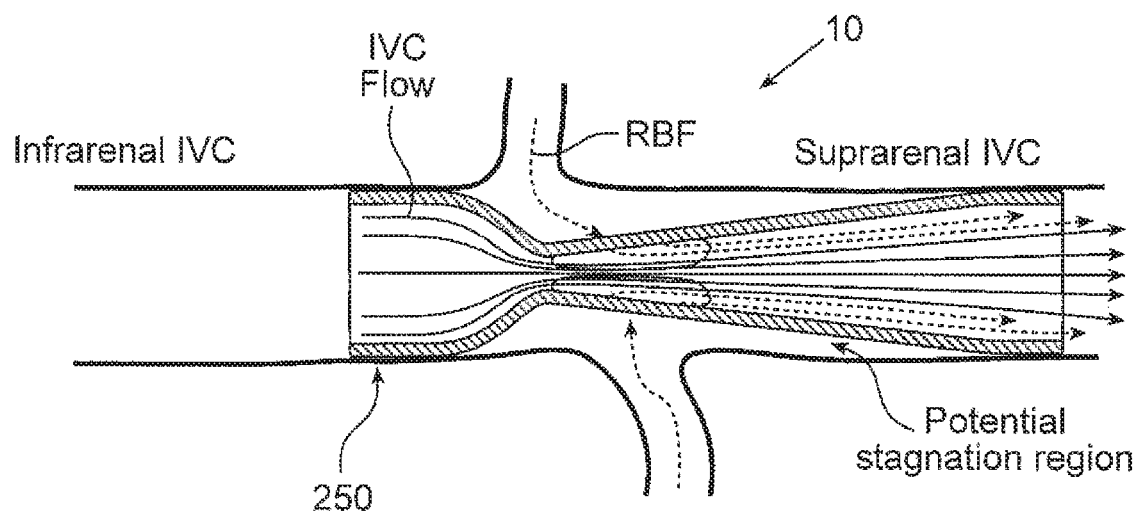
FIG. 62A
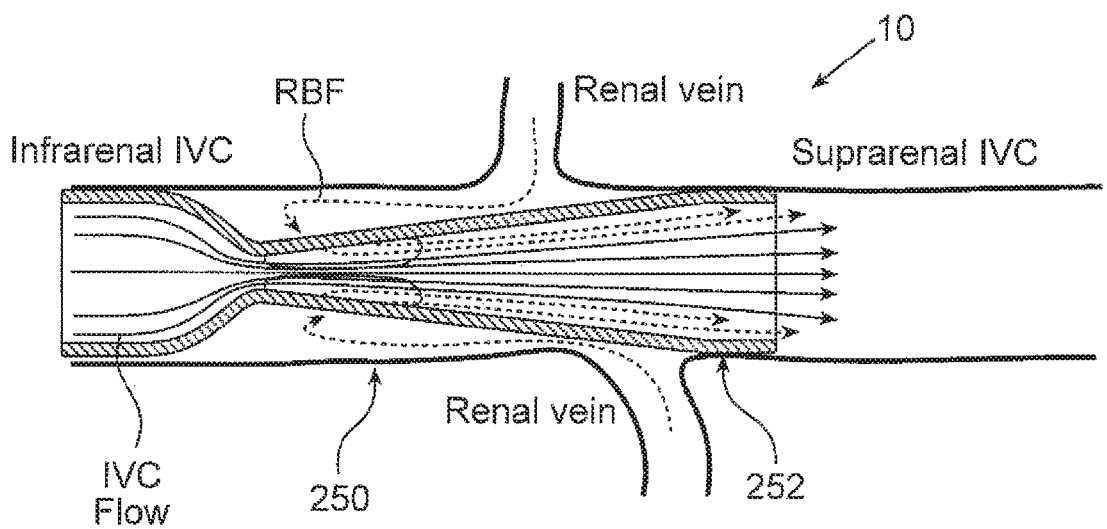
FIG. 62B

FLOW MODIFICATION DEVICES IN BODY LUMENS

CROSS-REFERENCE TO RELATED APPLICATIONS

This application is a national phase application under 35 U.S.C. § 371 of PCT/IB2019/060142, filed Nov. 25, 2019, which claims the benefit of priority of U.S. Provisional Application Ser. No. 62/873,755, filed Jul. 12, 2019, and U.S. Provisional Application Ser. No. 62/771,559, filed Nov. 26, 2018, the entire contents of each of which are incorporated herein by reference. This application is related to U.S. patent application Ser. No. 15/995,101, filed May 31, 2018, now U.S. Pat. No. 10,195,406, and PCT International Application No. PCT/IB2018/053925, filed May 31, 2018, published as WO 2018/220589, each of which claims the benefit of priority of U.S. Provisional Application Ser. No. 62/537,067, filed Jul. 26, 2017, and U.S. Provisional Application Ser. No. 62/514,020, filed Jun. 2, 2017, the entire contents of each of which are incorporated herein by reference.

FIELD OF THE INVENTION

The present invention relates generally to devices and methods for altering flow in body lumens, such as devices and methods for creating pressure differences and/or entrainment of fluid at lumens that branch off from other lumens for enhancing or modifying fluid flow to treat different disorders or diseases.

BACKGROUND OF THE INVENTION

Heart failure is the physiological state in which cardiac output is insufficient to meet the needs of the body and the lungs. Patients suffering from any of a number of forms of heart failure are prone to increased fluid in the body. Congestive heart failure (CHF) occurs when cardiac output is relatively low and the body becomes congested with fluid. There are many possible underlying causes of CHF, including myocardial infarction, coronary artery disease, valvular disease, and myocarditis. Chronic heart failure is associated with neurohormonal activation and alterations in autonomic control. Although these compensatory neurohormonal mechanisms provide valuable support for the heart under normal physiological circumstances, they also have a fundamental role in the development and subsequent progression of CHF. For example, one of the body's main compensatory mechanisms for reduced blood flow in CHF is to increase the amount of salt and water retained by the kidneys. Retaining salt and water, instead of excreting it into the urine, increases the volume of blood in the bloodstream and helps to maintain blood pressure. However, the larger volume of blood also stretches the heart muscle, enlarging the heart chambers, particularly the ventricles. At a certain amount of stretching, the heart's contractions become weakened, and the heart failure worsens. Another compensatory mechanism is vasoconstriction of the arterial system. This mechanism, like salt and water retention, raises the blood pressure to help maintain adequate perfusion.

Glomerular filtration rate (GFR), the rate at which the kidney filters blood, is commonly used to quantify kidney function and, consequently, the extent of kidney disease in a patient. Individuals with normal kidney function exhibit a GFR of at least 90 mL/min with no evidence of kidney damage. The progression of kidney disease is indicated by declining GFR, wherein a GFR below 15 mL/min generally indicates that the patient has end stage renal disease (ESRD), which is the complete failure of the kidney to remove wastes or concentrate urine.

In addition to increases in total body salt and water, it has also been found that altered capacitance of the splanchnic venous vessels change the blood volume distribution. Decreased venous capacitance can lead to shifts of fluid from the venous reservoir into the effective circulatory volume/splanchnic circulation, thus increasing filling pressures. This could result in clinical heart congestion.

Cardiovascular problems, such as but not limited to, inadequate blood flow or chronic hypertension, may lead to fluid retention in the kidneys, chronic kidney disease, lowered GFR, renal failure or even ESRD. For example, hypertension is considered the second most prevalent cause for kidney failure (after diabetes). It has been estimated that hypertension causes nephrotic damage and lowers GFR.

Transjugular intrahepatic portosystemic shunt (TIPS or TIPSS) is an artificial channel within the liver that establishes communication between the inflow portal vein and the outflow hepatic vein. Generally, under imaging guidance, a small metal stent is placed to keep the channel open and allow the channel to bring blood draining from the bowel back to the heart while avoiding the liver. TIPS may be used to treat conditions such as portal hypertension (often due to liver cirrhosis) which frequently leads to intestinal bleeding, life-threatening esophageal bleeding (esophageal varices), and the buildup of fluid within the abdomen (ascites), and has shown promise for treating hepatorenal syndrome. A drawback of TIPS is that blood meant to be filtered by the liver bypasses the liver via the artificial channel, which may cause complications.

Therefore, it would be desirable to provide apparatus and methods to improve blood flow to prevent disease, improve body functionality, and/or treat conditions that would benefit from modified body fluid flow. For example, it would be desirable to treat heart failure, treat hypertension, prevent kidney disease, improve kidney functionality, restore normal values of splanchnic circulation, improve liver functionality, enhance or replace TIPS, and/or prevent blood clots from flowing through vasculature to sensitive portions of the body, such as the brain, in order to prevent strokes.

SUMMARY OF THE INVENTION

The present invention seeks to provide devices and methods for altering flow in body lumens, as is described more in detail hereinbelow. For example, devices and methods are provided for creating pressure differences and/or fluid entrainment at lumens that branch off from other lumens for enhancing or modifying fluid flow to treat different disorders or diseases. For positioning, the device may be acutely or chronicly implanted within the body lumen.

The devices and methods of the present invention have many applications. For example, the device may be used to reduce pressure and improve flow, thereby improving flow in stenotic body lumens. It also may be used in the aortic arch to reduce peak systolic pressure in the brain or divert emboli to other portions of the body (e.g., the legs) and thereby reduce the risk of stroke. The device further may be installed in a bifurcation (e.g., in the brachiocephalic vessels) to reduce peak pressure gradients or to divert emboli with very little energy loss.

The devices and methods of the present invention have particular application in treating blood flow to and from the kidneys. In accordance with one embodiment, the device is configured to be installed near one of the renal arteries or in the inferior vena cava near the branch off to the renal veins or in one of the renal veins.

When installed in the inferior vena cava or in the renal vein, the device can create (due to the Bernoulli effect or other factors) a region in the inferior vena cava or in the renal vein which has increased blood velocity and reduced pressure. In this manner, blood may be drawn from the kidneys to the renal veins and then to the inferior vena cava, thereby improving kidney functionality and reducing necrotic damage to the kidneys.

When installed in or near the renal vein, the devices of the present invention may improve renal function by improving net filtration pressure, which is glomerular capillary blood pressure—(plasma-colloid osmotic pressure+Bowman's capsule hydrostatic pressure), e.g., 55 mm Hg—(30 mm Hg+15 mm Hg)=10 mm Hg. The devices and methods of the present invention thus provide an improvement over existing therapies, such as diuretics (although the invention can be used in addition to diuretics), angiotensin-converting enzyme inhibitors (ACEIs), and angiotensin receptor blockers (ARBs), which can have deleterious effects on kidney function. When used in conjunction with current modes of treatment such as diuretics, the devices and methods of the present invention are expected to improve the response for diuretics and reduce the dosage needed to obtain therapeutic benefit of such previously known therapies, without the disadvantages of these existing therapies.

The devices and methods of the present invention may be used to divert flow from the kidneys to the inferior vena cava with little energy loss. For example, with a small energy loss due to pressure drop and other fluid factors, a significantly greater increase in blood flow may be achieved. This diversion of flow from the kidneys with little energy loss to increase blood flow is expected to treat conditions such as heart failure and/or hypertension.

It is noted that there is a significant difference between use of an upstream nozzle with no downstream flow decelerator, such as a diffuser. If only an upstream nozzle is placed in the flow path, there is significant energy loss downstream of the nozzle due to the sudden expansion of flow. However, by using a downstream flow decelerator, such as a diffuser, the energy loss is significantly reduced. This leads to another advantage: since the energy loss is significantly reduced, the additional flow that flows into the gap is efficiently added to the flow from the upstream flow accelerator.

In addition, the present invention is expected to provide optimal structure for an upstream flow accelerator when used together with a downstream flow decelerator. For example, the distance between the outlet of the upstream flow accelerator and the inlet of the downstream flow decelerator should be less than a predetermined length to reduce pressure at the gap between the outlet and the inlet.

When installed in the renal artery, the device can reduce pressure applied to the kidneys. Without being limited by any theory, high blood pressure can cause damage to the blood vessels and filters in the kidney, making removal of waste from the body difficult. By reducing the pressure in the renal artery, the filtration rate improves. Although there may be a reduction in the perfusion pressure, the filtration rate will increase because the overall kidney function is more efficient.

It is noted that the fluid flow modulator of the present invention may modulate fluid flow without any input from an external energy source, such as a fan, motor, and the like and without any moving parts. The structure of the device of the invention transfers energy from one lumen flow to another different lumen flow with minimal flow energy losses.

In accordance with one aspect of the present invention, a device is provided for altering fluid flow through a body lumen (e.g., the inferior vena cava) that is coupled to a branch lumen(s) (e.g., a renal vein(s), a hepatic vein(s)). The device includes a flow modulator configured to be positioned within the body lumen. The flow modulator preferably has an upstream component and a downstream component and defines a gap. The flow modulator may be formed as a single unit (e.g., from a single frame) or multiple units. The upstream component has an inlet, an outlet, and a cross-sectional flow area that preferably converges from the inlet towards the outlet. The downstream component has an entry, an exit, and a cross-sectional flow area that preferably diverges from the entry towards the exit. The gap defines a pathway that communicates with the branch lumen and is preferably between the inlet of the upstream component and the exit of the downstream component. The upstream component and the downstream component each preferably define a plurality of cells, a first plurality and a second plurality, respectively, and the first plurality of cells may have a more flexible structure than the second plurality of cells. This may be achieved, for example, by having the average void space area of the second plurality of cells be less than the average void space area of the first plurality of cells. Preferably, the void space is the area of the cell defined by the struts of the frame. For example, the struts may define close-looped shapes such as ellipses or diamonds or a combination thereof. The gap, which may be formed of one or more openings in an entrainment region, may be devoid of cells, or may include a plurality of radially spaced openings disposed on the downstream component. The plurality of radially spaced openings may be relatively parallel or angled relative to the longitudinal axis of the flow modulator. The flow modulator preferably accelerates a fluid stream passing through the upstream component towards the downstream component to generate a low pressure region in the vicinity of the gap and to entrain additional fluid into the fluid stream as the fluid stream passes into the entry of the downstream component. An inner core may be advanced into the flow modulator to further entrain the fluid by increasing or decreasing the effective cross sectional area of the nozzle and/or the diffuser.

The outlet of the upstream component is preferably spaced apart from the entry of the downstream component a suitable distance for increasing flow within the branch lumen(s) while minimizing pressure loss. For example, the distance from the outlet to the entry may be less than 15 mm.

In accordance with one aspect, the downstream component has two diverging portions, each portion having a different average angle of divergence. For example, the second diverging portion may have a greater average angle of divergence than the first diverging portion. In one embodiment, the second diverging portion defines a third plurality of cells having a more flexible structure than the second plurality of cells. The second plurality of cells preferably is positioned between the first and third pluralities of cells. In this manner, the intermediate region of the flow modulator is structured to be more rigid than the more flexible inner and outer regions. The first and third plurality of cells may have substantially identical flexibility.

In accordance with one aspect, the cross-sectional flow area at the outlet of the upstream component is less than the cross-sectional flow area at the entry of the downstream component. Additionally, the upstream component may include a constricted section to permit coupling to a delivery device, which may remain coupled to the delivery device throughout an acute treatment or may be detachable from the delivery device for a chronic treatment. The downstream device may include an atraumatic end to prevent vessel damage, give distal end integrity, and prevent flare out during device crimping. The outlet of the upstream component may be positioned downstream from where the branch lumen first intersects with the body lumen. The gap may begin downstream from where the branch lumen first intersects with the body lumen. The upstream component and the downstream component may share a common, collinear flow axis with the body lumen's flow axis. The outlet of the upstream component may be positioned downstream from the entry of the downstream component.

In one example, the upstream component is coupled to the downstream component via a fluid flow structure that defines the gap. The upstream component, the downstream component, and the fluid flow structure may be formed from a single frame. The fluid flow structure may extend outward from the upstream component and from the downstream component such that the fluid flow structure contacts an inner wall of the body lumen. A junction between the fluid flow structure and the upstream component and/or the downstream component may have a curved shape such as an S-curve shape.

In accordance with one aspect, the downstream component's length is greater than the upstream component's length. The upstream component's average angle of convergence may be greater than the downstream component's average angle of divergence. The upstream component may include a nozzle that accelerates the fluid stream passing through the upstream component and the downstream component may include a diffuser that decelerates the fluid stream having the entrained additional fluid passing through the downstream component.

The flow modulator may be formed from a metal frame. The metal frame may be at least partially coated with a biocompatible material at the upstream component and at the downstream component. In one example, an uncoated portion of the metal frame between the upstream and downstream components defines the gap that allows fluid from the branch lumen(s) to entrain with the fluid stream flowing through the flow modulator.

In accordance with one aspect, a delivery device is for delivering the flow modulator to the body lumen is provided. The delivery device preferably has a sheath to hold the flow modulator in a contracted state and an inner assembly configure to slide within the sheath and push the flow modulator out of the sheath and into a deployed state in the body lumen.

In accordance with another aspect, a method for altering fluid flow through a body lumen coupled to a branch lumen is provided. The method may include positioning a flow modulator within a body lumen, the flow modulator including an upstream component and a downstream component and defining a gap, the upstream component being positioned in a first body lumen portion and having an inlet, an outlet, and a cross-sectional flow area that converges from the inlet towards the outlet, the downstream component being positioned in a second body lumen portion and having an entry, an exit, and a cross-sectional flow area that diverges from the entry towards the exit. The gap may be positioned where the branch lumen intersects with the body lumen and the outlet may be positioned downstream from where the branch lumen first intersects with the body lumen. The upstream component and the downstream component may each include a plurality of cells, and the downstream component's plurality of cells may be more rigid than the upstream component's plurality of cells. The method may include accelerating a fluid stream passing through the upstream component towards the downstream component to generate a low pressure region in the vicinity of the gap and to entrain additional fluid into the fluid stream as the fluid stream passes into the entry of the downstream component. The method may also include advancing an inner core into the flow modulator to further entrain the fluid.

Positioning the flow modulator within the body lumen may include positioning the upstream component in an inferior vena cava such that the inlet is upstream from a branch off to a renal vein(s) and the downstream component in the inferior vena cava such that the exit is downstream from the branch off to the renal vein(s), thereby drawing blood from the renal vein(s) to the inferior vena cava and improving kidney functionality. Drawing the blood from the renal vein(s) to the inferior vena cava to improve kidney functionality may further reduce excess fluid to treat heart failure.

Positioning the flow modulator within the body lumen may include positioning the upstream component in an inferior vena cava such that the inlet is upstream from a branch off to a hepatic vein(s) and the downstream component in the inferior vena cava such that the exit is downstream from the branch off to the hepatic vein(s), thereby inserting blood back to the inferior vena cava and improving splanchnic circulation. The flow modulator positioned within the inferior vena cava at the branch to the hepatic vein(s) is expected to improve liver functionality and/or may be used instead of, or in parallel to, a TIPS procedure.

The flow modulator may modulate fluid flow without any input from an external energy source. The flow modulator may modulate fluid flow without any moving parts. For instance, the gap may be a plurality of radially spaced openings angled relative to the longitudinal axis of the flow modulator, such as in a helical pattern, thus inducing a swirling fluid flow pattern.

There is thus provided in accordance with an embodiment of the present invention a system including a body-lumen fluid flow modulator including an upstream flow accelerator separated by a gap from a downstream flow decelerator, wherein the gap is a pathway to entrain additional fluid with fluid flowing from the upstream flow accelerator, to the downstream flow decelerator.

The gap may be located in a fluid flow structure that defines boundaries for the pathway to entrain the additional fluid to flow to the downstream flow decelerator. The upstream flow accelerator may have a flow cross-section that converges in a downstream direction. The downstream flow decelerator may have a flow cross-section that diverges in a downstream direction. The fluid flow structure may include one or more conduits that are not collinear with a direction of flow from the upstream flow accelerator to the downstream flow decelerator. The upstream flow accelerator and the downstream flow decelerator may share a common, collinear flow axis. The fluid flow structure may or may not connect the upstream flow accelerator to the downstream flow decelerator. The fluid flow structure may diverge outwards in a direction away from a central axis of the fluid flow structure. A junction between the fluid flow structure and at least one of the upstream flow accelerator and the downstream flow decelerator may be curved.

There is provided in accordance with an embodiment of the present invention a method for altering fluid flow through a body lumen including installing a fluid flow modulator in a body, the fluid flow modulator including an upstream flow accelerator separated by a gap from a downstream flow decelerator, the upstream flow accelerator being installed in a first body lumen portion, and the downstream flow decelerator being installed in a second body lumen portion, wherein when fluid flows from the upstream flow accelerator to the downstream flow decelerator, additional fluid is entrained into the gap and is added to the fluid flowing from the upstream flow accelerator to the downstream flow decelerator.

In one method, the fluid flow modulator is installed near renal arteries to improve renal function by reducing renal perfusion pressure.

In one method, the fluid flow modulator is installed near a bifurcation to divert emboli from the bifurcation.

In one method, the fluid flow modulator is installed in an aortic arch to reduce peak systolic pressure.

In one method, the fluid flow modulator is installed near hepatic veins to improve splanchnic circulation.

In accordance with another aspect of the present invention, another device for altering fluid flow through a body lumen coupled to a branch lumen is provided. The device includes a flow modulator having an upstream component and a downstream component and defining a gap. The upstream component has an inlet, an outlet, and a cross-sectional flow area that converges from the inlet towards the outlet, and defines a first plurality of cells. The downstream component has an entry, an exit, and a cross-sectional flow area that diverges from the entry towards the exit, and defines a second plurality of cells having a less flexible structure than the first plurality of cells, wherein the gap defines a pathway that communicates with the branch lumen. The gap may be positioned between the inlet of the upstream component and the exit of the downstream component. The upstream component and the downstream component may be at least partially coated with a biocompatible material, thereby exposing the gap. Moreover, the flow modulator is designed to accelerate a fluid stream passing through the upstream component towards the downstream component to generate a low pressure region in the vicinity of the gap and to entrain additional fluid into the fluid stream as the fluid stream passes into the entry of the downstream component.

In addition, the downstream component may include a first diverging portion and a second diverging portion, such that the first diverging portion is upstream from the second diverging portion. The second diverging portion's average angle of divergence may be greater than the first diverging portion's average angle of divergence. Further, the second diverging portion may define a third plurality of cells having a more flexible structure than the second plurality of cells. The second plurality of cells may be disposed between the first and third pluralities of cells. Moreover, the first and third plurality of cells may have substantially identical flexibility.

In accordance with one aspect of the present invention, the first and third plurality of cells have a diamond shape, and the second plurality of cells has a hexagonal shape. Accordingly, the second plurality of cells may have an average void space area greater than the first and third plurality of cells' average void space area. In accordance with another aspect of the present invention, the first and third plurality of cells may have a greater average void space area than the second plurality of cells' average void space area. The upstream portion further may include a constricted section at an upstream end to permit coupling to a delivery device. For example, the constricted section may remain coupled to the delivery device for an acute treatment. In addition, the downstream component may include an atraumatic end.

The cross-sectional flow area at the outlet of the upstream component may be less than the cross-sectional flow area at the entry of the downstream component. The upstream component and the downstream component may be formed from a single frame. In addition, the downstream component's length may be greater than the upstream component's length. The upstream component's average angle of convergence may be greater than the downstream component's average angle of divergence. Further, the upstream component may be a nozzle that accelerates the fluid stream passing through the upstream component and the downstream component may be a diffuser that decelerates the fluid stream having the entrained additional fluid passing through the downstream component.

The invention may further include a delivery device for delivering the flow modulator. The delivery device includes a sheath having a lumen sized to hold the flow modulator therewithin in a contracted, delivery state during delivery, and an inner assembly slidably disposed within the lumen of the sheath to facilitate deployment out a distal end of the sheath.

In accordance with another aspect of the present invention, a method for altering fluid flow through a body lumen coupled to a branch lumen is provided. The method includes positioning the flow modulator and accelerating a fluid stream passing through the upstream component towards the downstream component to generate a low pressure region in the vicinity of the gap and to entrain additional fluid into the fluid stream as the fluid stream passes into the entry of the downstream component. For example, the method includes positioning the upstream component in an inferior vena cava such that the inlet is upstream from a branch off to a renal vein and the downstream component in the inferior vena cava such that the exit is downstream from the branch off to the renal vein, thereby drawing blood from the renal vein and improving kidney functionality. Drawing the blood from the renal vein to improve kidney functionality further reduces excess fluid to treat heart failure.

In accordance with another aspect of the present invention, the method includes positioning the upstream component in an inferior vena cava such that the inlet is upstream from a branch off to a hepatic vein and the downstream component in the inferior vena cava such that the exit is downstream from the branch off to the hepatic vein, thereby drawing blood to the inferior vena cava and improving splanchnic circulation. The method may further include coupling a constricted section to a delivery device for an acute treatment.

In accordance with yet another aspect of the present invention, another device for altering fluid flow through a body lumen coupled to a branch lumen is provided. The device includes an inner core having an upstream region and a downstream region, the upstream region having a first end and a cross-sectional area that increases from the first end towards the downstream region, and the downstream region having a second end and a cross-sectional area that decreases from the upstream region towards the second end. For example, the rate of increase of the cross-sectional area of the upstream region from the first end towards the downstream region may be greater than a rate of decrease of the cross-sectional area of the downstream region from the upstream region towards the second end. Accordingly, the inner core may accelerate a fluid stream passing around the upstream region towards the downstream region between the inner core and the branch lumen. In one embodiment, the fluid stream only passes around the upstream region towards the downstream region between the inner core and the branch lumen, and not through the inner core.

In accordance with one aspect of the present invention, the inner core is symmetric about a longitudinal plane extending along a longitudinal axis of the inner core. Thus, the diameter of the inner core constantly changes from the first end of the upstream region to the second end of the downstream region. The inner core may be completely suspended within the body lumen without contacting an inner wall of the body lumen. The region of the inner core having a maximum cross-section area may be positioned upstream of the branch lumen. Accordingly, the downstream region of the inner core may extend through the body lumen across the entire section where the body lumen intersects with the branch lumen.

BRIEF DESCRIPTION OF THE DRAWINGS

The present invention will be understood and appreciated more fully from the following detailed description taken in conjunction with the drawings in which:

FIGS. 29A and 29B are views of an upstream flow accelerator or a downstream flow decelerator, whose shape is changeable in accordance with another embodiment of the present invention, wherein FIG. 29B is a sectional view taken along lines B-B in FIG. 29A;

FIGS. 51A-51C are schematic views of a flow modulator with illustrative dimensions and corresponding flow pattern, in accordance with another embodiment of the present invention;

FIG. 53F is a cross-sectional view of the flow modulator of FIG. 52E;

FIGS. 57A-57C are schematic views of an inner core inserted into a flow modulator, in accordance with another embodiment of the present invention;

FIGS. 61A-61B are schematic views of a self-adjustable nozzle of a flow modulator, in accordance with another embodiment of the present invention;

FIGS. 62A-62B are schematic views of a flow modulator, in accordance with another embodiment of the present invention, inserted downstream and upstream, respectively;

DETAILED DESCRIPTION OF EMBODIMENTS

Devices and methods for altering flow in body lumens are provided for creating pressure differences and/or to induce fluid entrainment from branch lumens for enhancing or modifying fluid flow to treat different disorders or diseases.

Figure 1:
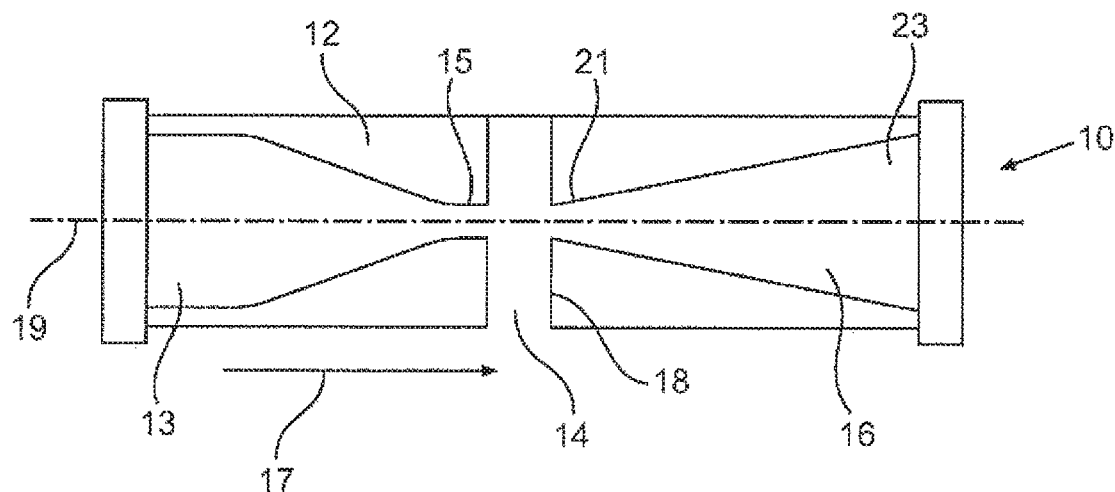
FIG. 1 is a schematic view of a fluid flow modulator, constructed and operative in accordance with another embodiment of the present invention.

Referring to FIG. 1, flow modulator 10 constructed and operative in accordance with a first embodiment of the present invention is described.

Flow modulator 10 includes upstream component 12 separated by gap 14 from downstream component 16. Gap 14 is designed to entrain fluid into a stream of fluid flowing from upstream component 12 to downstream component 14. As described below, upstream component 12 and downstream component 16 create a lower pressure region in the vicinity of gap 14, which preferably entrains fluid into the stream of fluid flowing across gap 14. Fluid entrainment is induced by shear-induced turbulent flux. In accordance with the principles of the invention, such entrainment is expected to transport blood or other body fluids to or from a region so as to improve organ function (e.g., from the renal vein(s) to the inferior vena cava to promote better functionality of the kidney(s) and/or from the hepatic vein(s) to the inferior vena cava to improve liver function, thereby treating disorders and/or diseases such as heart failure).

Upstream component 12 has inlet 13 and outlet 15 and preferably has a cross-sectional flow area that converges in a downstream direction (indicated by arrow 17) along part or all of the length of upstream component 12, such as but not limited to, a nozzle. In this manner, upstream component 12 accelerates flow of fluid through upstream component 12. Downstream component 16 has entry 21 and exit 23 and preferably has a cross-sectional flow area that diverges in a downstream direction along part or all of the length of downstream component 16 to server as a diffuser. Downstream component 16 thus decelerates flow of fluid through downstream component 16. The distance between outlet 15 and entry 21 is selected to generate a low pressure region in the vicinity of gap 14, while minimizing pressure loss and reducing resistance to fluid flow from the branch lumen(s), e.g., renal flow. For example, as explained in the data below, too great a distance may create a significant pressure loss that causes flow retrograde flow into the branch lumens. Applicant has discovered that using a maximum distance between outlet 15 and entry 21 (e.g., less than 25 mm and more preferably less than 15 mm when the device is deployed at the renal veins) will improve flow rates in the branched vessel(s) with relatively low pressure loss. Gap 14 also permits flow modulator 10 to entrain additional fluid into the fluid stream as the fluid stream passes into entry 21 of downstream component 16.

PCT Patent Applications WO 2016/128983, WO 2018/029688, and WO 2019/097424 describe several converging and diverging structures that may be utilized as flow modulator 10 in accordance with the principles described herein, and the disclosures of each of those applications are incorporated herein by reference in their entireties. Other converging and diverging structures suitable for use in accordance with the principles of the present invention are described herein. In addition, the present invention may be implemented using other kinds of converging and diverging structures, such as Stratford ramp nozzles (e.g., in which flow through the nozzle is on the verge of separation, which gives the diffuser the best length to efficiency ratio), de Laval nozzles (e.g., asymmetric hourglass shape), variable cross-sectional area nozzles and venturis, ramped nozzles and venturis, and others. The central axis of the diverging portion may be disposed in-line with, or offset from, the central axis of the converging portion.

Gap 14 may be located in fluid flow structure 18 and defines boundaries for the pathway to divert or entrain additional fluid to flow into downstream component 16. Fluid flow structure 18 may include one or more conduits that are not collinear with a direction of flow (indicated by arrow 17) from upstream component 12 to downstream component 16. For example, the conduits of fluid flow structure 18 may be perpendicular to direction of flow, may be inclined at an angle, e.g., 30° angle, 45° angle, or include any other suitable configuration.

In the embodiment of FIG. 1, upstream component 12 and downstream component 16 share common, collinear flow axis 19. However, the invention is not limited to this construction and upstream component 12 may be angled with respect to downstream component 16. Upstream component 12 and downstream component 16 also may lie along a continuously curved path.

Fluid flow structure 18 may or may not connect upstream component 12 to downstream component 16. For example, if fluid flow structure 18 employs conduits, then fluid flow structure 18 preferably connects upstream component 12 to downstream component 16. However, fluid flow structure 18 of FIG. 1 may not be formed by conduits, but instead by two walls that are not connected to each other. In such an example, fluid flow structure 18 does not connect upstream component 12 to downstream component 16.

Upstream component 12, downstream component 16, and fluid flow structure 18 may be constructed as grafts, stents (coated or uncoated), stent grafts (coated or uncoated), and the like, and are formed of biocompatible materials, such as stainless steel or nitinol. The outer contours of any of upstream component 12, downstream component 16, and fluid flow structure 18 may be sealed against the inner wall of the body lumen (such as by being expanded thereagainst), or alternatively may not be sealed, depending on the particular application.

Flow modulator 10 is sized and shaped to be implanted in a body lumen. In one embodiment, flow modulator 10 may be compressed for delivery (e.g., percutaneous delivery within a delivery sheath) and expanded upon deployment (e.g., self-expanding upon release from the end of the delivery sheath or balloon expandable). Flow modulator 10 may be inserted into the body lumen in an antegrade or retrograde manner and similarly may be removed antegrade or retrograde. Flow modulator 10 may be used as an acute device to be removed after few hours/days or a chronic permanent device or a device that can be retrieved after long-term implantation. When used as an acute device, flow modulator 10 may remain coupled to a delivery/retrieval device, e.g., sheath and/or wire/shaft, throughout the short-term implantation for ease of device delivery and retrieval. Flow modulator 10 may be compressible while disposed within a body lumen to allow periodic wash-out of stagnant flow zones created adjacent to flow modulator 10. For example, flow modulator 10 may be partially or fully reduced in diameter within the body lumen to allow blood flow through a stagnant flow zone.

Preferably, upon expansion, flow modulator 10 is sized to contact the inner wall of the body lumen to anchor flow modulator 10 within the lumen. Flow modulator 10 may be formed from one or more frames and may be coated with one or more biocompatible materials. For example, the frame(s) may be formed of a metal (e.g., shape memory metal) or alloy or a combination thereof (e.g., a stent made of stainless steel or nitinol or cobalt chromium). For some applications, the frame(s) may include a braided stent. In the case of more than one frame, the frames may be joined together by a suitable technique, such as welding. For example, upstream component 12 and downstream component 16 may be formed from a common frame or two frames that may be joined prior to implantation. Flow modulator 10 may be at least partially coated with a biocompatible, covering material (although they may be used as bare metal, uncoated stents as well). The biocompatible material may be a fabric and/or polymer such as expanded polytetrafluoroethylene (ePTFE), woven, knitted, and/or braided polyester, polyurethane, DACRON (polyethylene terephthalate), silicone, polycarbonate urethane, or pericardial tissue from an equine, bovine, or porcine source. The biocompatible coating may impede or block fluid flow where applied to the frame. The order of the joining and coating processes may be joining before coating or coating before joining. The biocompatible material may be coupled to the frame(s) via stitching, spray coating, encapsulation, electrospinning, dip molding, and/or a different technique.

In a preferred embodiment, biocompatible material is fluid impermeable. However, for some applications, the surfaces need not be impermeable, but may have a permeability that is sufficiently low as to substantially prevent blood from flowing through the longitudinal portion of the body lumen via any flow path other than through the flow channel defined by the inner surfaces of flow modulator 10. For some applications, each of the surfaces has permeability per unit length of less than 0.25 micrometers (i.e., between 0 and 0.25 micrometers), where the permeability per unit length is defined based upon the following equation, which is based upon Darcy's Law: $k/\Delta x = V\mu/\Delta p$, where k is permeability, $\Delta x$ is length (in meters), V is average velocity (in meters per second), $\mu$ is fluid viscosity (measured in Pascal-seconds), and $\Delta P$ is the pressure differential measured in Pascals).

Although the invention is not bound by any theory, a simplified engineering explanation is now provided to help understand how upstream component 12 and downstream component 16 operate to create reduced pressure at gap 14.

The Bernoulli equation governs the relationship between fluid velocity and pressure (neglecting the height difference):

$$P_1 + \tfrac{1}{2} \cdot \rho \cdot V_1^2 = P_2 + \tfrac{1}{2} \cdot \rho \cdot V_2^2 + E_{loss}$$

P=pressure
$\rho$=density
V=velocity
1=conditions at the inlet (upstream component 12)
2=conditions at gap 14
Mass Conservation (Same Flow Rate):

$$V_1 \cdot A_1 = V_2 \cdot A_2$$

A=Flow cross section
$E_{loss}$=Energy loss
For example, if flow modulator 10 is installed near the kidneys with upstream component 12 in the inferior vena cava, then $V_1$ and $A_1$ are the velocity and flow area, respectively, at the inferior vena cava.

The flow velocity at the gap ($V_2$) is designed to achieve the desired pressure reduction. For example, for 0.5 meter per second velocity and 3 times area ratio, a suction of about 6-8 mm Hg can be achieved. In the case of deployment near the kidney, this pressure differential is expected to improve renal function by improving renal perfusion pressure. The pressure will change due to improvement in the renal flow.

In another example, flow modulator 10 can be installed near a bifurcation to divert emboli from the bifurcation. In yet another example, flow modulator 10 may be deployed in the aortic arch to reduce peak systolic pressure.

Figure 2:
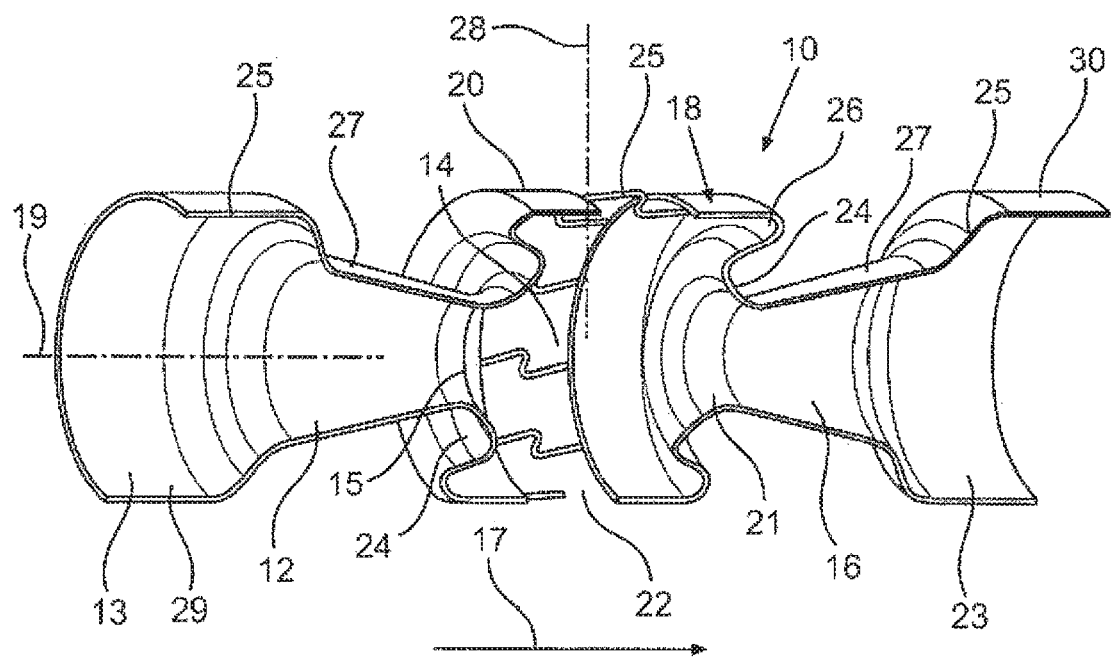
FIG. 2 is a side-sectional view of a fluid flow modulator, constructed and operative in accordance with another embodiment of the present invention.

Referring now to FIG. 2, another version of flow modulator 10 is described, with like elements being designated by like numerals. In this embodiment, fluid flow structure 18 includes central portion 20, which may be cylindrical, that connects upstream component 12 to downstream component 16. Fluid flow structure 18 extends outward from outlet 15 of upstream component 12 and from entry 21 of downstream component 16, such that fluid flow structure 18 is sized to contact an inner wall of the body lumen. Central portion 20 may be formed with one or more apertures 22 that define gap 14 for fluidly communicating with branch lumens, so that additional fluid from the branch lumen or lumens flows into gap 14 and is entrained with fluid flowing from upstream component 12 to downstream component 16.

Notably, junction 24 between fluid flow structure 18 and upstream component 12 and/or downstream component 16 may be curved. This design may help streamline the flow, and prevent creation of local turbulences or eddy currents that may adversely affect the pressure or flow characteristics. Fluid flow structure 18 also may diverge outwards (at numeral 26) in a direction away from central axis 28 of fluid flow structure 18. This diversion may be used to create different flow affects, depending on the application. The diversion also enables moving upstream component 12 and downstream component 16 closer to each other. For example, junction 24 between fluid flow structure 18 and upstream and downstream components 12 and 16 may be S-shaped to move outlet 15 closer to entry 21 to minimize the distance between those parts of fluid modulator 10.

As best shown in FIG. 2, fluid modulator 10 may be formed from frame 25 and coated with biocompatible material 27, using materials described above. In FIG. 2, fluid modulator 10 is formed as a single frame that includes upstream component 12, gap 14, and downstream component 16. Upstream component 12 is coated with biocompatible material 27 to define the fluid flow channel through upstream component 12, such that fluid flowing through a body lumen enters inlet 13, accelerates through the converging portion of upstream component 12, and exits out outlet 15 into the portion of fluid modulator 10 having gap 14. A low pressure region is formed at gap 14 by the shapes of upstream component 12 and downstream component 16. Additional fluid from the branch lumen(s) at gap 14 is entrained into the fluid stream passing from outlet 15 to entry 21. Downstream component 16 also is coated with biocompatible material 27 to define the fluid flow channel through downstream component 16 such that the fluid stream from outlet 12 together with the additional fluid passing through gap 14 enter entry 21, decelerate through the diverging portion of downstream component 16, and exit out exit 23 back into the body lumen. In this example, gap 14 is created by an uncoated portion of frame 25.

Upstream component 12 may have fixation area 29 sized for anchoring upstream component 12 within the body lumen. Fixation area 29 is sized to contact the inner wall of the body lumen and preferably has a diameter the size of, or slightly larger than, the diameter of the body lumen. Fixation area 29 may have a constant diameter for a length suitable for anchoring upstream component 12 in the body lumen. Similarly, downstream component 16 may have fixation area 30 sized for anchoring downstream component 16 within another portion of the body lumen. Fixation area 30 is sized to contact the inner wall of the other portion of the body lumen and preferably has a diameter the size of, or slightly larger than, the diameter of that portion of the body lumen. Fixation area 30 may have a constant diameter for a length suitable for anchoring downstream component 16 in the body lumen. Preferably fixation areas 29 and 30 are configured to seal fluid modulator 10 within the body lumen so that fluid only flows into the fluid channels created by fluid modulator 10 and does not flow around fixation area 29 or fixation area 30.

Still referring to FIG. 2, fluid flow structure 18 has the same diameter as fixation areas 29 and 30, which may enhance anchoring immediately proximal and distal to the branch lumen(s) while positioning gap 14 at the intersection between the body lumen and the branch lumen(s). In this manner, fluid flow structure 18 forms one or more additional fixation areas (illustratively, two additional fixation areas) between fixation areas 29 and 30. As shown, the portions of fluid flow structure 18 coated with biocompatible material 27 (on opposing sides of uncoated frame 25 that defines gap 14) act as fixation/sealing areas. Fluid flowing in the body lumen may be trapped between the outer surface of upstream component 12 and the body lumen wall between fixation area 29 and the upstream portion of fluid flow structure 18. In addition, or alternatively, fluid flowing in the body lumen may be trapped between the outer surface of downstream component 16 and the body lumen wall between fixation area 30 and the downstream portion of fluid flow structure 18.

Figure 3A:
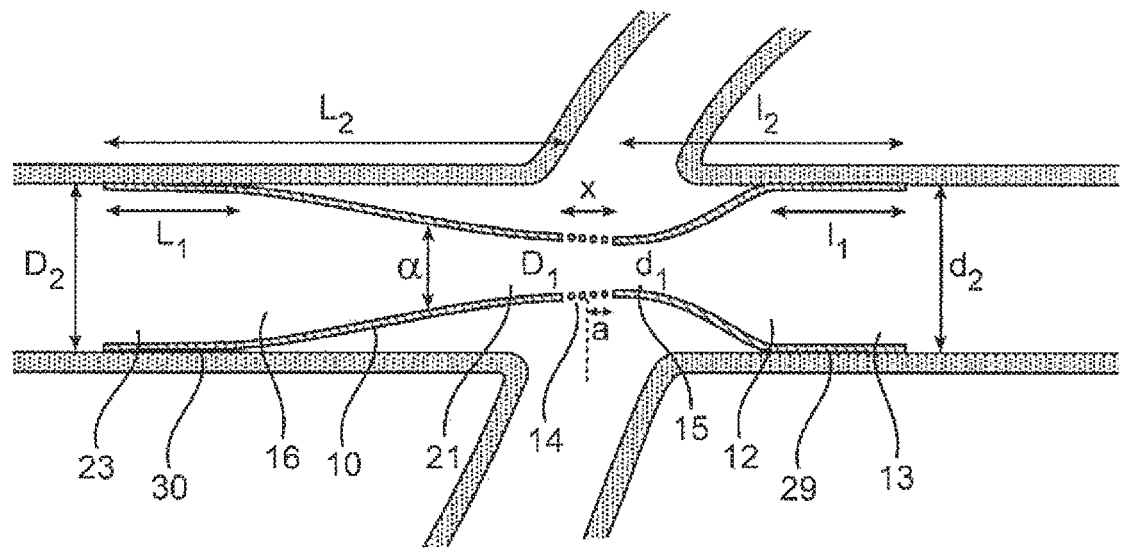
FIGS. 3A-19 are schematic views of different fluid flow modulators of the invention, some of which are shown installed in various body lumens, in accordance with embodiments of the present invention.

Referring now to FIG. 3A, an exemplary flow modulator is shown with symbols depicting dimensions of flow modulator 10 in accordance with a preferred embodiment. The dimensions provided with respect to FIG. 3 are for an embodiment suitable for implantation in the inferior vena cava. In particular, inlet 13 of upstream component 12 is configured to be disposed upstream from a branch off to a renal vein(s), downstream component 16 is configured to be disposed in the inferior vena cava, such that exit 23 is downstream from the branch off to the renal vein(s), and gap 14 is at the branch to the renal vein(s). d1 is the diameter of outlet 15 of upstream component 12. d1 is selected to create a jet velocity for a given device resistance. In the example of chronic cases, d1 may be in a range from 3.5-8 mm. In acute cases, d1 preferably is in a range from 3-7 mm. d2 is the diameter of inlet 13 in the deployed, expanded state and may be in a range from 12-40 mm. l1 is the length of fixation area 29 and may be in a range from 5-30 mm. l2 is the overall length of upstream component 12 and may be in a range from 15-60 mm. x is the distance from outlet 15 of upstream component 12 to entry 21 of downstream component. For x, a shorter distance from outlet 15 to entry 21 will provide better performance for downstream component 16, but will result in lower renal flow because there is a greater resistance to flow from the renal vein(s) to downstream component 16. Thus, distance x preferably is selected (e.g., in a range from −5-25 mm) to provide improved renal flow rate with minimal pressure loss.

Still referring to FIG. 3, distance x may be negative, as outlet 15 of upstream component 12 may be positioned downstream from entry 21 of downstream component 16. a is the distance from outlet 15 of upstream component 12 to the center line of the branched lumen, e.g., the right renal vein, and may be in a range from −25-25 mm. L1 is the length of fixation area 30 and may be in a range from 5-30 mm. L2 is the overall length of downstream component 16. L2 is preferably greater than 12 because a diverging shape creates a much higher pressure loss than a converging shape. The ratio of L2:l2 may be from 1:1 to 3:1. D1 is the diameter at entry 21 of downstream component 16 and is preferably larger than d1. Thus, the cross-sectional flow area at outlet 15 of upstream component 12 is less than the cross-sectional flow area at entry 21 of downstream component 16. D1 is selected to receive all the fluid jetted from outlet 15. The ratio of D1:d1 may be from 1:1 to 2:1. In addition, D1 should be greater for larger distances x to ensure receipt of the fluid jetted from upstream component 12. D2 is the diameter of exit 23 in the deployed, expanded state and may be in a range from 12-40 mm.

In FIG. 3, a is the average angle of divergence in downstream component 16 and may be in a range from 5-30 degrees. Preferably, the angle of divergence in downstream component 16 is less than the angle of convergence in upstream component 12, and is expected to prevent pressure loss. In addition, downstream component 16 should have slow change in area adjacent to entry 21 (closer to the renal vein)—any additional pressure loss will reduce the inferior vena cava flow rate and thus will reduce the effectiveness of the device. The angle of divergence in downstream component 16 may be constant or may change along the length of downstream component 16. When the angle of divergence changes along the length (as shown in FIG. 2, for example) the angle of divergence is preferably smallest (e.g., in a range from 5-30 degrees) adjacent to entry 21. A slow change in the cross-sectional flow area adjacent to entry 21 is preferred because the fluid velocity decreases as the cross-sectional flow area increases, hence the pressure loss. Accordingly, the angle of divergence is smallest at entry 21 where the fluid flow is at maximum velocity within downstream component 16.

Fluid modulator 10 of FIG. 3A may be formed from one frame that defines upstream component 12, gap 14, and downstream component 16. In this example, upstream component 12 and downstream component 16 are each coated with a biocompatible material while gap 14 is created by an uncoated portion of the frame.

Figure 3B:
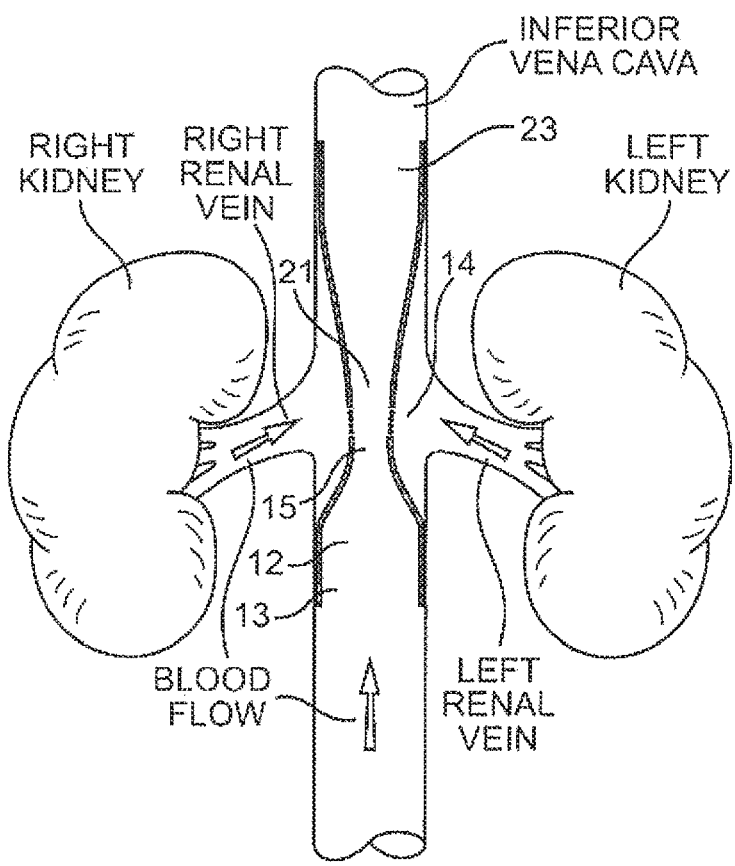

FIG. 3B shows flow modulator 10 of FIG. 3A implanted in the inferior vena cava at the renal veins. Upstream component 12 is in the inferior vena cava such that inlet 13 is upstream from a branch off to the left and right renal veins and downstream component 16 is in the inferior vena cava such that exit 23 is downstream from the branch off to the renal veins. While the right and left renal veins are usually at different heights along the inferior vena cava, gap 14 is generally positioned in the vicinity of the branches to the renal veins (or other branch lumens when used for other indications). For example, gap 14 may begin downstream from where the renal veins first intersect with the inferior vena cava, as illustrated. In addition, gap 14 may be entirely disposed within the intersection between the renal veins and the inferior vena cava, as illustrated. Outlet 15 of upstream component 12 may be positioned downstream from where the renal veins first intersect with the inferior vena cava, as shown. Accordingly, blood only enters fluid modulator 10 at inlet 13 and gap 14, which is downstream from where the branch lumen first intersects the main lumen. Entry 21 of downstream component 16 may be positioned upstream from where the intersection of the renal veins and the inferior vena cava ends, as shown. Flow modulator 10 creates reduced pressure at gap 14 and increases blood flow velocity to gap 14. Entrainment may also help transport blood to gap 14 from the kidneys. In this manner, the invention may draw blood from the kidneys to the renal veins and then to the inferior vena cava, thereby improving kidney functionality, reducing necrotic damage to the kidneys, and/or treating heart failure.

FIGS. 4-29B illustrate additional embodiments of flow modulators constructed in accordance with the principles of the present invention. In those figures, like elements are designated by like numerals.

Figure 4:
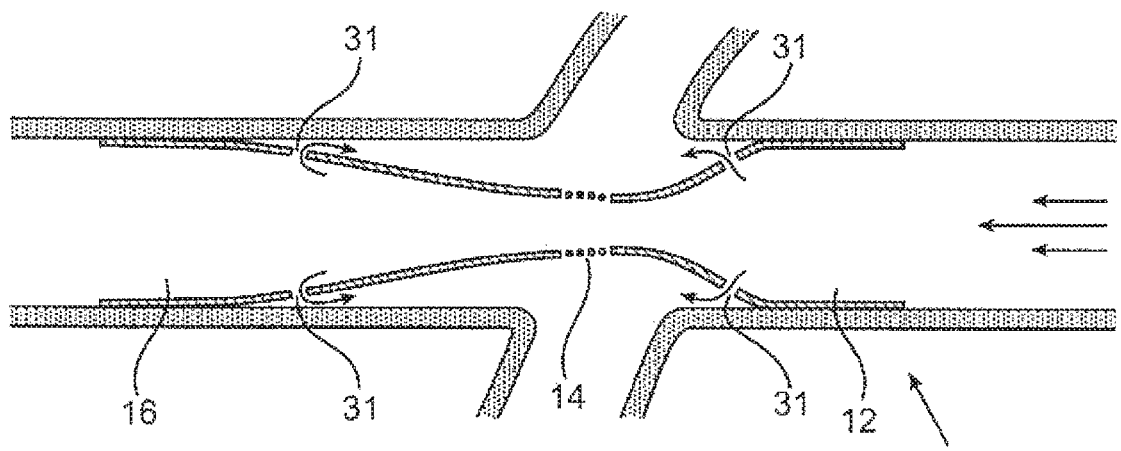

In FIG. 4, flow modulator 10 is constructed similarly to the fluid modulator of FIG. 3A although flow modulator 10 of FIG. 4 includes one or more openings 31 to reduce creation of stagnant flow zones. Fluid entering fluid modulator 10 flows out of openings 31 and into the body lumen. Openings 31 act as flushing flow channels for fluid and may encompass the entire circumference of fluid modulator 10 or be ports. Upstream component 12 or downstream component 16 or both (as illustrated) may include one or more openings 31. Openings 31 may be disposed on the converging portion of upstream component 12 and/or on the diverging portion of downstream component 16. When openings 31 are utilized, they are preferably located at least on downstream component 16, as downstream component 16 preferably is longer than upstream component 12 and thus more prone to longer stagnant flow zones.

Figure 5:
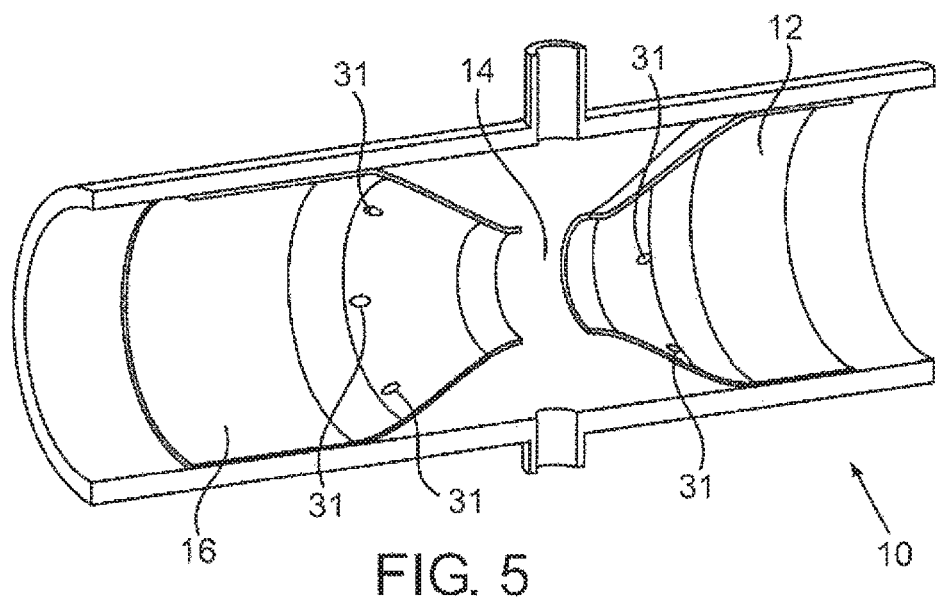

FIG. 5 is a cross-sectional view of fluid modulator 10 with plurality of openings 31 that act as flushing flow channels.

Figure 6:
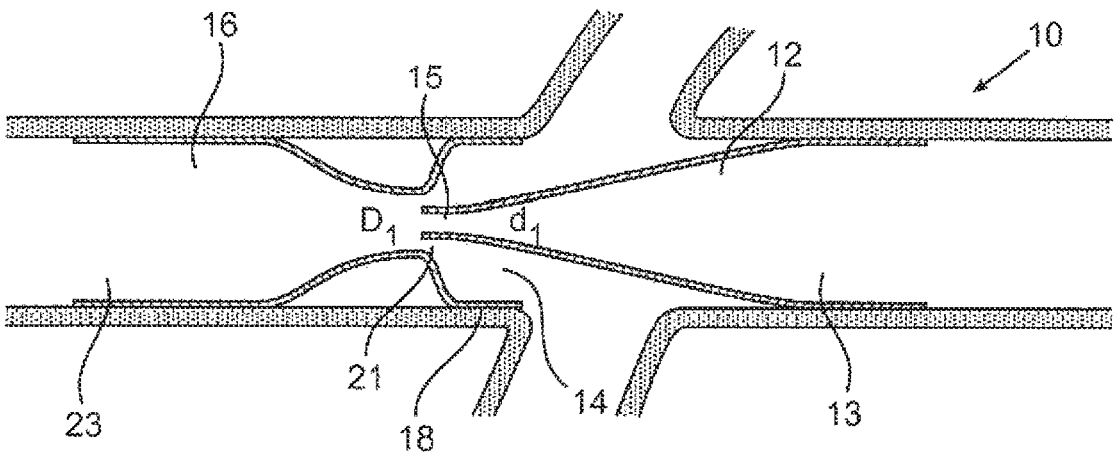

FIG. 6 illustrates fluid modulator 10, in which outlet 15 of upstream component 12 is positioned downstream from entry 21 of downstream component 16. In this embodiment, distance x is negative and D1 is larger than d1, e.g., at least 1 mm larger. Outlet 15 and entry 21 may both be positioned downstream of the intersection of the branch lumen(s) and the body lumen.

Figure 7:
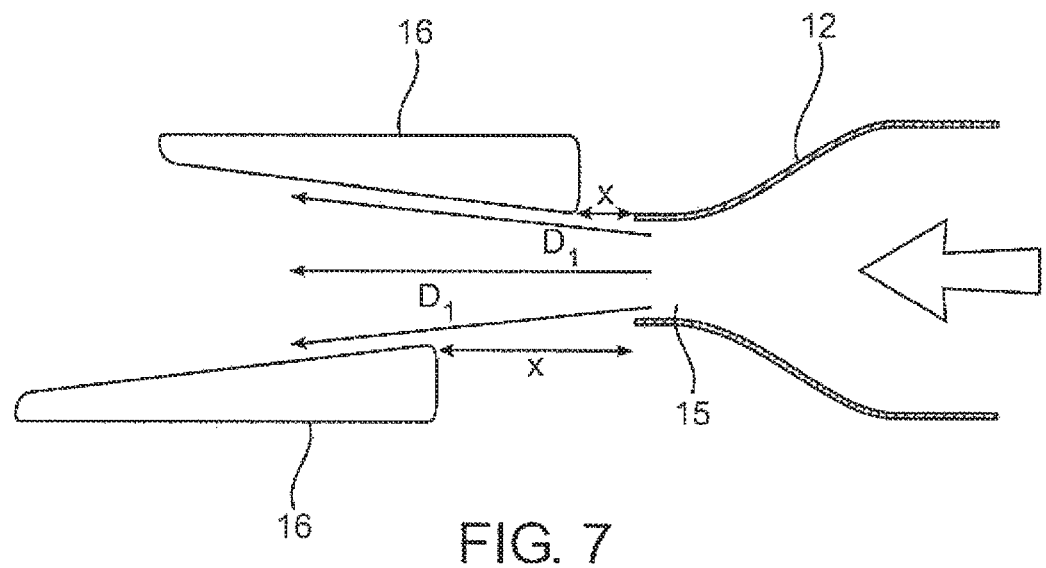

In FIG. 7, a method of selecting diameter D1 at entry of the downstream component 16 is described. Diameter D1 is selected relative to distance x from outlet 15 of upstream component 12 so as to receive all of the fluid jetted from outlet 15. D1 is greater for larger distances x to ensure receipt of the fluid jetted from upstream component 12.

Figure 8:
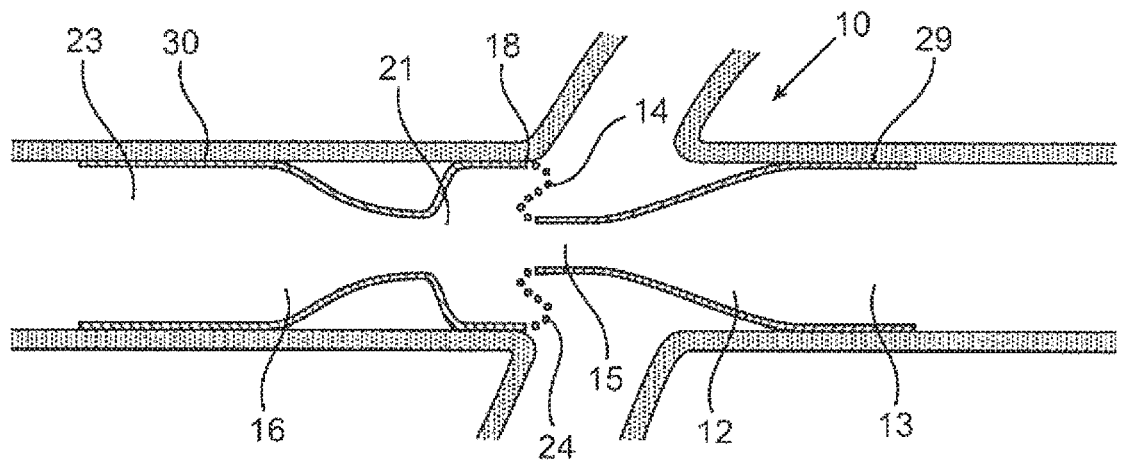

In FIG. 8, fluid modulator 10 is constructed similarly to fluid flow modulators 10 of FIGS. 2 and 3A, although gap 14 is disposed along a portion that extends radially outward from outlet 15 of upstream component 12. Gap 14 is formed along a curved portion (e.g., S-shaped) between fluid flow structure 18 and outlet 15, which allows downstream component 16 to be close to the branched lumen(s). In addition, fluid flow structure 18 is positioned downstream from the intersection between the branched lumen(s) and the body lumen to provide additional anchoring support. Fluid modulator 10 may be formed from a common frame (e.g., a single stent design), which facilitates control of the distance x between outlet 15 and entry 21. A single structure also facilitates co-axial orientation, especially for eccentric upstream and downstream components.

Figure 9:
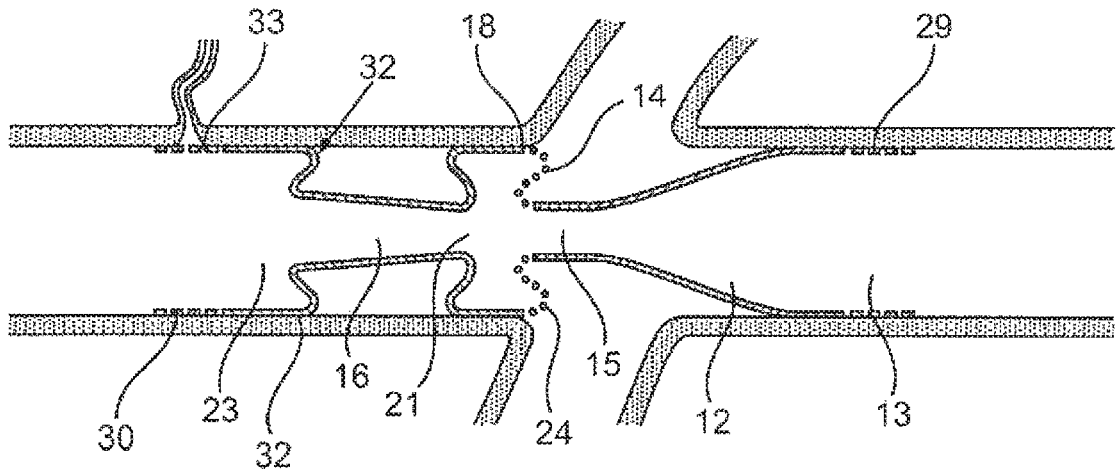

In FIG. 9, flow modulator 10 is constructed similarly to flow modulator 10 of FIG. 8, but in this case downstream component 16 includes curved portion 32 (e.g., S-shaped) that extends radially outward to contact the inner wall of the body lumen. A second curved portion in downstream component 16 provides further radially force to enhanced anchoring within the body lumen and also provides a longer diffuser for a given length. Flow modulator 10 also may include an additional gap(s) so as to not block fluid flowing from other branched vessels, such as gap 33 at the downstream end of downstream component 16.

Figure 10:
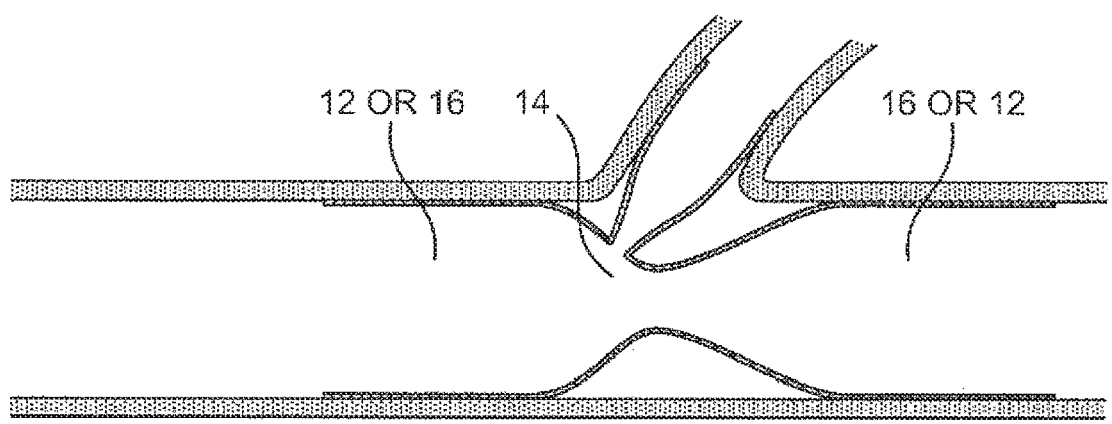
Figure 11:
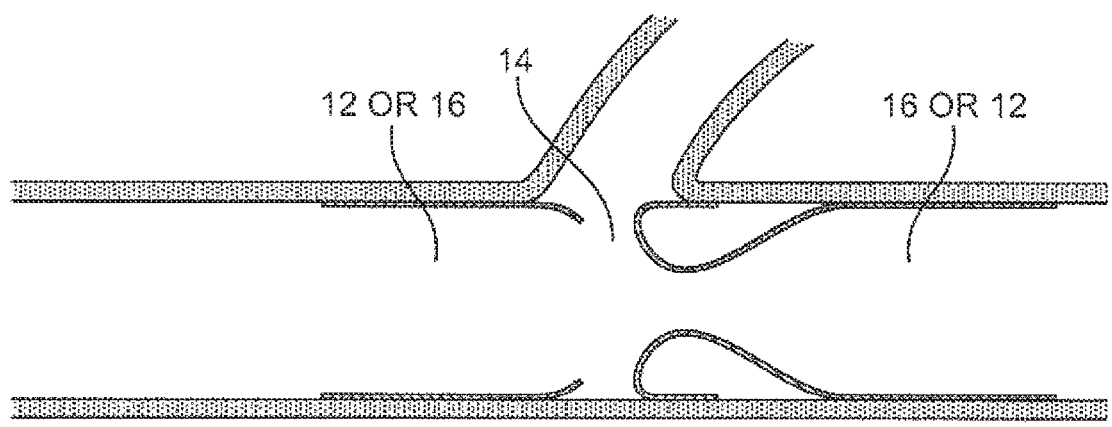

Referring now to FIG. 10 and FIG. 11, flow modulators 10 are described that include gap 14 positioned asymmetrically with respect to upstream component 12 and downstream component 16. In these embodiments, gap 14 is not positioned along the axis of the major vessel between upstream component 12 and downstream component 16, but instead is offset towards one of upstream component 12 and downstream component 16. The left side structure of FIGS. 10 and 11 may be deployed in the upstream or downstream direction, depending on the application; thus, the left side structure is labeled 12 or 16 and the right side structure is labeled 16 or 12.

Figure 12:
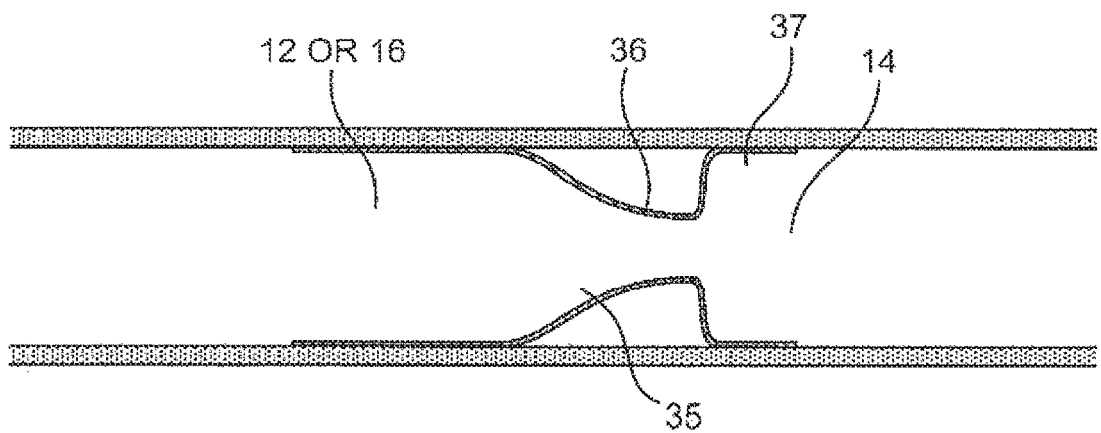

FIG. 12 depicts an embodiment designed for use as either upstream component 12 or downstream component 16, depending on the direction of flow. The structure includes relatively wide portion 35 that converges into relatively narrow portion 36. Relatively narrow portion 36 extends into diverging portion 37, which serves as a sealing portion.

Figure 13:
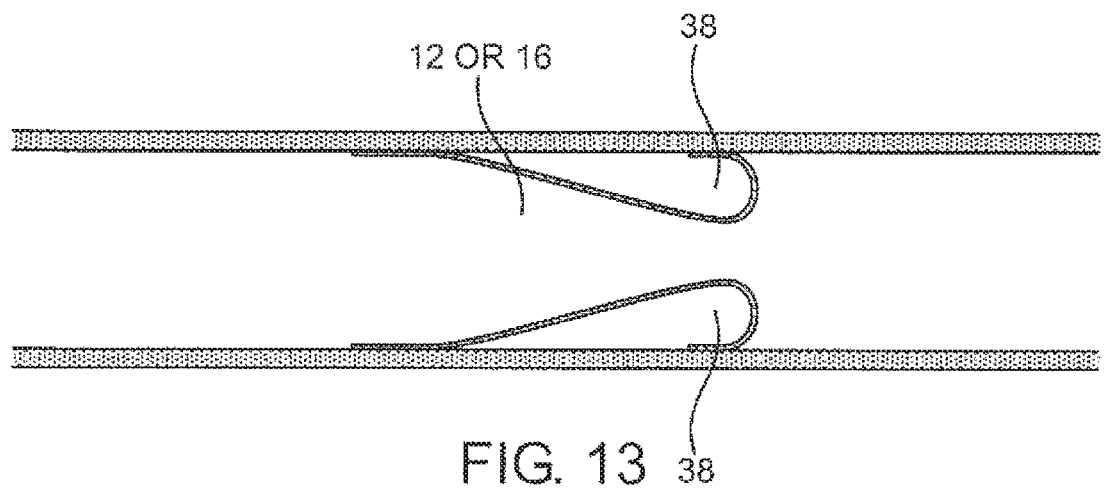

FIG. 13 depicts another embodiment designed for use as either upstream component 12 or downstream component 16, depending on the direction of flow. The structure of converging portion 38 includes surfaces that curve backward in the opposite direction.

Figure 14A:
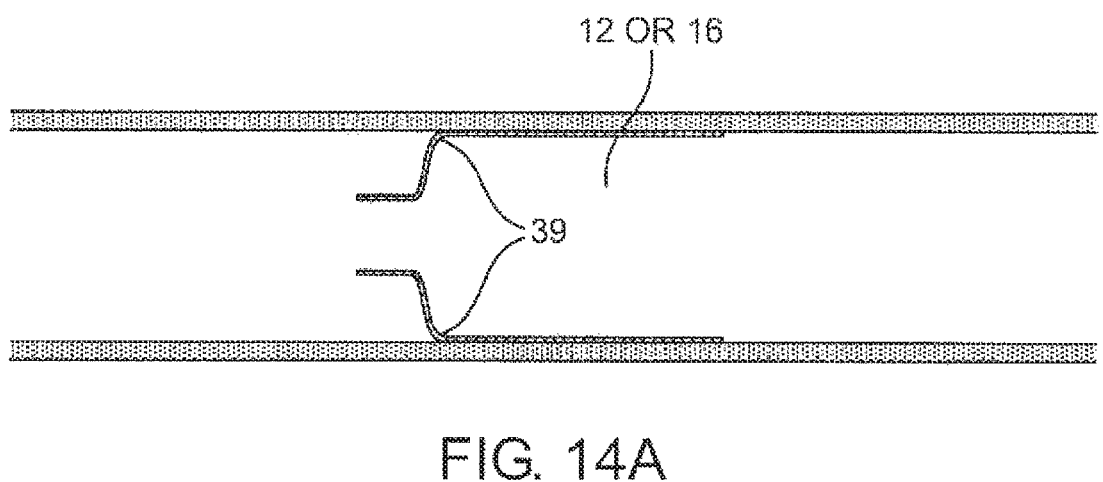
Figure 14B:
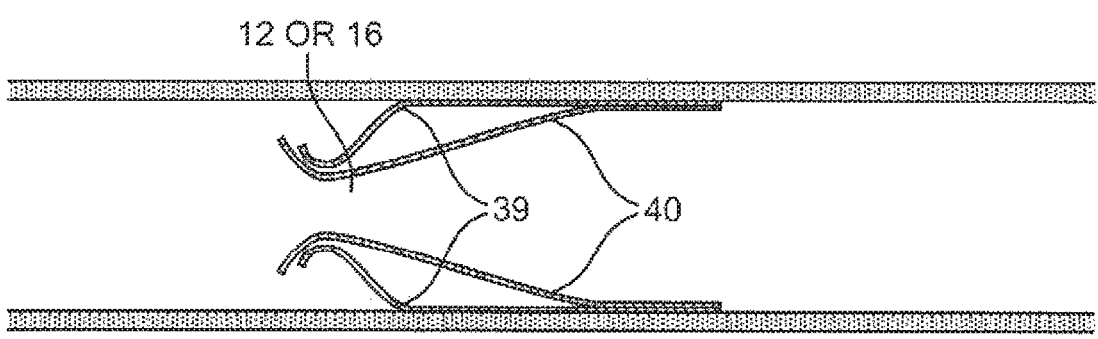

Referring to FIGS. 14A and 14B, another embodiment suitable for use as either upstream component 12 or downstream component 16 is described. In this embodiment, first stent member 39 may be installed with converging and diverging portions (FIG. 14A) and afterwards second stent member 40 may be installed over first stent member 39 to define a final converging and diverging shape. FIG. 14A may also be used as is, without the additional stent member. It is noted that the first stent member does not have to touch the second stent member (diffuser stent) and can be shorter than that shown in the drawings.

Figure 15:
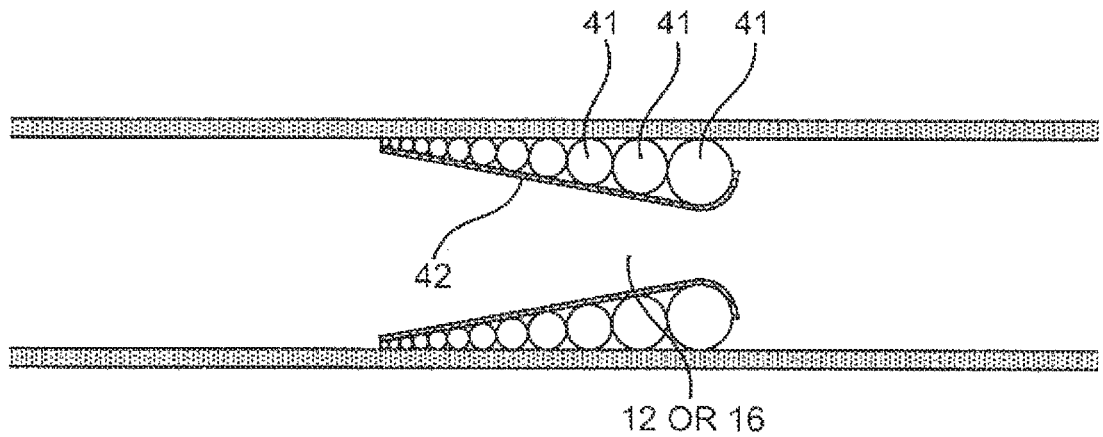

With respect to FIG. 15, an alternative design is described in which upstream component 12 is constructed of a plurality of discrete objects 41, such as spheres, balloons, rods, and the like, which gradually increase in size to create the converging effect. Similarly, downstream component 16 may be constructed of a plurality of discrete objects 41, such as spheres, balloons, rods, and the like, which gradually decrease in size to create the diverging effect. Discrete objects 41 optionally may be covered with membrane 42 to provide a smooth flow surface.

Figure 16:
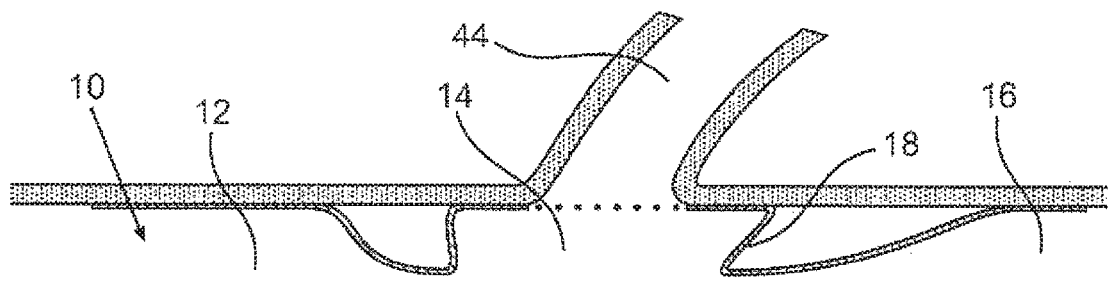

FIG. 16 depicts an embodiment of flow modulator 10 of FIG. 2 installed in a body lumen 43, such that gap 14 is situated at a bifurcation 44.

Figure 17:
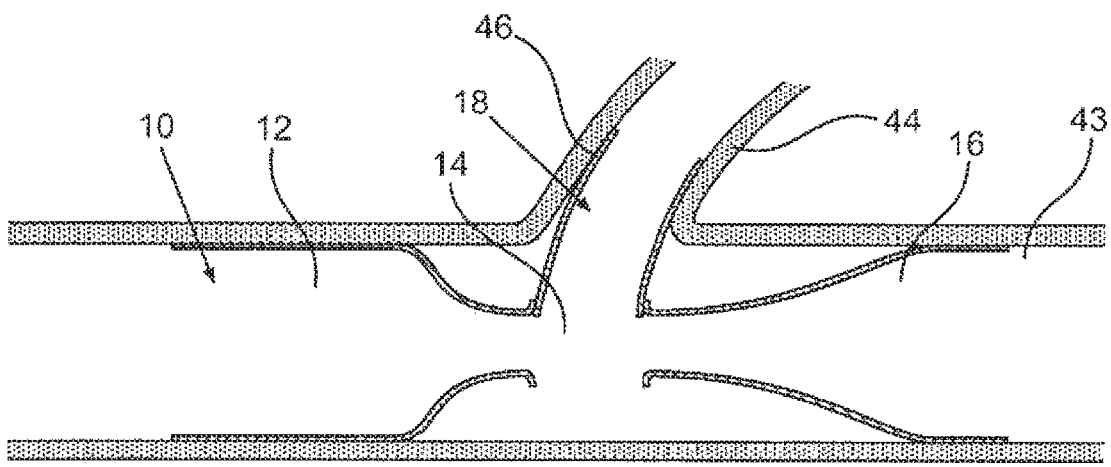

FIG. 17 depicts another embodiment of flow modulator 10 deployed in body lumen 43, such that gap 14 is situated at bifurcation 44. In this embodiment, fluid flow structure 18 includes extension 46 that is deployed in bifurcation 44. Alternatively, the opening in the stent graft at gap 14 may be used instead of sleeve-like extension 46.

Figure 18:
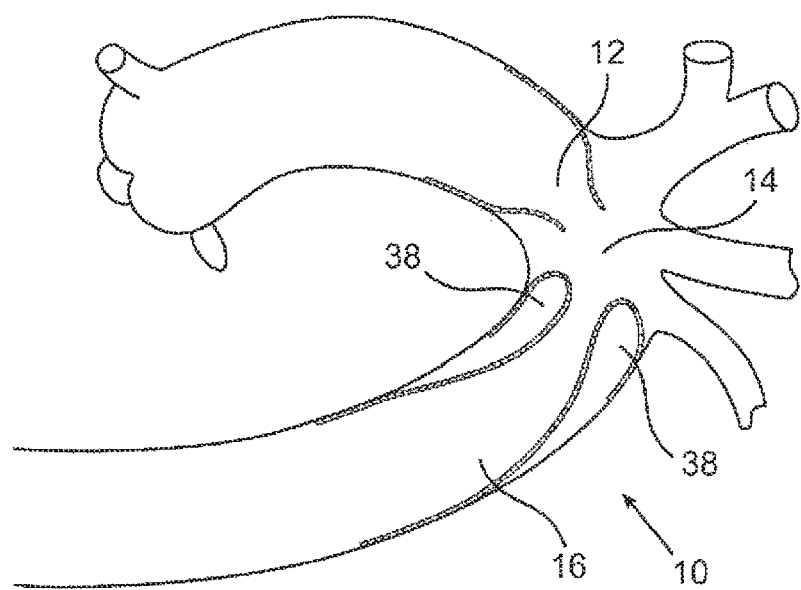

FIG. 18 depicts the flow modulator of one of the embodiments installed in the aortic arch, such that gap 14 is situated at the bifurcation of the carotid arteries. This installation may be used to reduce peak pressure gradients or to divert emboli away from the carotid arteries with very little pressure loss.

Figure 19:
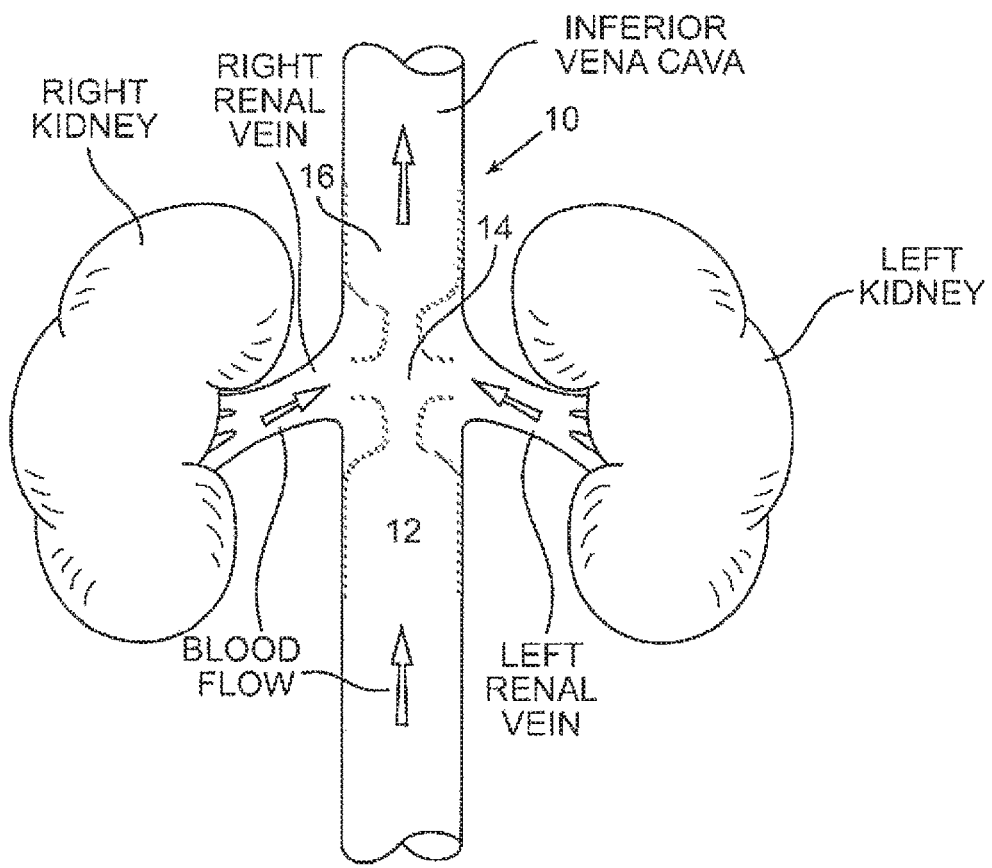

FIG. 19 depicts a flow modulator of the invention deployed near the kidneys. For example, upstream component 12 may be installed in the inferior vena cava just below (upstream to) the branch off to the renal vein and the downstream component 16 may be installed in the inferior vena cava just above (downstream to) the branch off to the renal vein. Gap 14 is located at the branch to the renal vein. Flow modulator 10 creates a reduced pressure region in the vicinity of gap 14 and increases blood flow velocity at gap 14. Entrainment may also help draw blood into the gap from the kidneys. In this manner, the invention can draw blood from the kidneys to the renal veins and then to the inferior vena cava, thereby improving kidney functionality and reducing necrotic damage to the kidneys.

Figure 20:
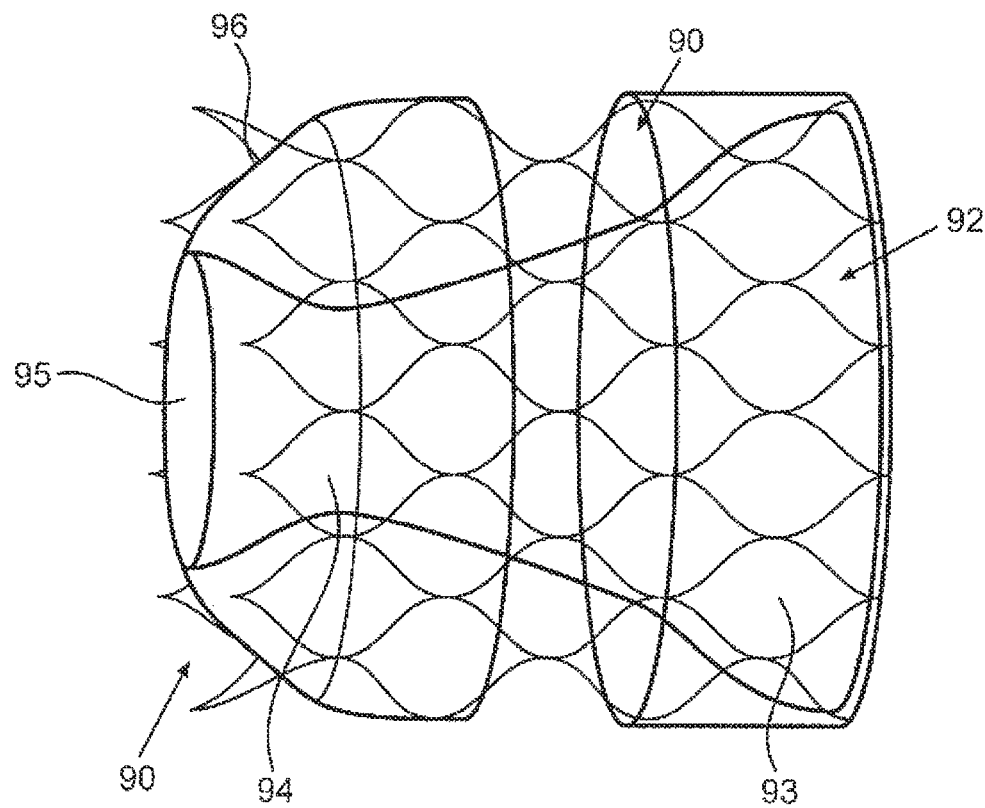
FIGS. 20 and 21 are side views of illustrative flow accelerators constructed in accordance with the principles of the present invention.

Referring now to FIG. 20, another embodiment is described, which is configured for use as either upstream component or downstream component, depending on the direction of flow. The structure includes outer stent 90 and inner stent 92. Outer stent 90 may be cylindrical. Inner stent 92 may include relatively wide portion 93 that converges into relatively narrow portion 94. Relatively narrow portion 94 extends into slightly diverging portion 95 with very little energy loss. The two stents may be joined together (for example, by welding or other suitable technique) and at least partially coated with coating 96 (although they may be used as bare metal, uncoated stents as well). The order of the joining and coating processes may be joining before coating or coating before joining.

Figure 21:
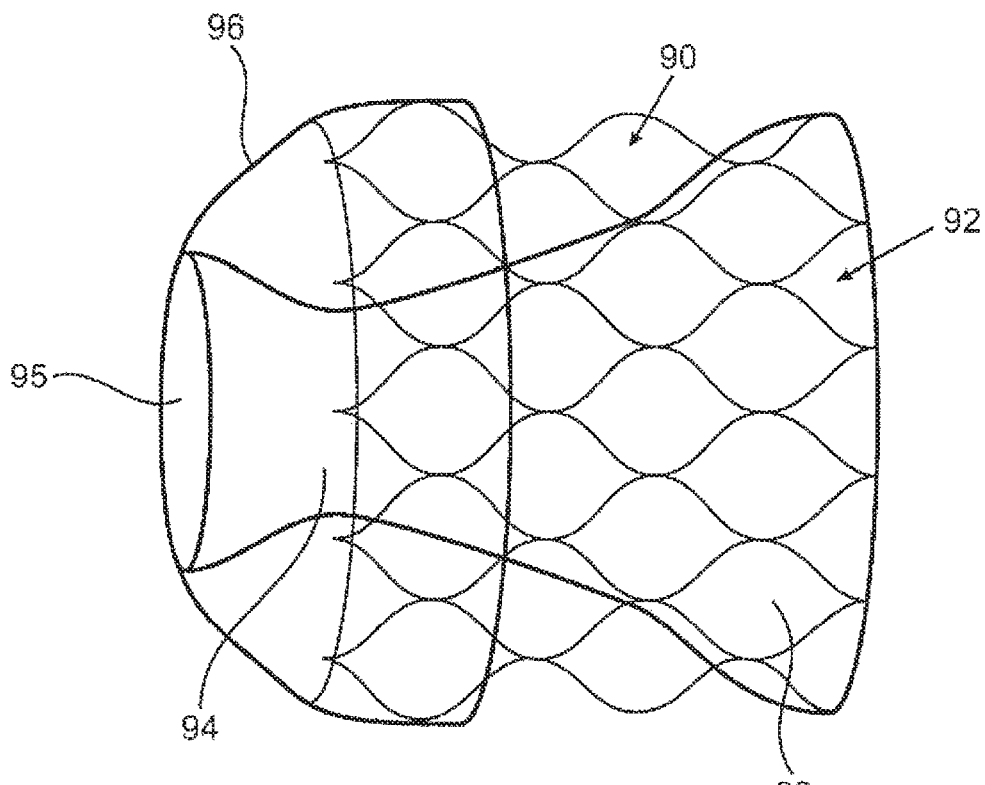

Referring now to FIG. 21, another version of the embodiment of FIG. 20 is depicted in which outer stent 90 is shorter, so that coating 96 extends over the end of outer stent 90.

Figure 22:
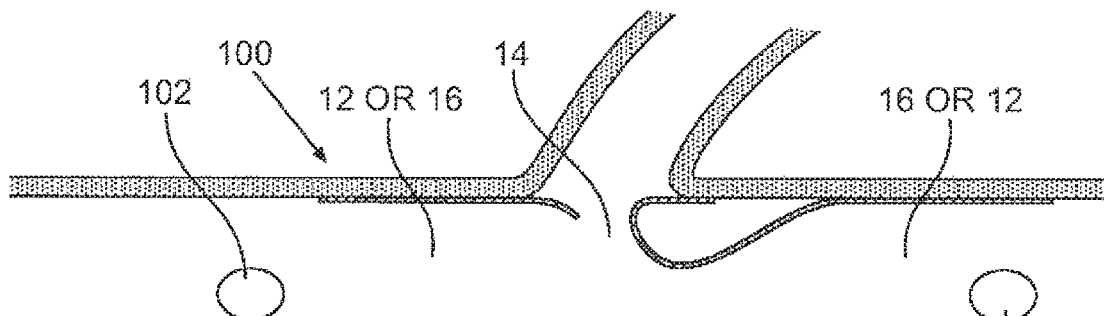
FIG. 22 is a schematic view of a fluid flow modulator, in accordance with another embodiment of the present invention, and including a pump (either downstream or upstream)

With respect to FIG. 22, flow modulator 100, in accordance with a further embodiment of the present invention is described. Flow modulator 100 includes pump 102, such as an axial flow pump, centrifugal pump, booster pump, chopper pump or other. Pump 102 may be secured in place by a stent or may be coupled to a portion of the upstream component 12 or downstream component 16. Pump 102 may be located either downstream or upstream, depending on the particular application. Pump 102 may be used to augment blood flow and filtration, for example.

Any of the foregoing embodiments of the device of the present invention may serve to divert emboli or other debris, so there is no need to use an extra filtration device. One example is using the upstream component or downstream component at or near the carotid arteries to divert emboli or other debris.

Figure 23:
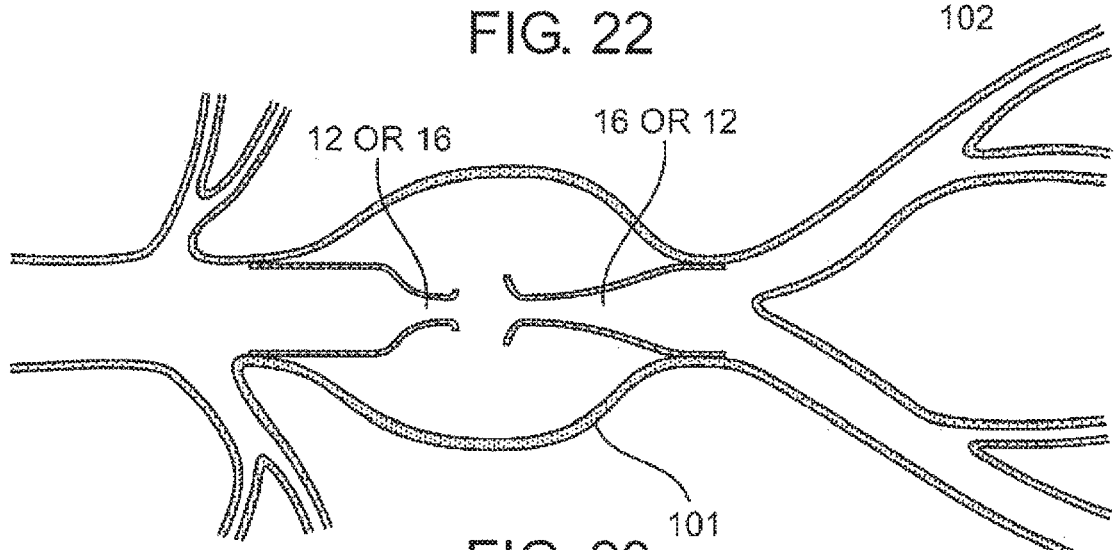
FIG. 23 is a schematic view of a fluid flow modulator installed in an aneurysm, in accordance with another embodiment of the present invention.

Referring now to FIG. 23, exemplary flow modulator 10 is installed in aneurysm 101 to lower pressure at the aneurysm site, and reduce the risk that the aneurysm will increase in size or burst, and may even cause the aneurysm to decrease in size. In this case, the flow modulator is expected to provide beneficial effect even without sealing against the aneurysm. In addition, if there are one or more side branch lumens at or near the aneurysm site, the device not only will reduce the pressure but also permit blood to flow to the side branches. In this application, the device of the present invention provides significant benefit as compared to previously-known circular stent grafts, which disadvantageously may block the side branches. If there are no side branches, then the device is expected to reduce pressure without increasing the blood flow. Optionally, a filter may be used with the flow modulator to prevent embolic debris from flowing from the aneurysm to other blood vessels.

Figure 24:
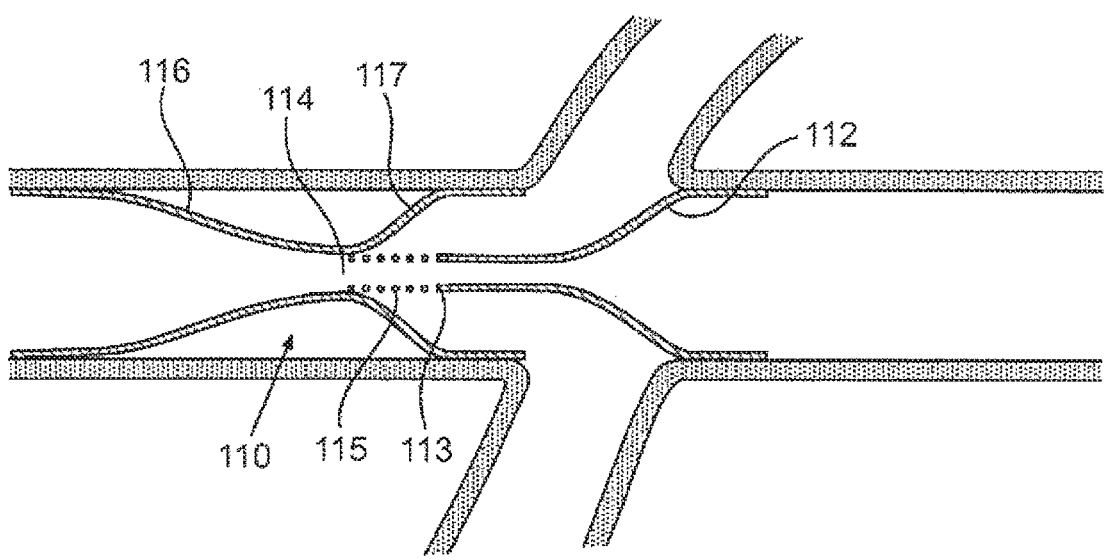
FIG. 24 is a schematic view of a fluid flow modulator, in accordance with another embodiment of the present invention, in which an outlet nozzle of an upstream flow accelerator enters a mouth portion of a downstream flow decelerator.

Referring now to FIG. 24, flow modulator 110, in accordance with another embodiment of the present invention is described. Flow modulator 110 includes upstream component 112 with outlet 113, and downstream component 116 that has an upstream divergent mouth entry 117. Outlet 113 enters entry 117 and this area serves as gap 114. Outlet 113 may be coupled with support 115 to a portion of downstream component 116, for example, to center outlet 113 with respect to entry 117. Alternatively, a separate stent structure (which does not hinder flow) may be used to support outlet 113. The straight portion in downstream component 116 may help axially align the flow before it is diffused and reduce flow separation from the diffuser wall, thereby reducing pressure losses.

FIG. 24 depicts flow modulator 110 deployed in a renal application. In this case, upstream component 112 may be installed in the inferior vena cava, upstream of the branch off to the renal vein, and downstream component 116 may be installed in the inferior vena cava, downstream of the branch off to the renal vein. Outlet 113 also is disposed downstream of the branch off to the renal vein. Similar to the embodiment of FIG. 19, flow modulator 110 creates reduced pressure at outlet 113 in gap 114, which increases blood flow velocity from the renal vein to the gap.

Figure 25:
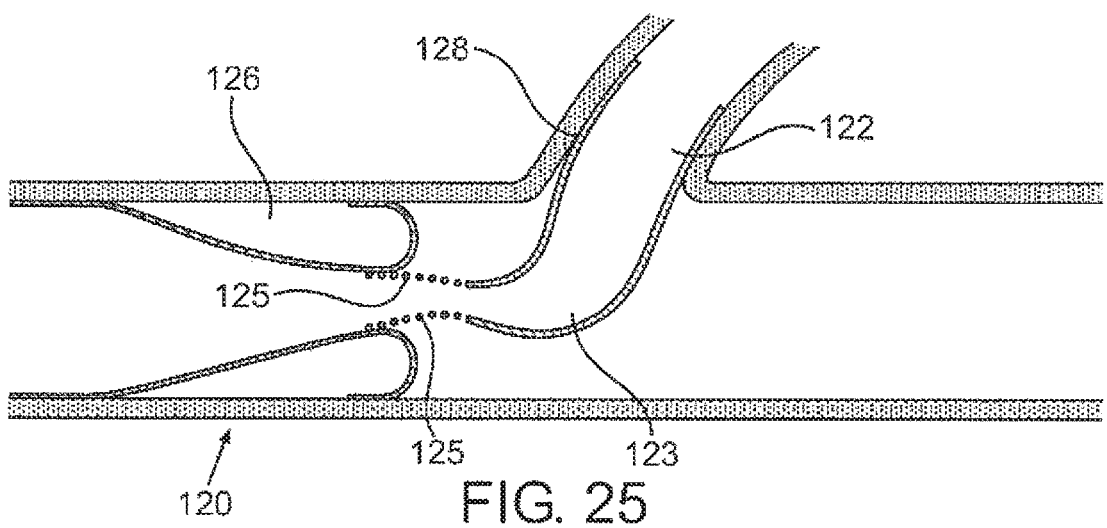
FIG. 25 is a schematic view of a fluid flow modulator, in accordance with another embodiment of the present invention, with an upstream flow accelerator that has a portion which is not in-line with a downstream flow decelerator, but is instead tilted relative thereto and which may be installed in a branch lumen.

With respect to FIG. 25, flow modulator 120 is described and includes upstream component 122 with outlet 123 and downstream component 126. Upstream component 122 has first portion 128 which is not in-line with downstream component 126, but is instead tilted relative thereto and installed in a branch lumen. Outlet 123 may be directed to the center of the inlet to downstream component 126 and may be coupled with support 125 to a portion of downstream component 126, for example, to center the nozzle with respect to the inlet. Alternatively, a separate stent structure (that does not hinder flow) may be used to support outlet 123.

Figure 26:
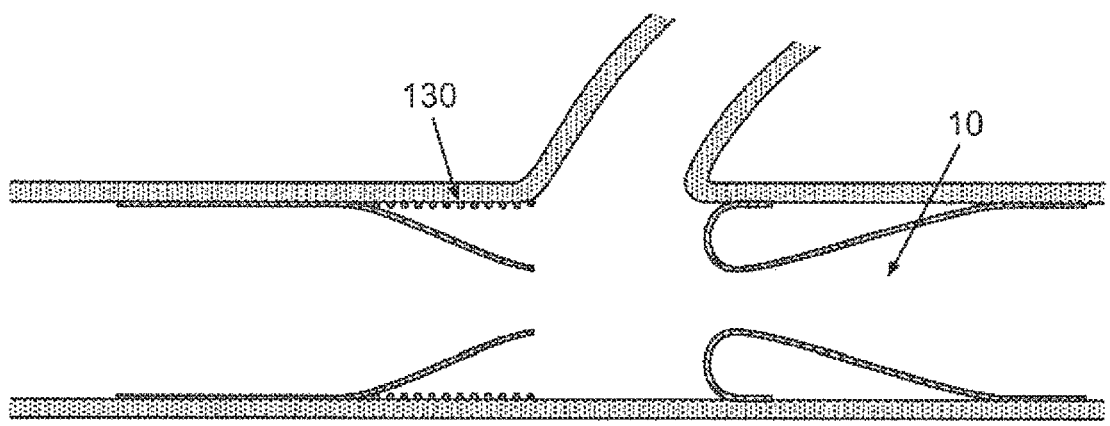
FIG. 26 is a schematic view of a lumen support member used with a fluid flow modulator, in accordance with another embodiment of the present invention.

Referring now to FIG. 26, lumen support member 130 is described, which may be a stent body, that helps support the body lumen from collapsing inwards during reduced pressure.

Figure 27:
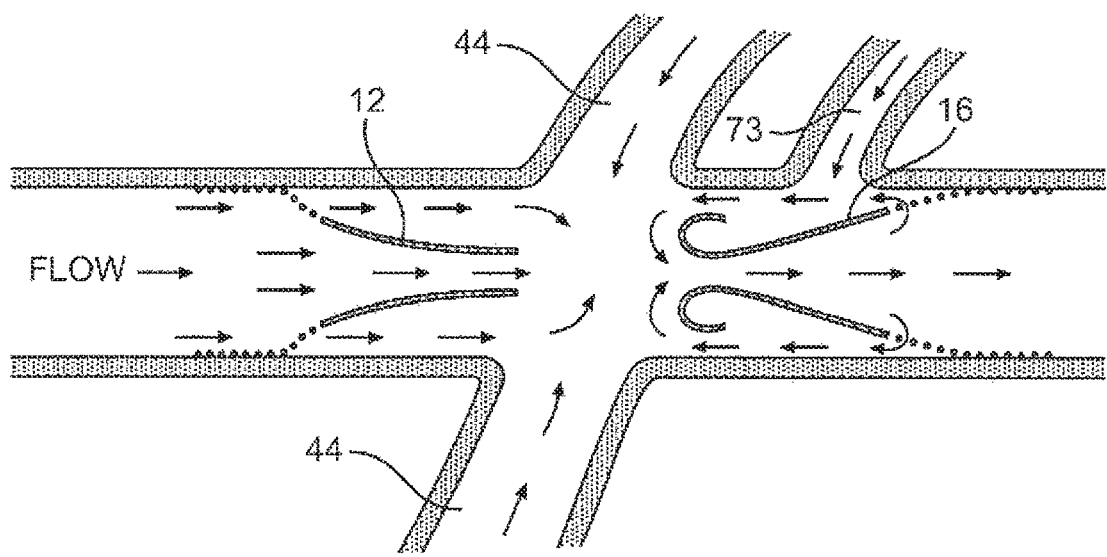
FIG. 27 is a schematic view of a fluid flow modulator, in accordance with another embodiment of the present invention, in which the upstream flow accelerator and/or downstream flow decelerator may not seal against the inner contour of the body lumen.

In FIG. 27, which may be implemented in any of the embodiments described herein, upstream component 12 and/or downstream component 16 may be configured not seal against an inner contour of the body lumen, but instead may be spaced from the inner contour of the body lumen. This arrangement prevents blocking flow from side branch 73. Although this configuration may create pressure losses, it still reduces pressure as compared to just using a nozzle, and it may improve flow out of the body lumen, such as improving flow out of a vein.

Figure 28:
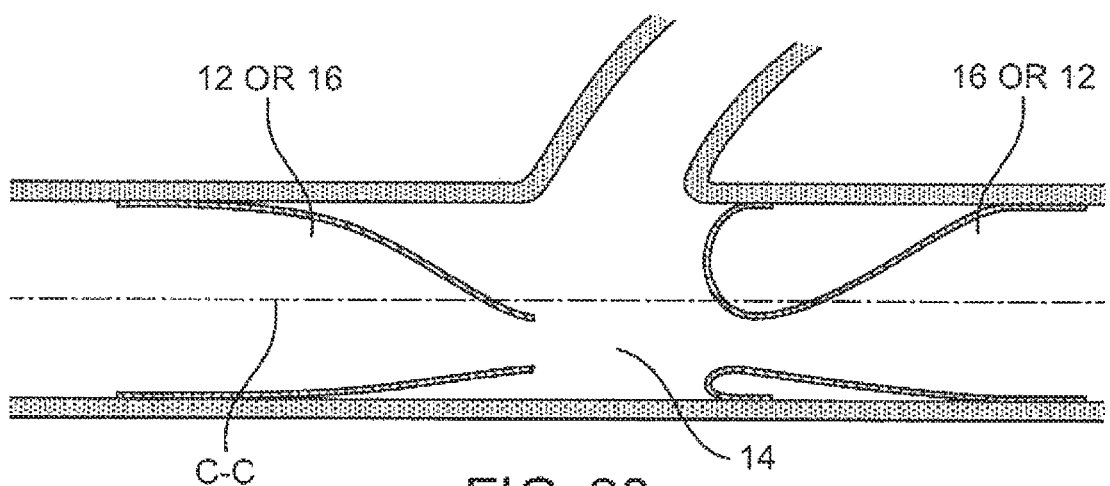
FIG. 28 is a schematic view of an asymmetric transition between the upstream flow accelerator and the downstream flow decelerator, in accordance with another embodiment of the present invention.

FIG. 28 illustrates that the transition between upstream component 12 to downstream component 16 (the region of gap 14) may be off-center from the center line C-C of the body lumen. In such an embodiment, the transition between upstream component 12 to downstream component 16 is asymmetric with respect to the center line of the body lumen. For example, this configuration may be used advantageously if there is only one side branch—the asymmetry will favor flow from the side branch; if there are two side branches, the asymmetry will favor flow from one of the side branches.

Figure 29A:
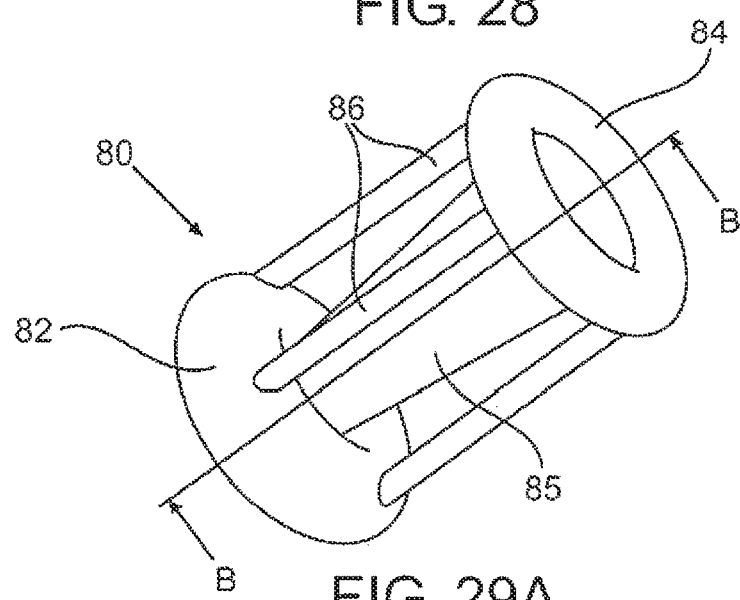
Figure 29B:
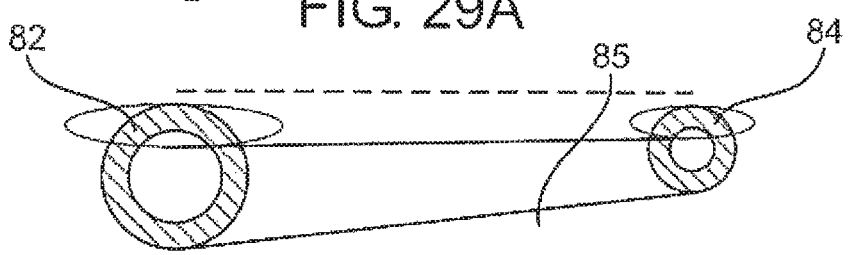
Figure 29B:
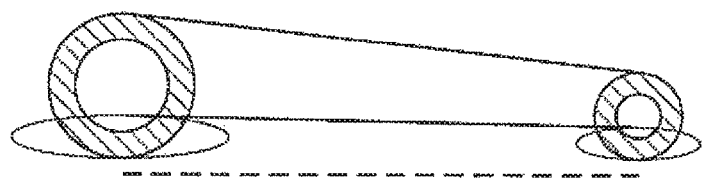

Referring now to FIGS. 29A and 29B, upstream component or downstream component 80 of a further alternative embodiment is described, in which the shape of the component is adjustable. Upstream component and downstream component 80 may be combined to create a nozzle/diffuser configuration with a gap therebetween similar to the other structures described throughout this disclosure. In particular, accelerator or decelerator 80 may include one or more inflatable members, such as end faces 82 and 84, coupled by intermediate member 85, such as inflatable balloons or bladders, which can be inflated or deflated by introducing or extracting fluid into or from inflatable members 82 and 84 (connected to a suitable fluid source, such as water, saline, air, etc.) Intermediate member 85 may be a cover material and/or may be pre-shaped (e.g., a cylindrical shape like a stent), thereby creating radial force on inflatable members 82 and/or 84 to create better sealing. Changing the size of inflatable members 82 and 84 adjusts the flow characteristics through the device, such as the degree of divergence or convergence. Inflatable members 82 and 84 may be connected by longitudinal members 86, which may also be inflatable and thus changeable in size, such as changeable in length or thickness.

Device 80 may be deployed in the deflated state and then inflated in-situ. If the upstream component and the downstream component are combined into one device, the respective inflatable members may be inflated/deflated simultaneously using a common lumen in a catheter or individually using a multi-lumen catheter. After the patient has reached a stable condition, the device may be deflated or inflated as needed to adapt to changing conditions. The device also may be deflated for removal from the body. A reservoir of fluid may be implanted with the device for use in maintaining inflation of the device after installation in the body. The device may be held against the inner walls of the body lumen or may be separated from them, as described above for other embodiments. Flow modulator 10 may be compressed for delivery (e.g., percutaneous delivery within a delivery sheath) and expanded upon deployment (e.g., self-expanding upon exposure from the distal end of the delivery sheath or balloon expandable).

Figure 30:
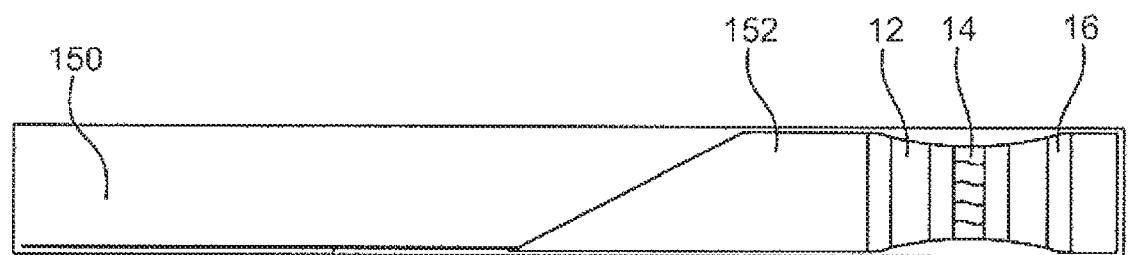
FIGS. 30-34 are schematic views of fluid flow modulators, in accordance with embodiments of the present invention, shown in delivery and retrieval-type configurations.

Referring now to FIG. 30, flow modulator 10 is depicted compressed for delivery within sheath 150. Flow modulator 10 may be coupled to transition portion 152 and/or wire 154 to facilitate delivery to the body lumen and/or retrieval from the body lumen. Transition portion 152 illustratively has a non-concentric cone shape to facilitate compression into sheath 150 and is coupled to upstream component 12, although it also may be coupled to downstream component 16. Wire 154 is coupled to transition portion.

Figure 31A:
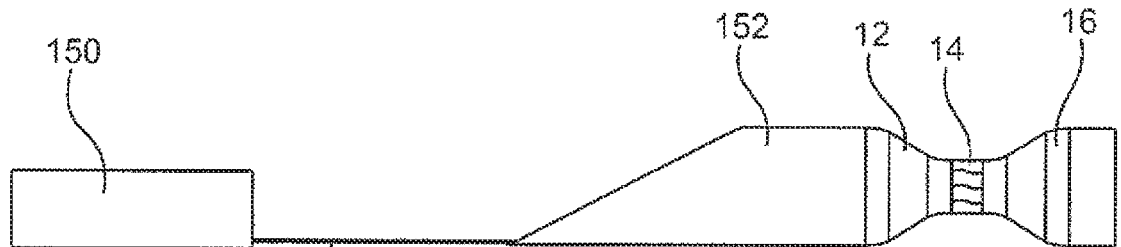
Figure 31B:

In FIGS. 31A and 31B, flow modulator 10 is depicted in the expanded, deployed configuration outside of sheath 150. Flow modulator 10 may transition to the expanded, deployed configuration when exposed past the distal end of sheath 150. For example, sheath 150 may be pulled proximally against a fixed stopper in sheath 150 to unsheath flow modulator 10 at a target location within a body lumen, e.g., where the renal veins intersect with the inferior vena cava.

Flow modulator 10 may be retrieved from the body lumen (e.g., inferior vena cava). For example, a sheath may be threaded over wire 154 and wire 154 may be fixed in place (e.g., ex vivo fixation of the proximal end of the wire). Then, the sheath is pushed against transition portion 152 to compress flow modulator 10 within the sheath. Flow modulator 10 and the sheath are then removed from the patient.

Figure 32:
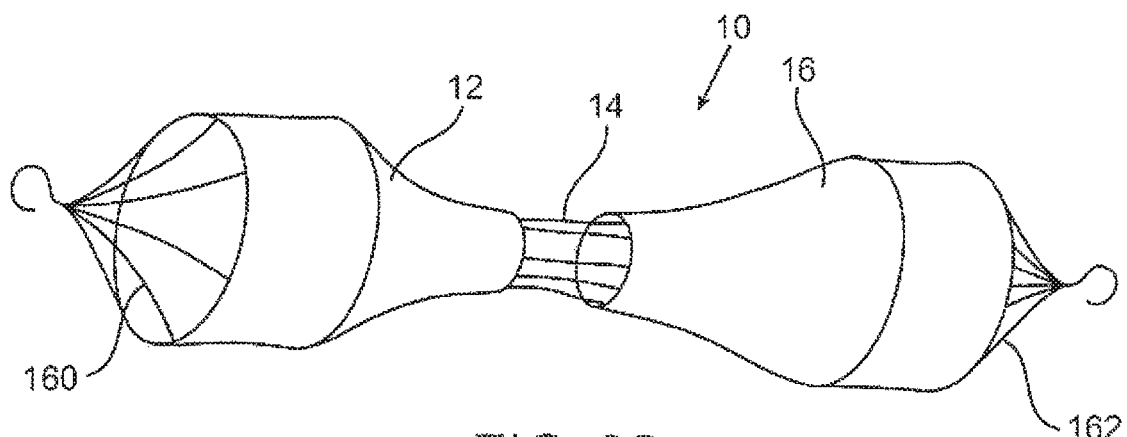

Referring now to FIG. 32, a further alternative embodiment of flow modulator 10 is describe. Flow modulator 10 is similar to flow modulator 10 of FIG. 3A, although the flow modulator 10 of FIG. 32 includes retrieval mechanism 160. Retrieval mechanism 160 may be coupled to the proximal end of upstream component 12. In this manner a retrieval device, e.g., hook 166, may be coupled to retrieval mechanism 160 to pull retrieval mechanism towards sheath 164 to compress flow modulator 10 into sheath 164 for retrieval. For example, retrieval mechanism 160 may be configured like a snare with a plurality of arms coupled to the end of upstream component 12 and coupled together near the center of the flow path within upstream component 12. Flow component 10 may be implanted with retrieval mechanism 160 coupled thereon or retrieval mechanism 160 may be coupled to flow modulator 10 during the retrieval process.

Flow modulator 10 of FIG. 32 also includes retrieval mechanism 162 at an opposing end of flow modulator, e.g., coupled to the end of downstream component 16. Retrieval mechanism 162 works in the same manner as retrieval mechanism 160. Use of two retrieval mechanisms may be particularly helpful when flow modulator 10 is formed from a braided structure, as the diameter of the structure decreases as the braid is lengthened. Retrieval mechanisms 160 and/or 162 may also be used for partial retrieval. For example, retrieval mechanism 160 and/162 may be pulled (simultaneously or at different times) in a direction(s) away gap 14 to partially or fully reduce the diameter of flow modulator 10 within a body lumen. Such reduction would allow for wash-out of any stagnant flow zones created adjacent to flow modulator 10. Flow modulator 10 could then be fully removed, repositioned within the body lumen and expanded, or expanded in the prior deployment location within the body lumen.

Figure 33A:
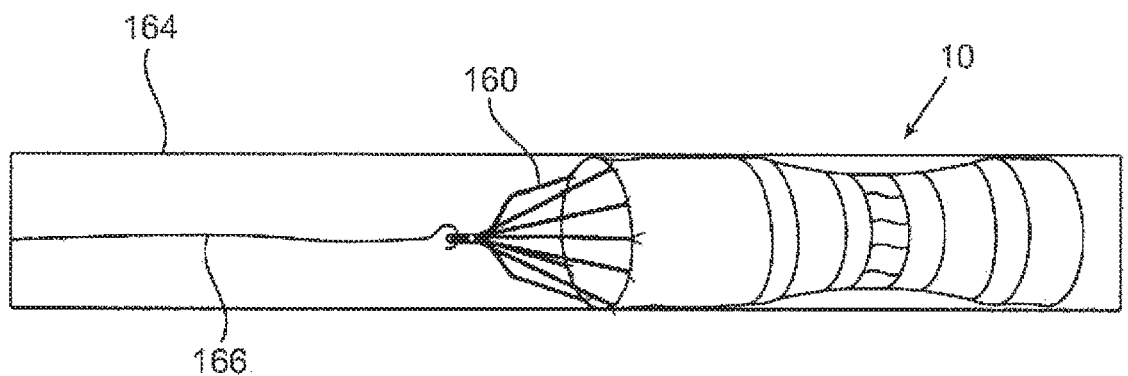
Figure 33B:
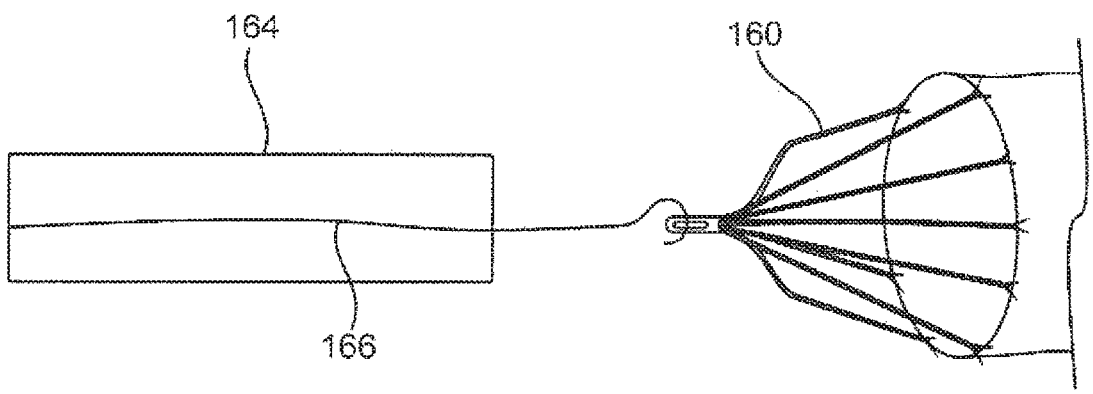

FIGS. 33A and 33B show hook 166 coupled to retrieval mechanism 160 in the compressed state within sheath 164 and in the expanded state outside of sheath 164.

Figure 34:
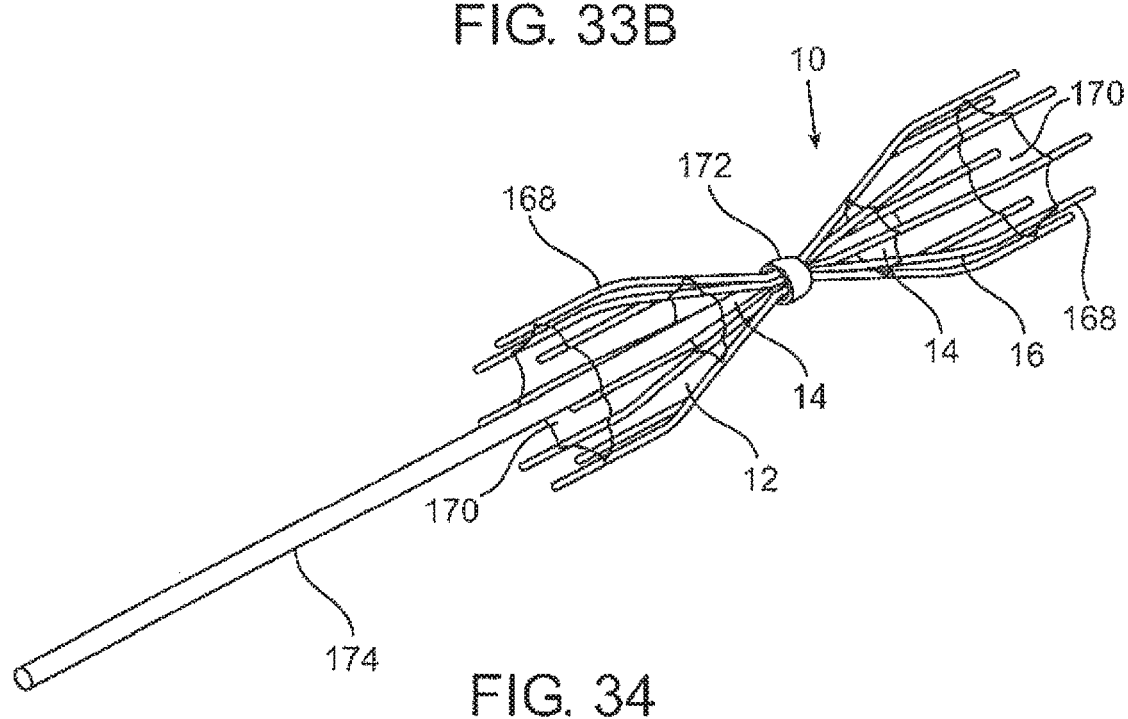

Referring now to FIG. 34, flow modulator 10 of a further alternative embodiment is described. Flow modulator 10 is similar to flow modulator 10 of FIG. 3A, but further includes ring 172. In this embodiment, frame 168 is formed from a plurality of ribs and defines upstream component 12 and downstream component 16. Frame 168 may be formed from a shape memory material such as shape memory metal. Frame 168 is coated with biocompatible material 170 at upstream component 12 and downstream component 16 to define the flow channels and the uncoated portion of frame 168 therebetween defines gap 14. Ring 172 is disposed around a portion of frame 168 and maintains the portion disposed therein in a compressed configuration. For example, in the deployed state down in FIG. 34, ring 172 is disposed around the portion of fluid modulator between upstream component 12 and downstream component 16 to cause frame 168 to form a converging cross-sectional flow area at upstream component 12 and a diverging cross-sectional flow area at downstream component 16. Ring 172 is configured to move along frame 168 to transition the portions of frame 168 disposed within ring 172 from an expanded state to a contracted state. Shaft 174 may be coupled to ring 172 such that movement of shaft 174 moves ring 172 along frame 168.

Flow modulator 10 is deliverable in a compressed state within a sheath to a target location within a body lumen. Once suitably positioned, flow modulator 10 is exposed from the sheath (e.g., by pulling the sheath proximally while flow modulator 10 remains in place) and flow modulator 10 self-expands to the deployed configuration. Flow modulator 10 may be partially retrieved (e.g., compressed to allow for washing) and/or fully retrieved by moving ring 172 proximally (e.g., by pulling shaft 174 proximally) to compress upstream component 12 or downstream component 16 to a diameter suitable for insertion within a sheath. The remaining portion of flow modulator 10 may then be compressed within the sheath and removed from the body via the sheath.

Figure 35:
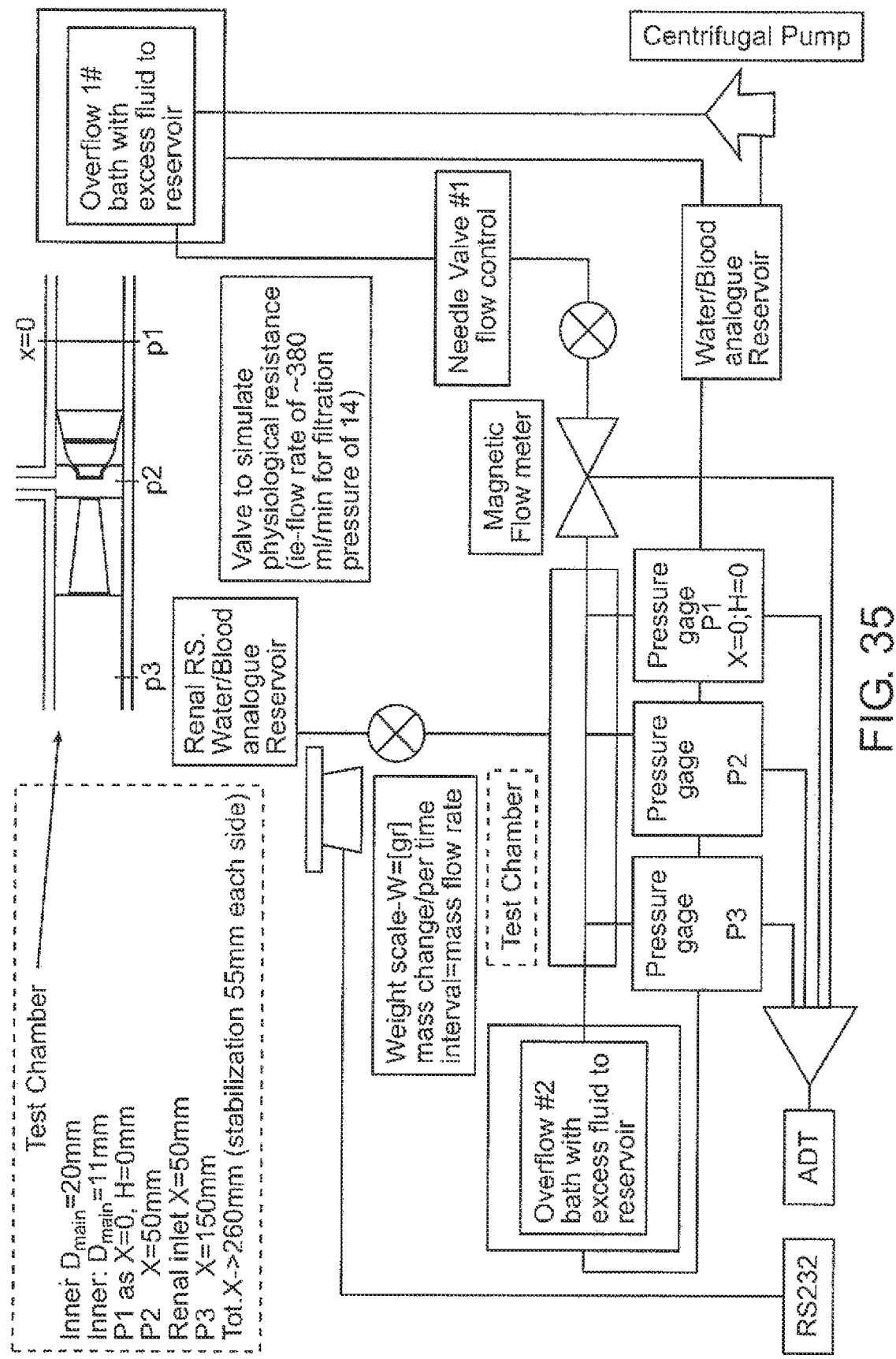
FIGS. 35-37E are the results from a bench top test used for determining preferred configurations for flow modulators constructed in accordance with the present invention.

FIG. 35 illustrates a bench test used for determining preferred configurations of flow modulators constructed in accordance with the present invention. In the bench test, a flow modulator was placed in a main lumen (to simulate the inferior vena cava) such that the gap was positioned at a branch lumen (to simulate a renal vein). The bench model utilized a constant steady flow in the main branch and was connected to an overflow bath to maintain constant physiological pressure. Water was used for the fluid and blood analogue was used to verify the trends. A side branch pipe with a controlled resistance was connected to a lifted reservoir (to simulate renal filtration pressure). The resistance in the side branch was fixed in a rate to create a normal renal flow with a normal net filtration pressure. As a result, fluid flow was low when the pressure gradient between the renal bath to the main lumen was smaller.

Three pressure sensors (shown as P1, P2, and P3 in FIG. 35) were connected to the simulated IVC (upstream to the side branch, at the side branch level, and downstream to side branch). A magnetic flow sensor was used to measure IVC flow. Renal flow was measured with a digital weight scale with a computer interface via rs232. Thus, mass flow rate can be measured (or flow rate since the density can be calculated) without creating additional pressure loss.

Figure 36:
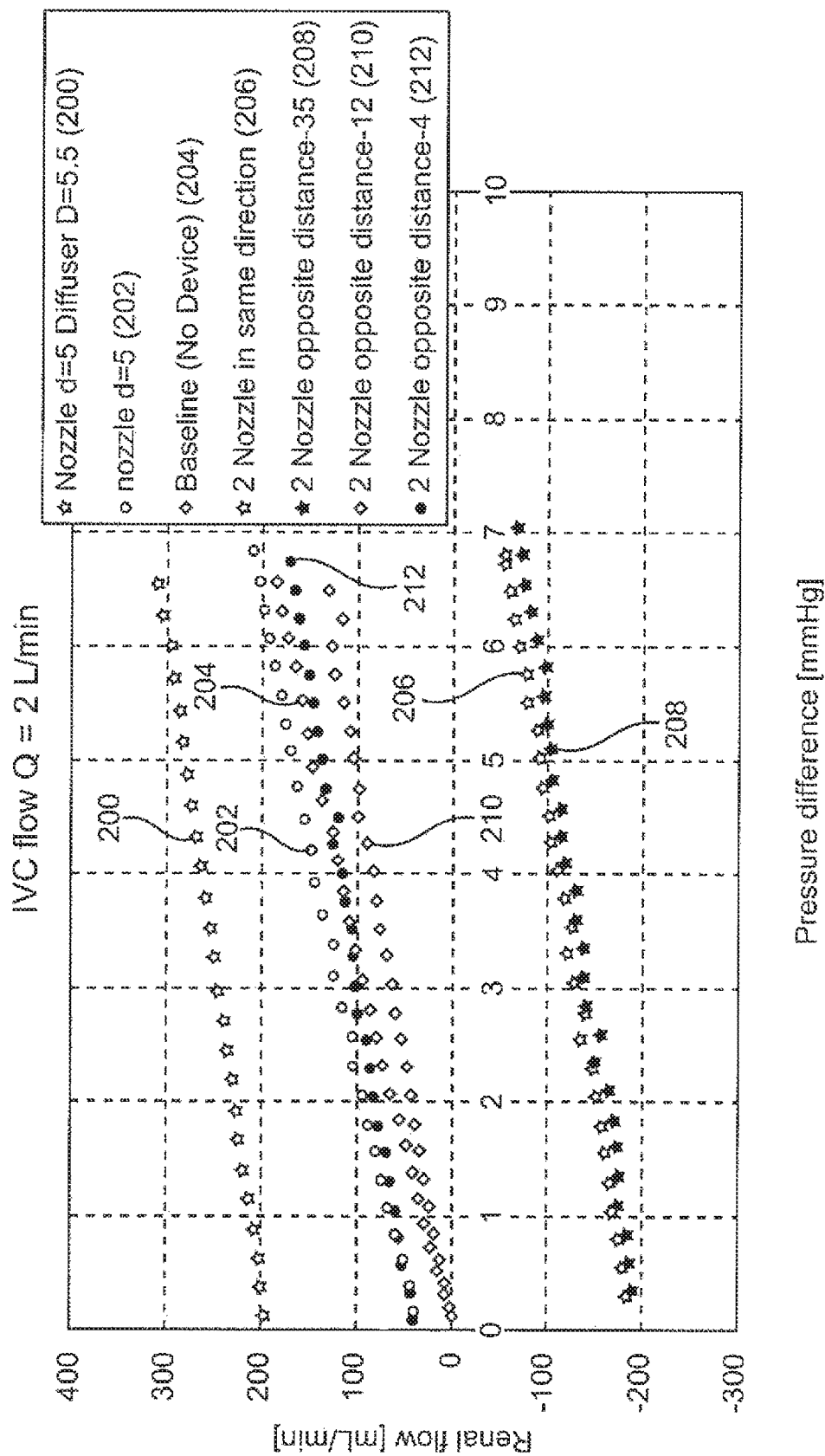
Figure 37A:
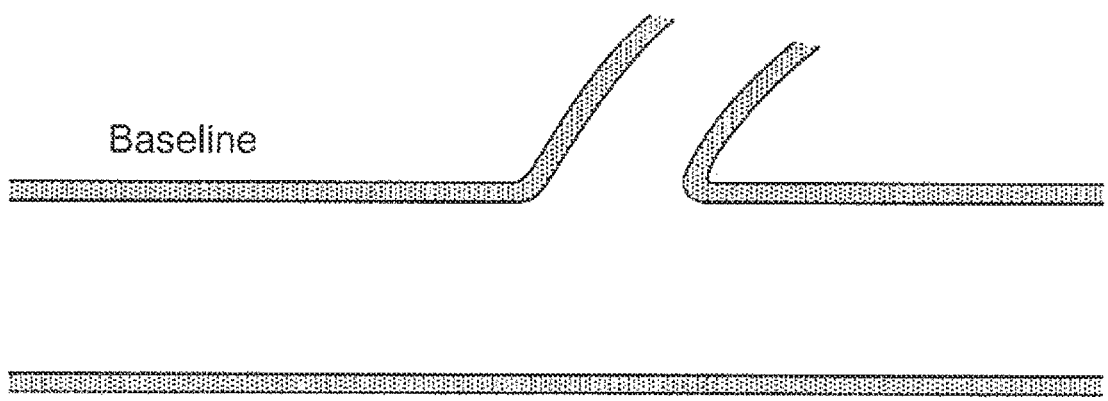
Figure 37B:
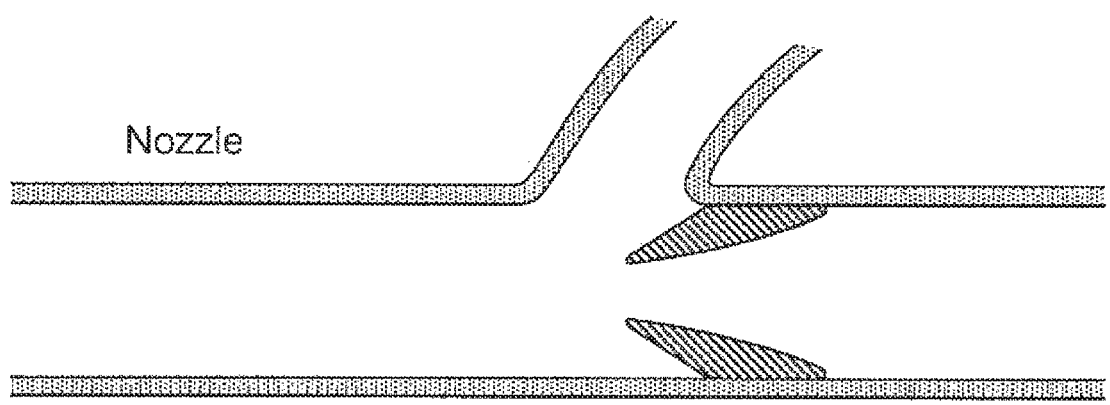
Figure 37C:
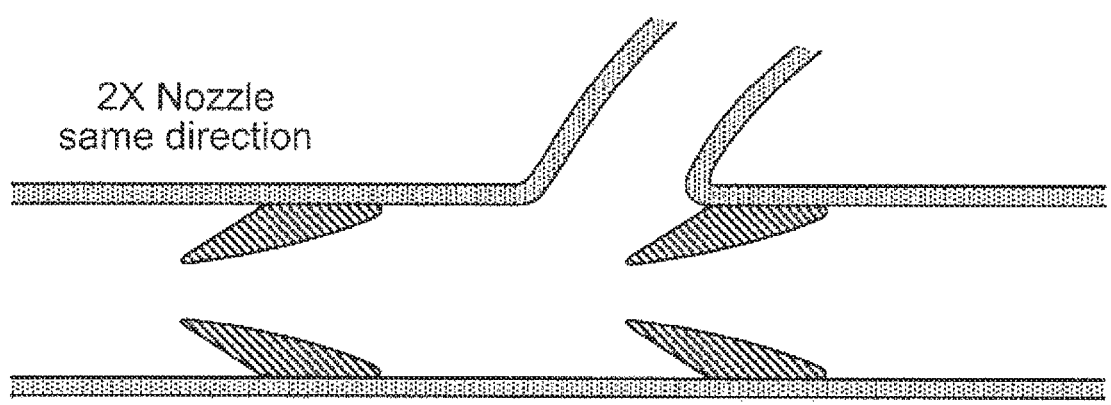
Figure 37D:
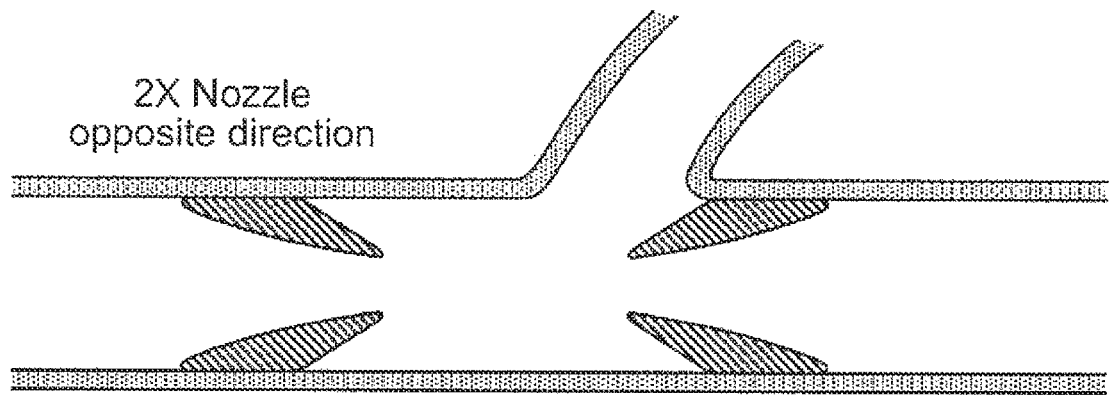
Figure 37E:
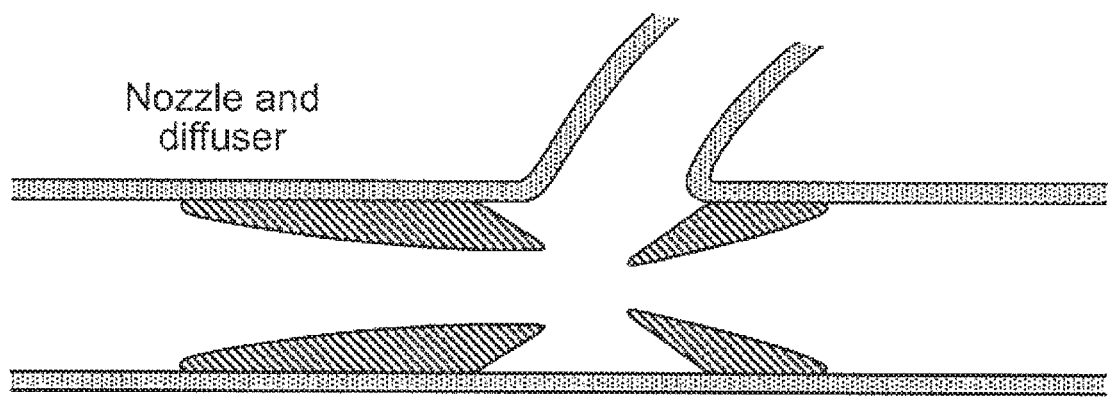

FIG. 36 is a graph showing the results for one representative IVC flow rate (2 liters per minute (L/min)). The graph shows renal flow in mL/min versus pressure difference in mmHg for various configurations shown in FIGS. 37A-37E. Data points 200 are for a nozzle and diffuser configuration (shown in FIG. 37E) based on the flow modulator principles described herein. In this example, the upstream nozzle has an outlet inner diameter of 5 mm and the downstream diffuser has an entry inner diameter of 5.5 mm. As shown in FIG. 36, the renal flow is highest for this configuration and the table below shows that this nozzle and diffuser configuration create significantly less pressure loss than all other configurations. Data points 202 are for a single nozzle configuration (shown in FIG. 37B). The same upstream nozzle was used as the upstream nozzle in the nozzle and diffuser configuration.

Still referring to FIG. 36, the renal flow is lower than the nozzle/diffuser configuration, but higher than the other configurations and the pressure loss of 11 mmHg shown in the table below is significantly larger than the pressure loss of the nozzle and diffuser configuration. Data points 204 are for baseline, meaning no device is used (shown in FIG. 37A). In FIG. 36, only the inventive nozzle and diffuser configuration of the present invention is significantly better than baseline. Data points 206 are for two nozzles in the same direction (shown in FIG. 37C). As shown in FIG. 36, renal flow is actually negative, which would send blood flow in the renal veins in the wrong direction. In addition, the table below confirms the pressure loss of 22 mmHg is high. The same upstream nozzle was used as above and the downstream nozzle has an outlet inner diameter of 5 mm. Data points 208, 210, and 212 are for two nozzles in opposite directions for distances between the outlet of the upstream nozzle and the inlet of the downstream nozzle of 35 mm (shown in FIG. 37D), 12 mm, and 4 mm, respectively. The same upstream nozzle was used as above and the downstream nozzle has an inlet inner diameter of 5 mm. For data points 208 where the distance is 35 mm, similar to data points 206, renal flow is actually negative, which would send blood flow in the renal veins in the wrong direction. In addition, the table below confirms the pressure loss of 22 mmHg is high. For data points 210 and 212, the renal flow is around or worse than baseline and the pressure loss is high at 14 mmHg

| Configuration | Pressure loss [mmHg] |
| --- | --- |
| Nozzle and diffuser | 5 |
| Nozzle | 11 |
| 2 Nozzle same direction | 22 |

-continued

| Configuration | Pressure loss [mmHg] |
|---|---|
| 2 Nozzle opposite direction distance-35 mm | 22 |
| 2 Nozzle opposite direction distance-12 mm | 14 |
| 2 Nozzle opposite direction distance-4 mm | 14 |

Applicant has discovered that using a maximum distance between the outlet of the upstream component and the entry to the downstream component will improve flow rates in the branched vessel(s) with relatively low pressure loss. A distance too great will create a significant pressure loss that actually sends flow in the wrong direction in the renal vein(s). In addition, other structural characteristics of the downstream component improve renal flow with low pressure loss such as a greater inner diameter at the entry of the downstream component than the inner diameter at the outlet of the upstream component, a greater length of the diverging area of the downstream component than the length of the converging area of the upstream component, and/or a lesser average angle of divergence of the downstream component than the average angle of convergence of the upstream component.

Figure 38A:
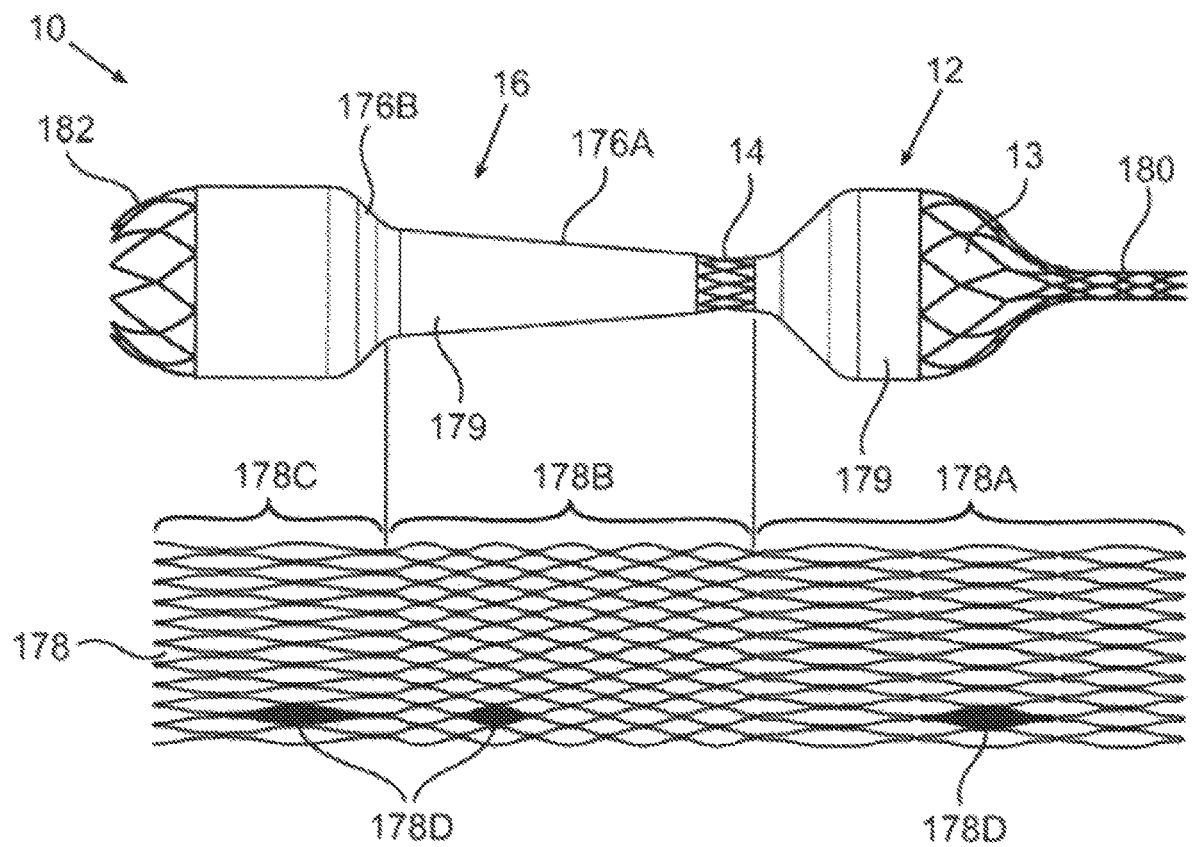
FIG. 38A is a side view of a fluid flow modulator, in accordance with another embodiment of the present invention, having a frame structure comprising a plurality of cells shown over the frame structure (prior to shaping of the frame)

Referring now to FIG. 38A, another embodiment of flow modulator 10 of the present invention is described. In this embodiment, flow modulator 10 includes an exemplary frame structure as cut and flattened to show the frame cutting pattern. FIG. 38A shares many characteristics as set forth in FIGS. 1 and 3A, and like elements are designated by like numerals. In this embodiment, downstream component 16 has first diverging portion 176A and second diverging portion 176B. First diverging portion 176A is upstream from second diverging portion 176B. The average angle of divergence of second diverging portion 176B preferably is greater than the average angle of divergence of first diverging portion 176A.

Flow modulator 10 of the embodiment of FIG. 38A preferably is formed from one or more frames and may be coated with one or more biocompatible materials as described above. Illustratively, upstream component 12 and downstream component 16 are defined by frame 178. Frame 178 is preferably formed from a metal tube that is laser cut to define a plurality of cells and then processed (e.g., heated) to form the shape of flow modulator 10. Upstream component 12 is illustratively formed from first plurality of cells 178A whereas downstream component 16 is formed from two different configurations of cells. First diverging portion 176A of downstream component 16 may be formed from second plurality of cells 178B and second diverging portion 176B may be formed from third plurality of cells 178C. Second plurality of cells 178B preferably is disposed between first plurality of cells 178A and third plurality of cells 178C. The void space may be the area of the cell defined by the struts of the frame. For example, the struts may define close-looped shapes therewithin, such as ellipses or diamonds or a combination thereof.

Solely for clarity purposes, one void space 178D from each of first plurality of cells 178A of upstream component 12, second plurality of cells 178B of first diverging portion 176A, and third plurality of cells 178B of second diverging portion 176B is colored in the flattened portion of FIG. 38A to show the respective void space areas within the cell. In accordance with one aspect of the present invention, the average void space area of first plurality of cells 178A preferably is larger than the average void space area of second plurality of cells 178B, and may be substantially identical to the average void space area of third plurality of cells 178C. The larger void space area of first plurality of cells 178A creates a more flexible structure than second plurality of cells 178B. Thus, frame 178 may be a three-part stent forming a flexible/rigid/flexible configuration.

Advantageously, after implantation, the flexible regions can change in diameter responsive to changes in vessel diameter while the more rigid portion of the stent structure remains constant. For example, the maximum outer diameter of upstream component 12 and downstream component 10 may change in diameter responsive to changes in vessel diameter while the shape of the intermediate section (e.g., first diverging portion 176A) of flow modulator 10 does not change. In this manner, the angle of divergence of first diverging portion 176A may remain constant even though the size of the vessel changes. The change in diameter in the vessel may be measured, e.g., with one or more sensors on flow modulator and/or using imaging guidance such as fluoroscopy, to evaluate the diameter change over time.

As an additional or alternative way to enhance rigidity of the intermediate section of flow modulator 10, the struts of frame 178 may be wider and/or thicker than the struts of frame 178 at the more flexible portions. For example, the struts of frame 178 may be wider and/or thicker at the section forming second plurality of cells 178B than at the sections forming first plurality of cells 178A and/or third plurality of cells 178C. Additionally or alternatively, the lengths of the cells formed by the struts of frame 178 may be shortened and/or the number of cells for a given length of frame 178 may be decreased to increase rigidity.

Figure 38B:
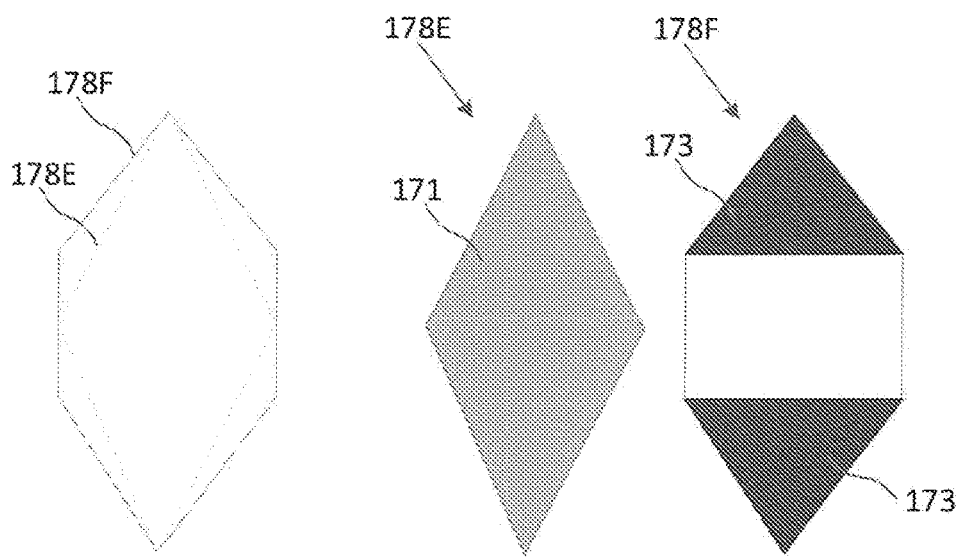
FIG. 38B illustrates various void space shapes having varying flexibilities in accordance with one aspect of the present invention.

In accordance with another aspect of the present invention, the relative flexibility between the portions of the frame may be selected using different shaped cells. This is yet another manner to form a three-part stent in a flexible/rigid/flexible configuration. For example, the flexibility of first plurality of cells 178A and third plurality of cells 178C, and the rigidity of second plurality of cells 178B, may be selected based on the shape of the respective void space defined by the struts of frame 178 (e.g., flexibly-shaped cells/rigidly-shaped cells/flexibly-shaped cells in the frame). For example, as shown in FIG. 38B, void space 178E of the cells of first plurality of cells 178A and third plurality of cells 178C may have a diamond shape, and void space 178F of the cells of second plurality of cells 178B may have a hexagonal shape (e.g., elongated hexagonal shape). As shown in FIG. 38B, void space 178F has a larger overall void space area than void space 178E; however, the cells having void space 178F are stronger than the cells having void space 178E. This is because void space 178E has a larger overall working area 171 than working area 173 of void space 178F. In some configurations, the working area of a cell is the area of the cell defined by the angled portions of the struts of the frame, i.e., not including the area of the cell defined by the portions of the struts that are aligned with the longitudinal axis of frame 178. As shown in FIG. 38B, working area 171 of void space 178E is larger than the total working area 173 of void space 178F, and thus the cells having void space 178E are more flexible than the cells having void space 178F, and the cells having void space 178F are more rigid than the cells having void space 178E. Accordingly, the plurality of cells defining gap 14, e.g., second plurality of cells 178B, may have an overall larger average void space area while maintaining desired rigidity, such that a gap may be formed larger within a respective cell, thereby increasing the amount of flow that can be entrained through the gap than could be through a gap within a smaller diamond shaped cell.

Referring again to FIG. 38A, frame 178 may be coated with biocompatible material 179 at upstream component 12 and downstream component 16 and the uncoated portion of frame 178 therebetween defines gap 14. The plurality of cells at the uncoated portion of frame 178 at inlet 13 may optionally serve as a filter, e.g., against thrombus and/or emboli in blood. Flow modulator 10 also may include constricted section 180 to allow flow modulator 10 to remain coupled to a delivery system. Constricted section 180 may be at the upstream-most end of flow modulator 10. Flow modulator 10 also may include atraumatic end 182 to prevent vessel damage and flare out during device crimping, and to give the distal end integrity. Atraumatic end 182 curves inward away from the body vessel inner wall and may be at the downstream-most end of flow modulator 10. As illustrated, frame 178 may be coated with biocompatible material 179 at a portion of upstream component 12 (e.g., the converging portion and/or the constant diameter portion), but may be a bare metal frame at other portions (e.g., upstream from the converging portion and/or constricted section 180) and may be coated with biocompatible material at a portion of downstream component 16 (e.g., first diverging portion 176A downstream of gap 14, second diverging portion 176B, and/or constant diameter portion), but may be a bare metal frame at other portions (e.g., gap 14 and/or atraumatic end 182).

Figure 38C:
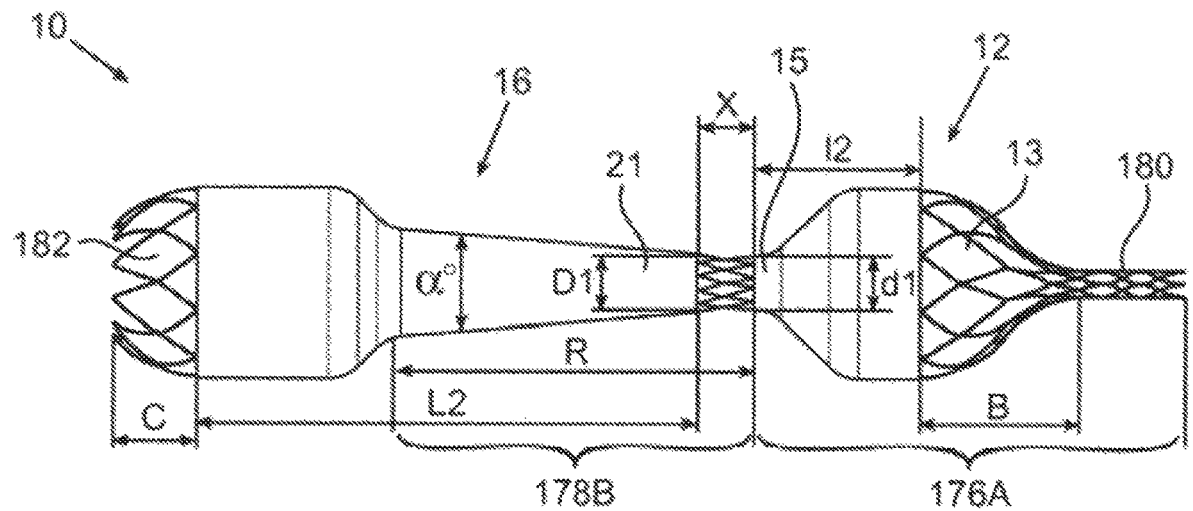
FIG. 38C is a side view of the fluid flow modulator of FIG. 38A.

Referring now to FIG. 38C, flow modulator 10 of FIG. 38A is shown with symbols depicting dimensions in accordance with a preferred embodiment. d1 is the diameter of outlet 15 of upstream component 12. d1 is selected to create a jet velocity for a given device resistance. d1 may be in a range from 4-7 mm. l2 is the overall length of upstream component 12 and may be in a range from 15-35 mm. x is the distance from outlet 15 of upstream component 12 to entry 21 of downstream component. Distance x preferably is selected in a range from 2-20 mm L2 is the overall length of downstream component 16. L2 is preferably greater than 40 because a diverging shape creates a higher pressure loss than a converging shape. The ratio of L2:l2 may be from 1:1 to 3:1. D1 is the diameter at entry 21 of downstream component 16 and is preferably larger than d1. D1 is preferably =(d1+2*X*tan(A/2)). Thus, the cross-sectional flow area at outlet 15 of upstream component 12 is less than the cross-sectional flow area at entry 21 of downstream component 16. D1 is selected to receive all the fluid jetted from outlet 15. The ratio of D1:d1 may be from 1:1 to 2:1.

In addition, D1 should be greater for larger distances x to ensure receipt of the fluid jetted from upstream component 12. A is the average angle of divergence in first diverging portion 176A of downstream component 16 and may be in a range from 5-20 degrees. Preferably, the angle of divergence in downstream component 16 is less than the angle of convergence in upstream component 12, as illustrated. Such structure is expected to prevent pressure loss. B is the length between inlet 13 of upstream component 12 and constricted section 180. B may be in a range from 12-45 mm. C is the length of exposed atraumatic end 182 and may be in a range from 3-20 mm. R is the length of rigid second plurality of cells 178B. R is preferably <(2/3*l2+x+2/3*L2). R preferably starts±15 mm from the nozzle orifice.

Figure 38D:
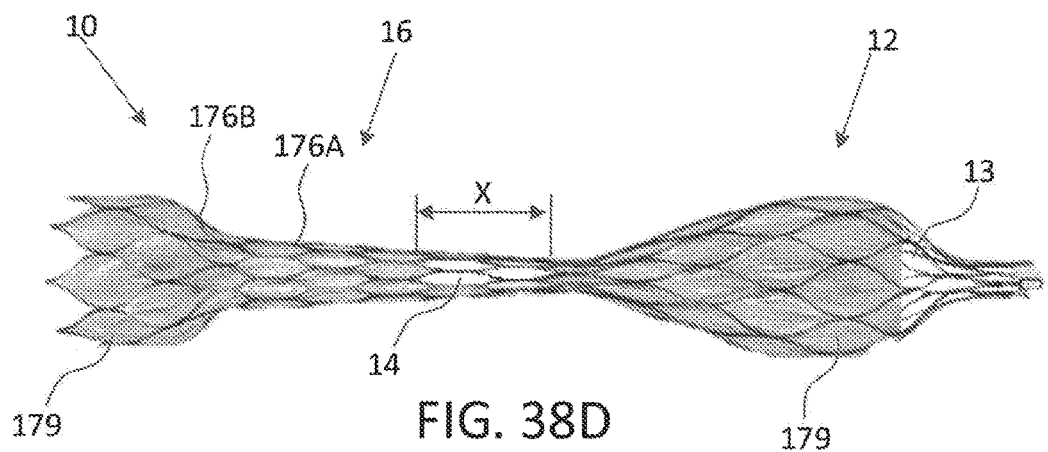
FIG. 38D is a side view of a fluid flow modulator, in accordance with yet another embodiment of the present invention, having a frame structure coated with a biocompatible material.

Referring now to FIG. 38D, flow modulator 10 constructed in accordance with the principles of the present invention is provided. Specifically, FIG. 38D is a side view of flow modulator 10 having upstream component 12 and downstream component 16 having first diverging portion 176A and second diverging portion 176B. As shown in FIG. 38D, the frame of flow modulator 10 may be only partially covered with biocompatible material 179 such that the plurality of cells at inlet 13 and a plurality of cells at gap 14 remain uncoated. Specifically, gap 14 may be defined by the uncoated plurality of cells between upstream component 12 and downstream component 16. For example, the frame of flow modulator 10 may initially be entirely coated with biocompatible material 179, and then selected portions of the coating may be removed, e.g., via cutting, melting, laser, chemical, etc., to form gap 14. Alternatively, the frame of flow modulator 10 may be selectively coated such that portions that are not coated define gap 14 during the coating process. Moreover, a pattern of the plurality of uncoated cells of gap 14 may be selected to improve entrainment properties of fluid through gap 14 when in use in a blood vessel.

For example, FIGS. 38E-38H illustrate various frame structures having second plurality of cells 178B with various configurations of uncoated portions of biocompatible material denoted by the shaded void space areas. In some configurations, these uncoated portions define a plurality of longitudinally extending openings radially spaced around the entrainment region. Further, as described above and as shown in FIGS. 38E-38I, second plurality of cells 178B may include larger, yet more rigid cell shapes (e.g., elongated hexagonal shaped cells), and first plurality of cells 178A and third plurality of cells 178C may include smaller, yet more flexible cell shapes (e.g., diamond shaped cells). As will be understood by a person having ordinary skill in the art, the flow modulator formed by the frames illustrated in FIGS. 38E-I may include any of the designs described herein to provide the desired flexible/rigid/flexible configuration.

Figure 38E:
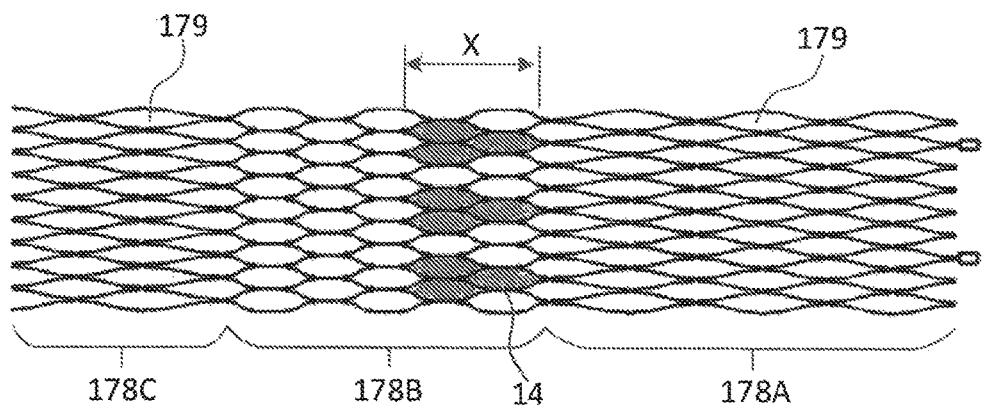
FIGS. 38E-38H illustrate various frame structures comprising a plurality of cells having various configurations of uncoated portions of biocompatible material.
Figure 38F:
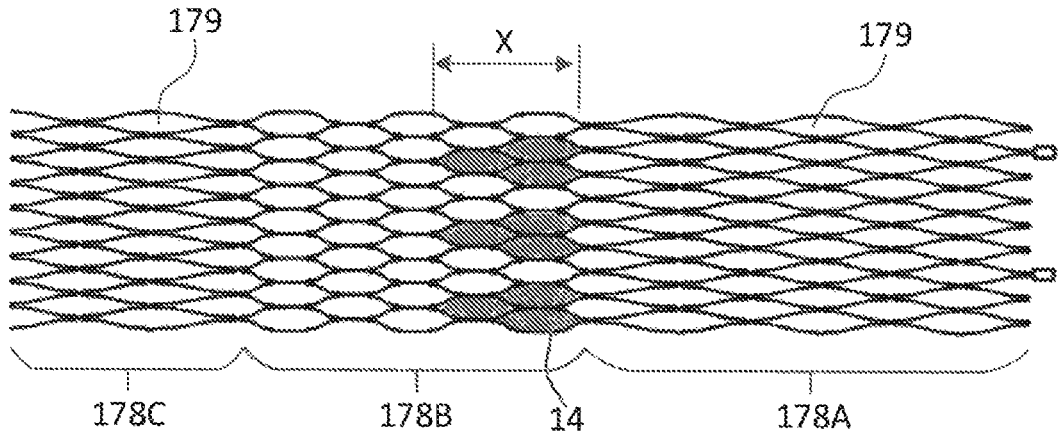
Figure 38G:
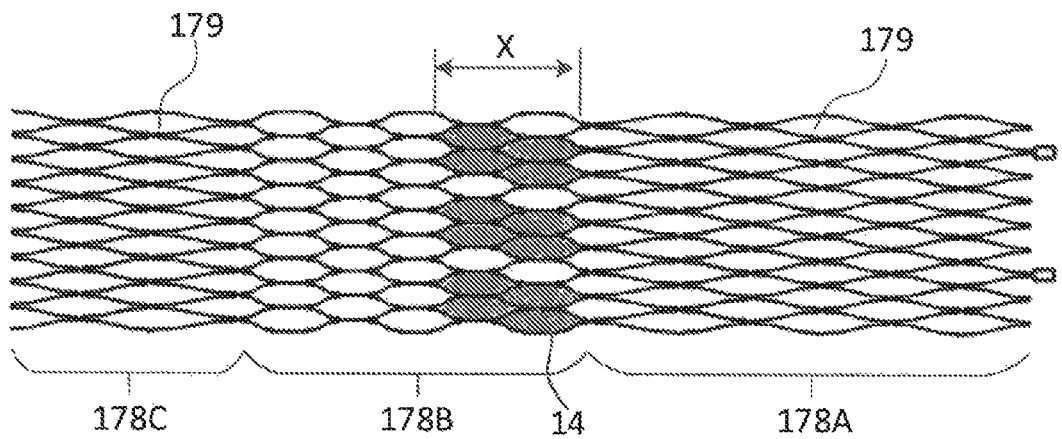
Figure 38H:
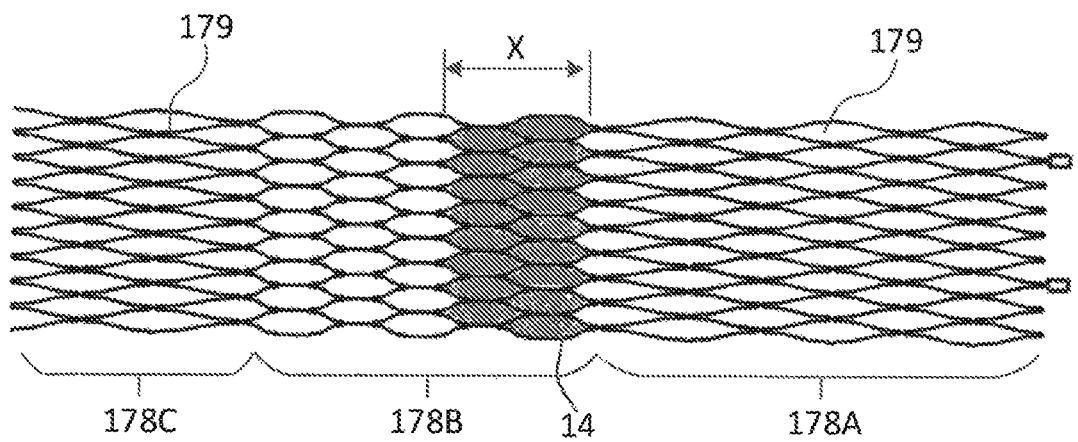

As shown in FIG. 38E, gap 14 is defined by an alternating pattern of a single uncoated cell adjacent to two adjacent uncoated cells downstream from the single uncoated cell. x is the distance from one end of the single coated cell to the opposing end of the two adjacent uncoated cells. As shown in FIG. 38F, gap 14 is defined by an alternating pattern of two adjacent uncoated cells adjacent to a single uncoated cell downstream from the two adjacent uncoated cells. x is the distance from one end of the two adjacent uncoated cells to the opposing end of the single coated cell. As shown in FIG. 38G, gap 14 is defined by an alternating pattern of a first pair of two adjacent uncoated cells adjacent to a second pair of two adjacent uncoated cells downstream from the first pair of two adjacent uncoated cells. x is the distance from one end of the first pair of two adjacent uncoated cells to the opposing end of the second pair of two adjacent uncoated cells. As shown in FIG. 38H, gap 14 is defined by two adjacent rings of uncoated cells. x is the width of the two adjacent rings of uncoated cells along the longitudinal axis of the frame.

Figure 38I:
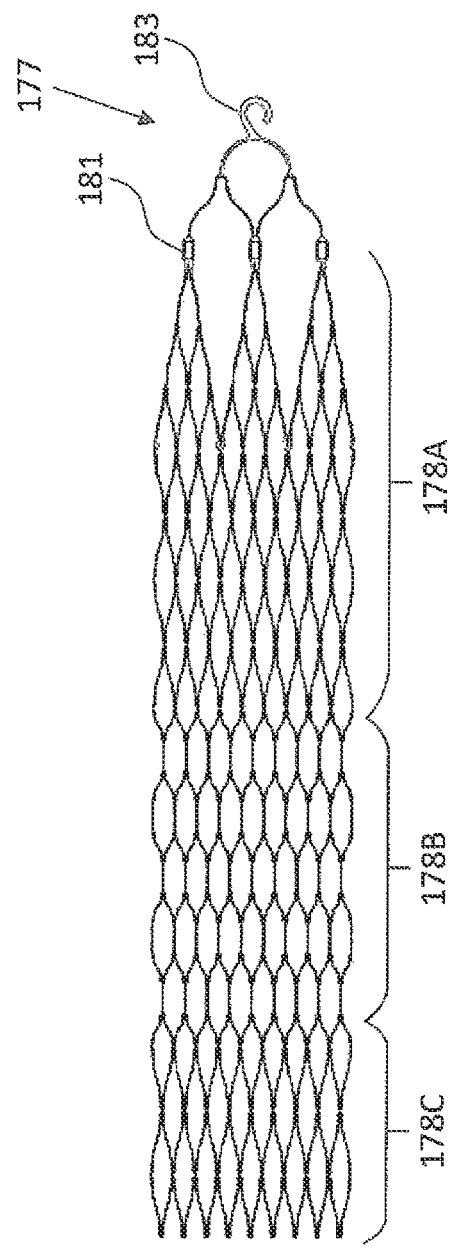
FIG. 38I illustrates a frame structure comprising a plurality of cells having a deployment and retrieval mechanism.

Referring now to FIG. 38I, flow modulator 10 may include deployment and retrieval mechanism 177 for facilitating deployment and/or removal of flow modulator 10 from the patient. Deployment and retrieval mechanism 177 includes hook portion 183 coupled to the proximal end of upstream component 12, e.g., to constricted section 180, via pushers 181. For example, hook portion 183 may have a plurality of arms coupled to the end of upstream component 12 via pushers 181. In this manner a retrieval device, e.g., a hook or goose-neck snare device, may be coupled to hook portion 183 to pull deployment and retrieval mechanism 177 towards a sheath, e.g., sheath 164 described above, to compress flow modulator 10 into the sheath for retrieval. Further, pushers 181 facilitates deployment of flow modulator 10 from a compressed state within the sheath to an expanded state outside of the sheath when force is exerted on hook portion 183. As will be understood by a person having ordinary skill in the art, hook portion 183 may be coupled to the proximal end of the upstream component and/or the distal end of the downstream component of any of the flow modulators described herein, as a separate component that is, e.g., molded, glued, compressed, welded, etc. to the frame.

Figure 38J:
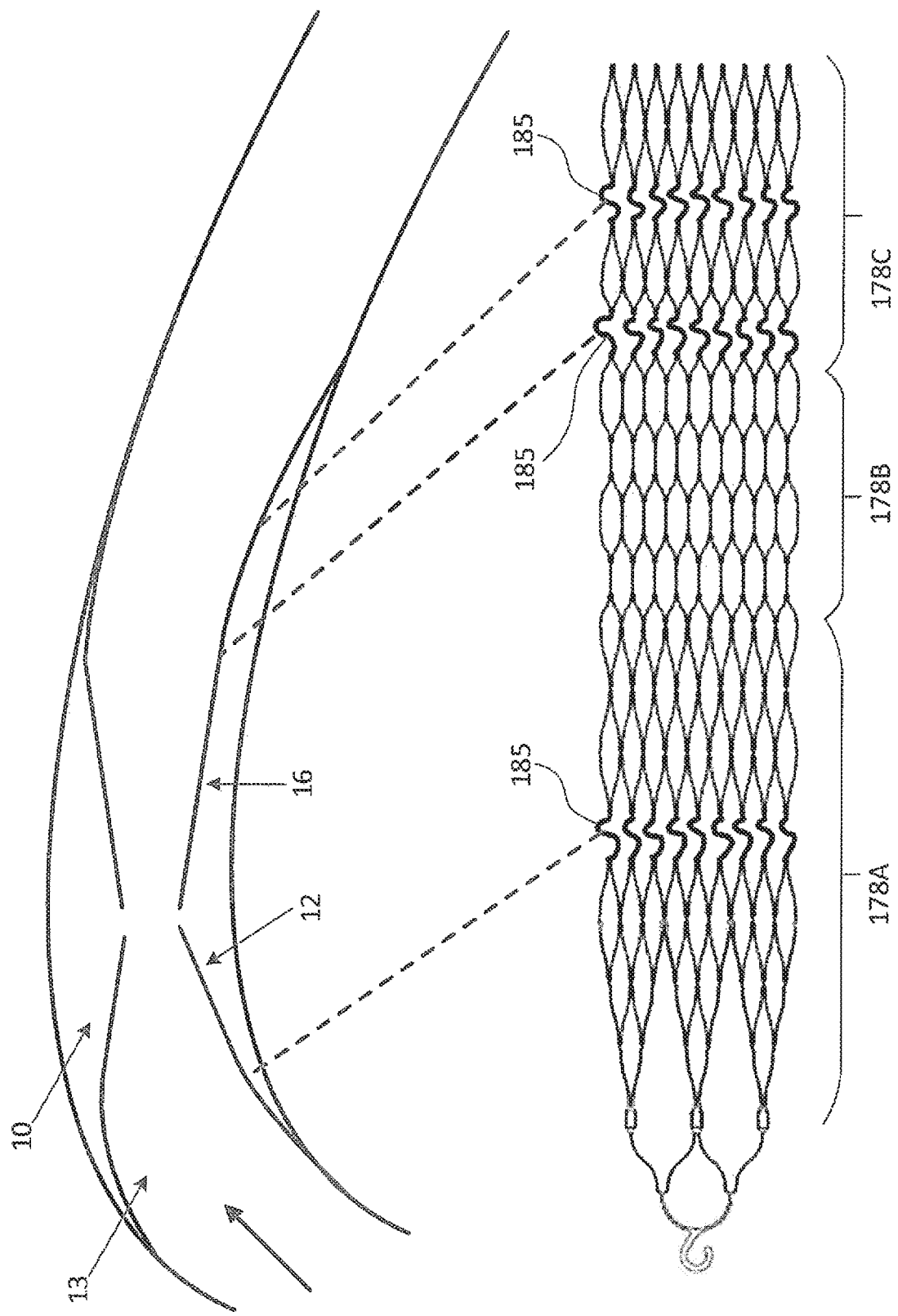
FIG. 38J illustrates a frame structure comprising a plurality of cells having flexible connection portions.
Figure 38K:
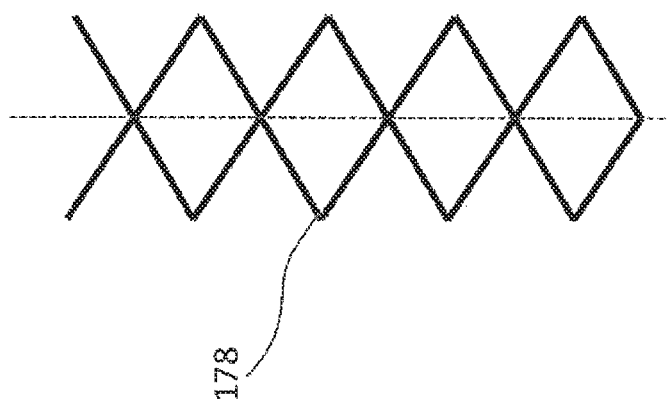
FIG. 38K illustrates a flexible connection portions of a frame structure in accordance with the embodiment of FIG. 38J.
Figure 38K:
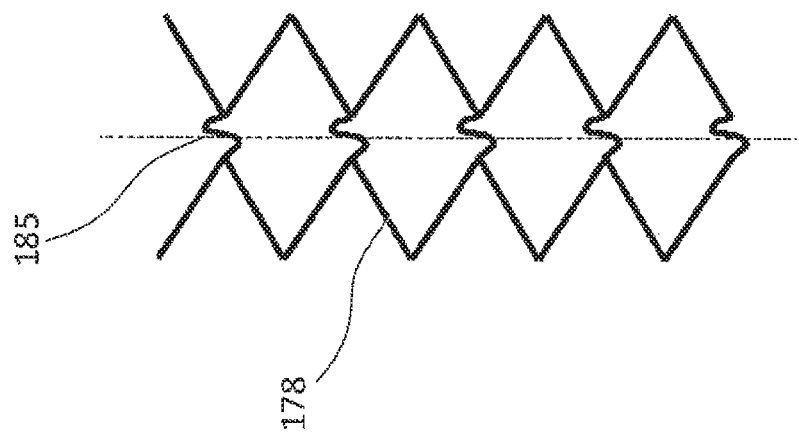

Referring now to FIGS. 38J and 38K, flow modulator 10 may include one or more flexible joints 185 in accordance with some principles of the present invention to facilitate implantation within a patient having a bended IVC. As shown in FIG. 38J, first plurality of cells 178A of upstream component 12 may include flexible joints 185 adjacent inlet 13, which allows less kinking of the nozzle at wider bending angles of the IVC. In addition, third plurality of cells 178C may include flexible joints 185 between first diverging portion 176A and second diverging portion 176B, and along second diverging portion 176B, e.g., between the juncture of first diverging portion 176A and second diverging portion 176B and atraumatic end 182.

Accordingly, this design will allow the downstream portion of upstream component 12 and the upstream portion of downstream component 16 to bend less than the other portions of flow modulator 10 to ensure the jet of fluid flow exiting upstream component 12 is centered to the inlet of downstream component 16.

As shown in FIG. 38K, flexible joints 185 may be positioned at the point where two adjacent cells meet. FIG. 38K illustrates frame 178 having a cell-cell joint with flexible joints 185 (left) and frame 178 having a cell-joint without flexible joints therebetween. As will be understood by a person having ordinary skill in the art, flow modulator 10 may include more or fewer flexible joints 185 along the frame to optimize implantation of flow modulator 10 within a bended IVC.

Figure 39:
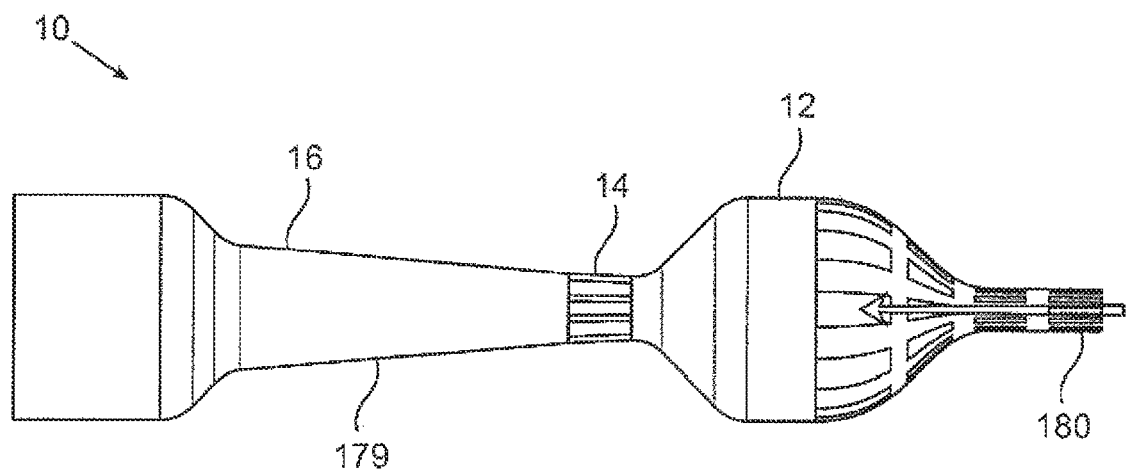
FIG. 39 is a schematic view of a fluid flow modulator, in accordance with another embodiment of the present invention, coated with a biocompatible material.

Referring now to FIG. 39, another embodiment of the present invention, flow modulator 10 is coated with biocompatible material 179 at upstream component 12 and downstream component 16 and the uncoated portion of frame 178 therebetween defines gap 14. The average void space of the plurality of cells at gap 14 may be larger than the average void space of the remaining portion of second plurality of cells 178B for enhanced flow into gap 14. For example in FIG. 39, frame 178 at gap 14 has a plurality of longitudinally running struts which are substantially parallel to one another (and substantially parallel to the longitudinal axis of the vessel). FIG. 39 also illustrates flow modulator 10 with constricted section 180, but does not include atraumatic end 182.

Figure 40A:
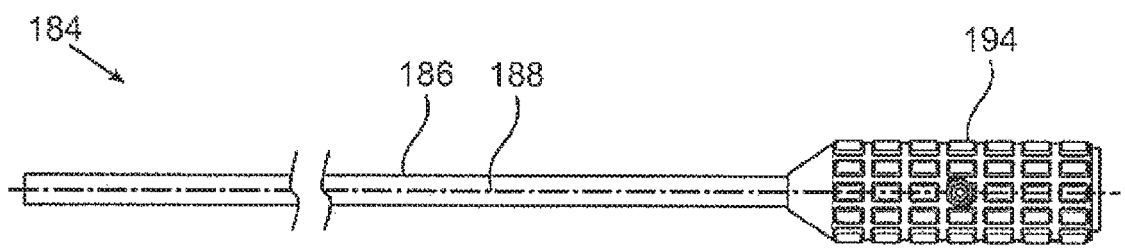
FIGS. 40A and 40C are side views of an exemplary outer assembly (FIG. 40A) and an inner assembly (FIG. 40C) of a delivery device, in accordance with embodiments of the present invention.
Figure 40B:
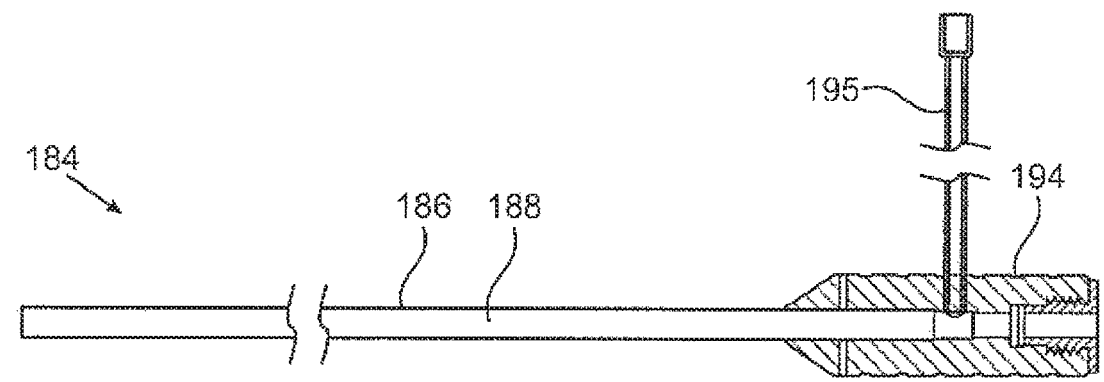
FIGS. 40B, 40D, and 40E are cross-sectional views of the inner and outer assemblies of the components of the delivery device shown in FIGS. 40A and 40C, in accordance with embodiments of the present invention.
Figure 40C:
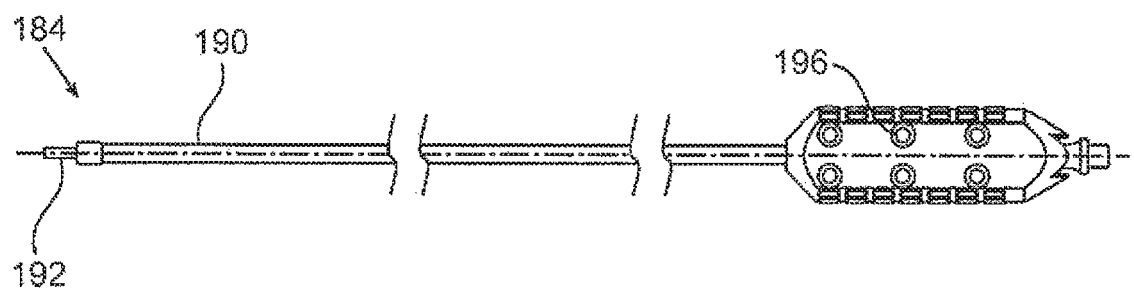
Figure 40D:
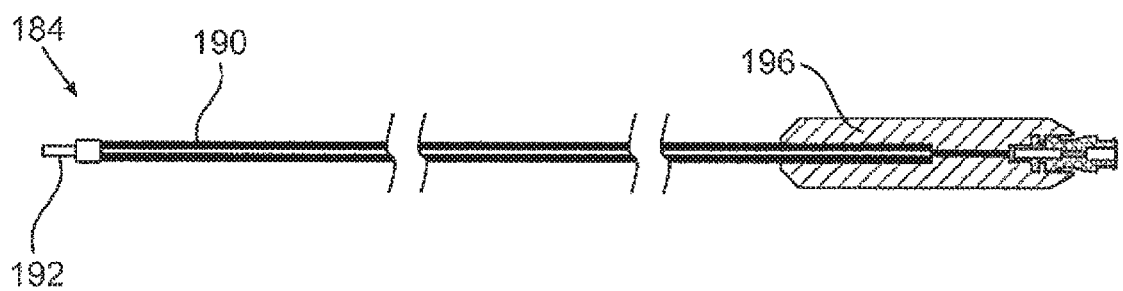
Figure 40E:
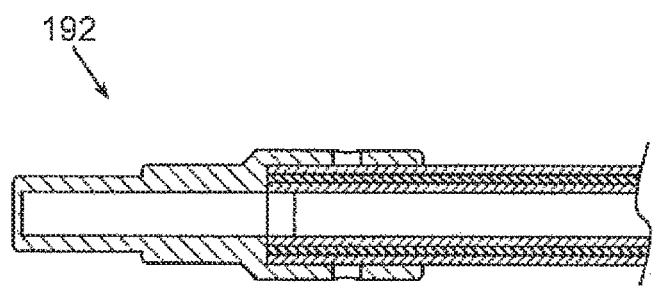

Referring now to FIGS. 40A through 40E, an embodiment of delivery device 184 for delivering flow modulator 10 to the body lumen is described. In FIGS. 40A and 40B, delivery device 184 includes sheath 186 having lumen 188 of suitable size to hold flow modulator 10 in a contracted, delivery state. In FIGS. 40C, 40D, and 40E, delivery device 184 also may include inner assembly 190 to facilitate deployment of flow modulator 10 through the distal end of sheath 186. Alternatively, delivery device 184 may include handle 194 at the proximal end of sheath 186 to allow a clinician to hold sheath 186 and optionally for coupling to hose 195 for flushing out lumen 188 of sheath 186.

Additionally, inner assembly 190 may include tip 192 coupled to the distal end of inner assembly 190 configured to couple to constricted end 180 of flow modulator 10 during an acute treatment. Inner assembly 190 additionally may be coupled to handle 196 at the proximal end of inner assembly 190. Handle 194 is configured to be held when inner assembly 190 is moved, via handle 196, distally through sheath 186, thereby pushing flow modulator 10 through lumen 188 to deploy flow modulator 10 out the distal end of sheath 186. FIG. 40B and FIG. 40D are cross-sectional views of sheath 186 and inner assembly 190, respectively. FIG. 40E is a enlarged view of tip 192, showing the stepped configuration to enable coupling to constricted end 180, and facilitate pushing during deployment and pulling during retrieval.

Figure 41:
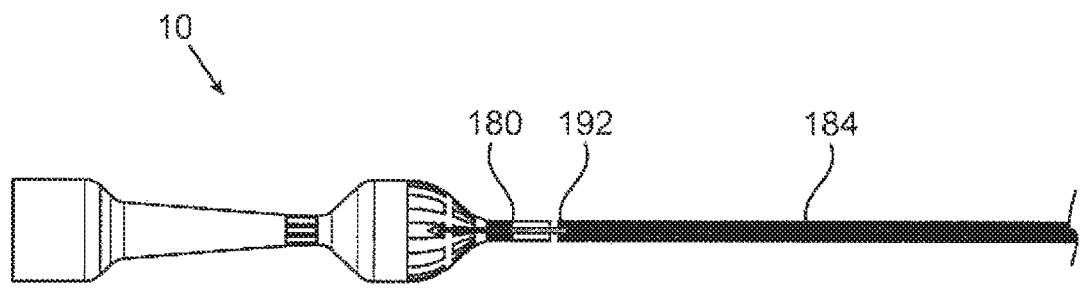
FIG. 41 is a schematic view of a fluid flow modulator and delivery device coupled together for acute treatment, in accordance with another embodiment of the present invention.

FIG. 41 is an exemplary view of flow modulator 10 and delivery device 184 coupled together for use during an acute treatment. In this case, flow modulator 10 remains coupled to delivery device 184 throughout the acute treatment to facilitate retrieving flow modulator 10 after completion of the treatment. Illustratively, constricted end 180 of flow modulator 10 is coupled to tip 192 of delivery device 184 during the acute treatment. Alternatively, flow modulator 10 may be detached from delivery device 184 and left implanted for an amount of time (e.g., hours, days, months, years) for a chronic treatment. If implanted, flow modulator 10 may be retrieved similar to the manner described above with respect to FIGS. 32-34.

Figure 42A:
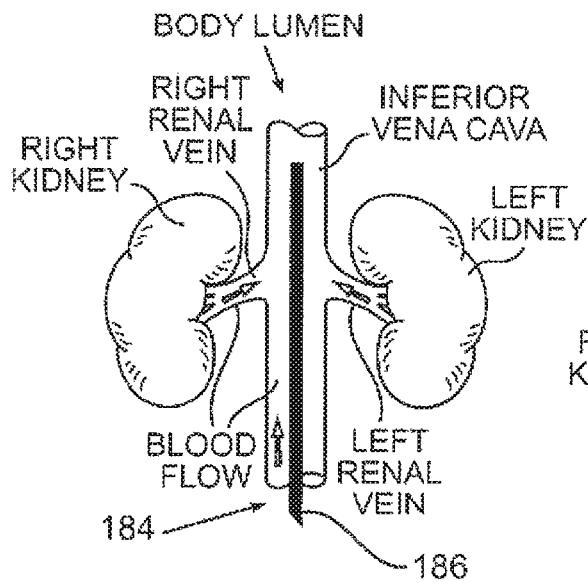
FIGS. 42A-42F are schematic views of a method of delivering a fluid flow modulator, in accordance with another embodiment of the present invention.
Figure 42B:
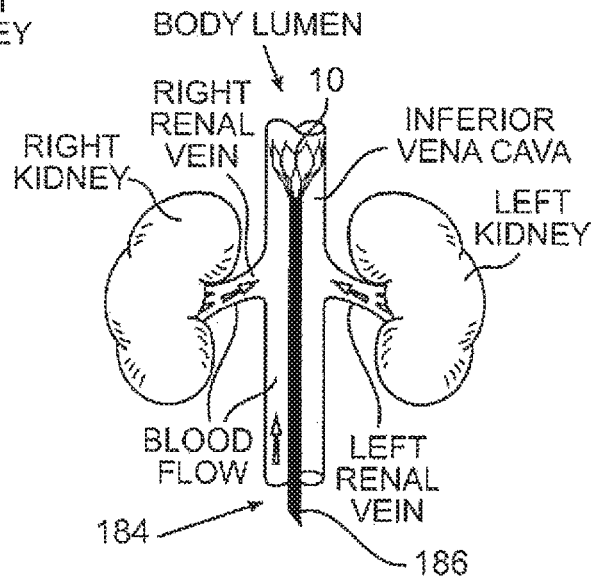
Figure 42C:
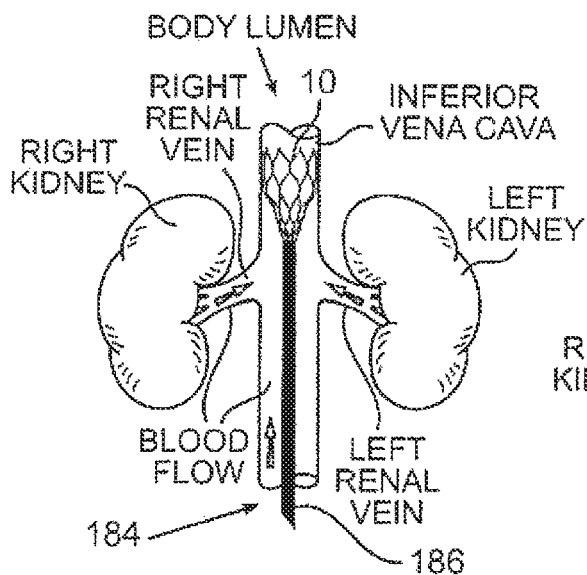
Figure 42D:
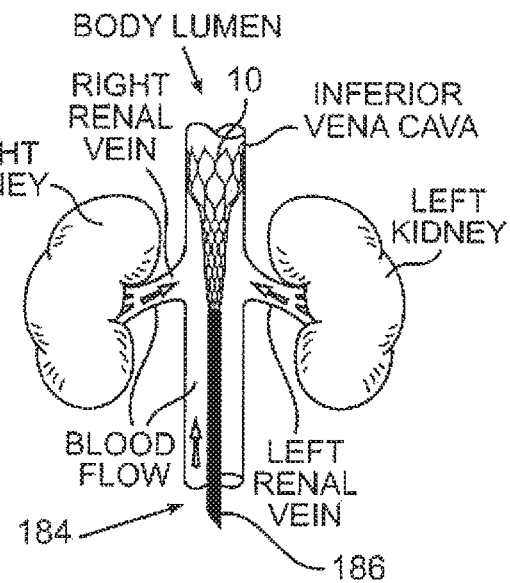
Figure 42E:
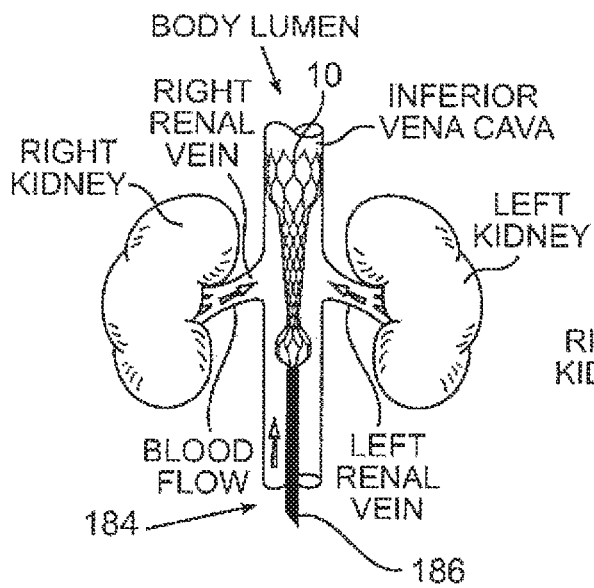
Figure 42F:
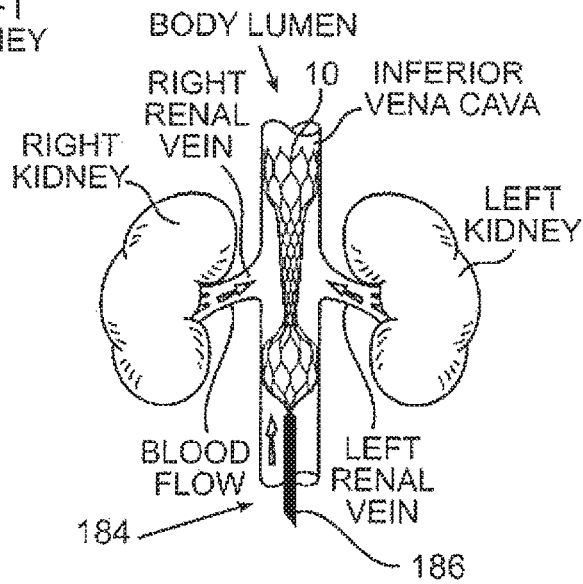
Figure 43A:
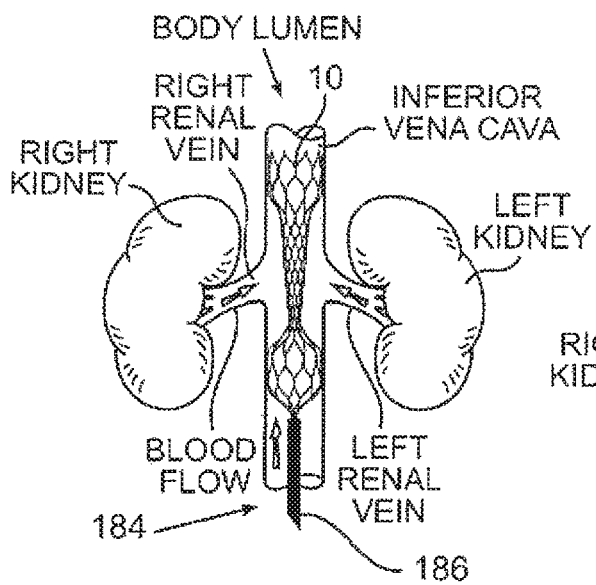
FIGS. 43A-43F are schematic views of a method of retrieving a fluid flow modulator, in accordance with another embodiment of the present invention.
Figure 43B:
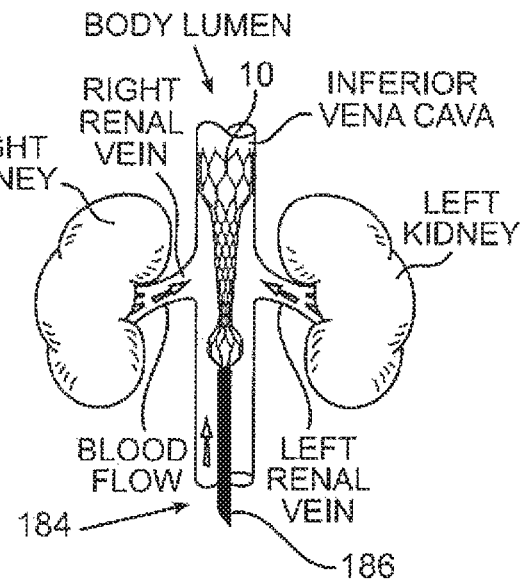
Figure 43C:
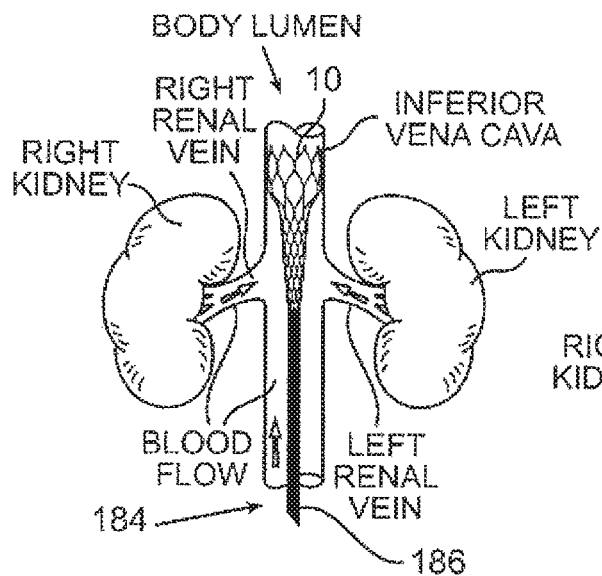
Figure 43D:
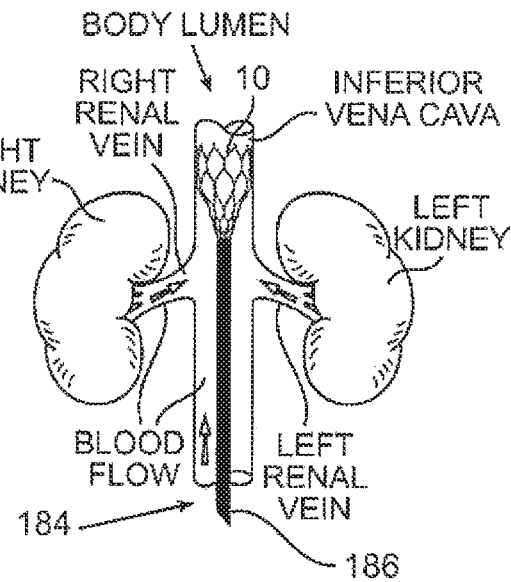
Figure 43E:
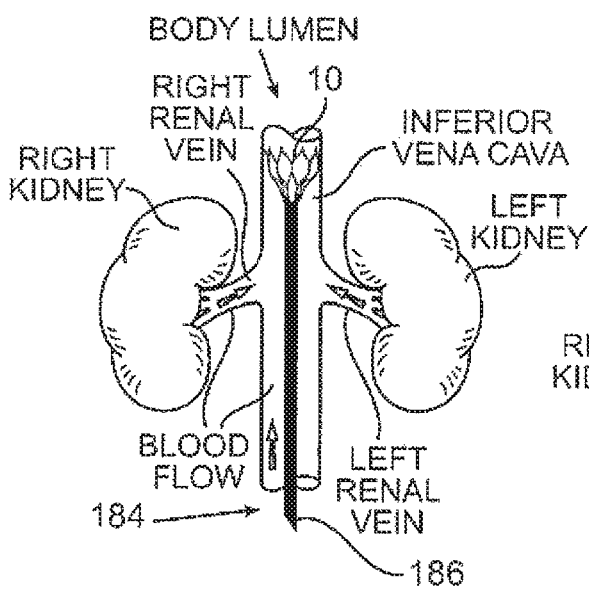
Figure 43F:
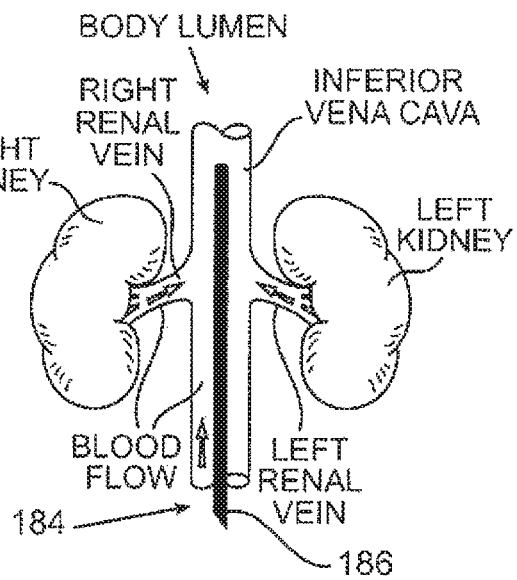

Referring now to FIGS. 42A through 43F, deployment and retrieval of flow modulator 10 from delivery device 184 in the body lumen is described. Flow modulator 10 is shown in uncoated form for ease of illustration. FIG. 42A illustrates delivery device 184 introduced into the body lumen, with sheath 186 positioned downstream a branch lumen(s) (e.g. renal vein(s), hepatic vein(s)). Flow modulator 10 is disposed within lumen 188 of sheath 186 in a contracted, delivery state. By pulling sheath 186 proximally while flow modulator 10 remains in place, FIGS. 42B through 42F illustrate flow modulator 10 self-expanding to a deployed configuration in the body lumen out the distal end of sheath 186. FIG. 42F shows flow modulator 10 in the expanded, deployed configuration exposed past the distal end of sheath 186. For example, sheath 186 may be pulled proximally while inner assembly 190 (which is coupled to flow modulator 10) is held in place in sheath 186 to unsheath flow modulator 10 at a target location within a body lumen, e.g., where the renal veins intersect with the inferior vena cava. To retrieve flow modulator 10, flow modulator 10 may be retracted back into sheath 186, as illustrated in FIGS. 43A through 43F. For example, sheath 186 may be moved distally while inner assembly (which is coupled to flow modulator 10) is held in place to transition flow modulator from the expanded, deployed state to a contracted state within lumen 188 of sheath 186. Delivery device 184 (having flow modulator 10 contracted therein) is then moved proximally and out of the patient's body.

Figure 44:
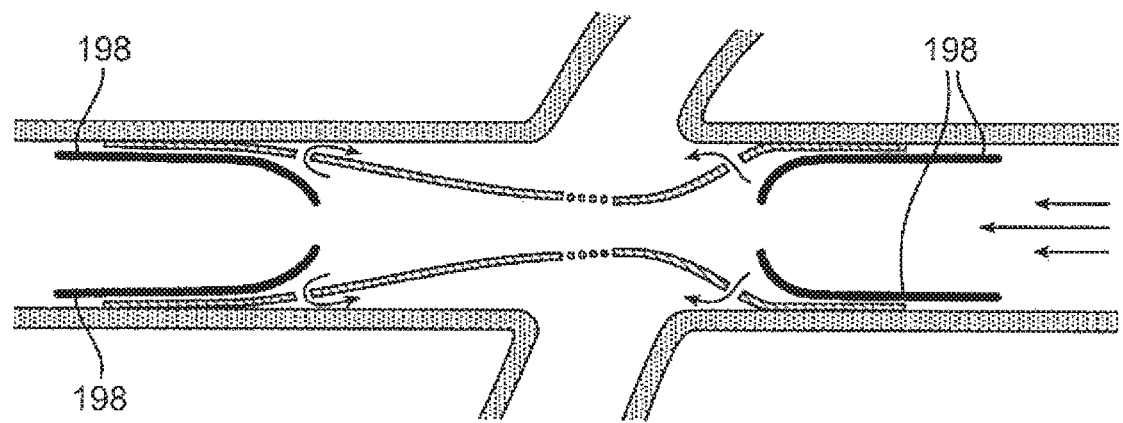
FIG. 44 is a schematic view of a fluid flow modulator with an inner device, in accordance with another embodiment of the present invention.

With respect to FIG. 44, inner device 198 is shown inserted into flow modulator 10. One or more inner devices 198 may be added in upstream component 12 and/or downstream component 16. Preferably, inner device(s) 198 may fit within the diameter of flow modulator 10 to partially block the opening(s) in a nozzle/diffuser (e.g., opening 31 in FIGS. 4 and 5), thereby controlling the pressure reduction. Inner device(s) 198 preferably has a constant diameter slightly smaller than the inner diameter at the end of upstream component 12 and/or downstream component 16 and then angles inward in a converging/diverging manner as shown.

Figure 45:
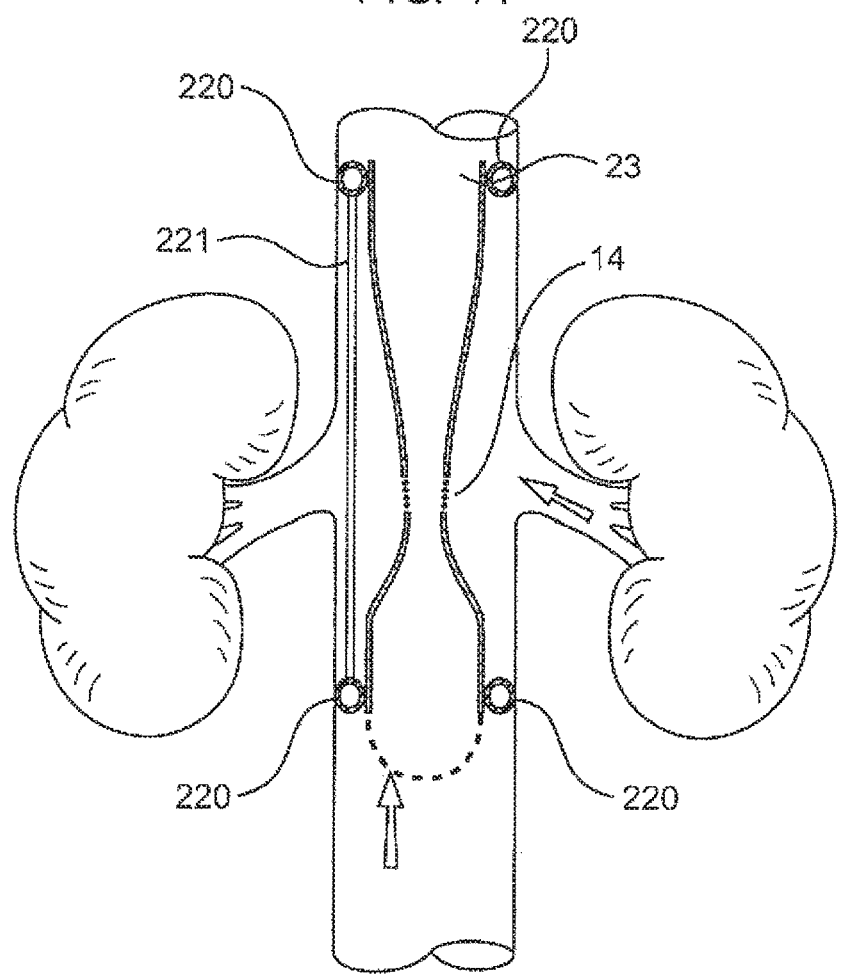
FIG. 45 is a schematic view of a fluid flow modulator with an external inflating element, in accordance with another embodiment of the present invention.

In FIG. 45, external inflating element 220 is positioned on the proximal and distal ends on the outer surfaces of flow modulator 10. External inflating element 220 (e.g. a balloon) may allow wash-out of no-flow zones and reduce the risk of emboli creation. Additionally, external inflating element 220 may be used to control the level of suction by creating distance between the balloon and vessel wall. External inflating element 220 may optionally be coupled to pipe 221 at one or both sides or pipe 221 may surround the flow modulating portion.

Figure 46:
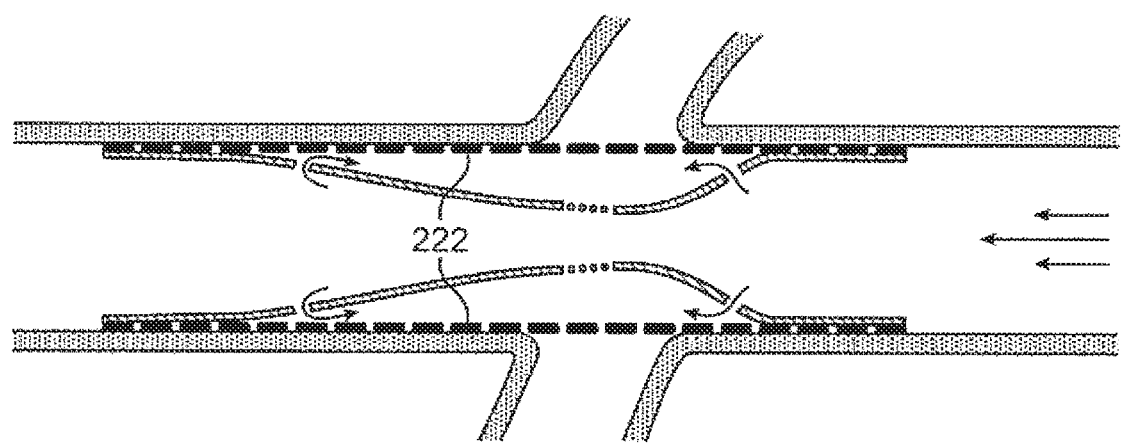
FIG. 46 is a schematic view of a fluid flow modulator with an external frame, in accordance with another embodiment of the present invention.

Referring now to FIG. 46, another embodiment of the present invention having external tubular frame 222 installed with flow modulator 10 is described. Similar to the embodiment of FIG. 26, external tubular frame 222 may help prevent reduction in body lumen diameter during fluid removal or reduced pressure. Preferably, flow modulator 10 fits entirely within external tubular frame 222. External tubular frame 222 has a plurality of openings (e.g., cells in a laser cut stent) such that blood flows through external tubular frame 222.

Figure 47:
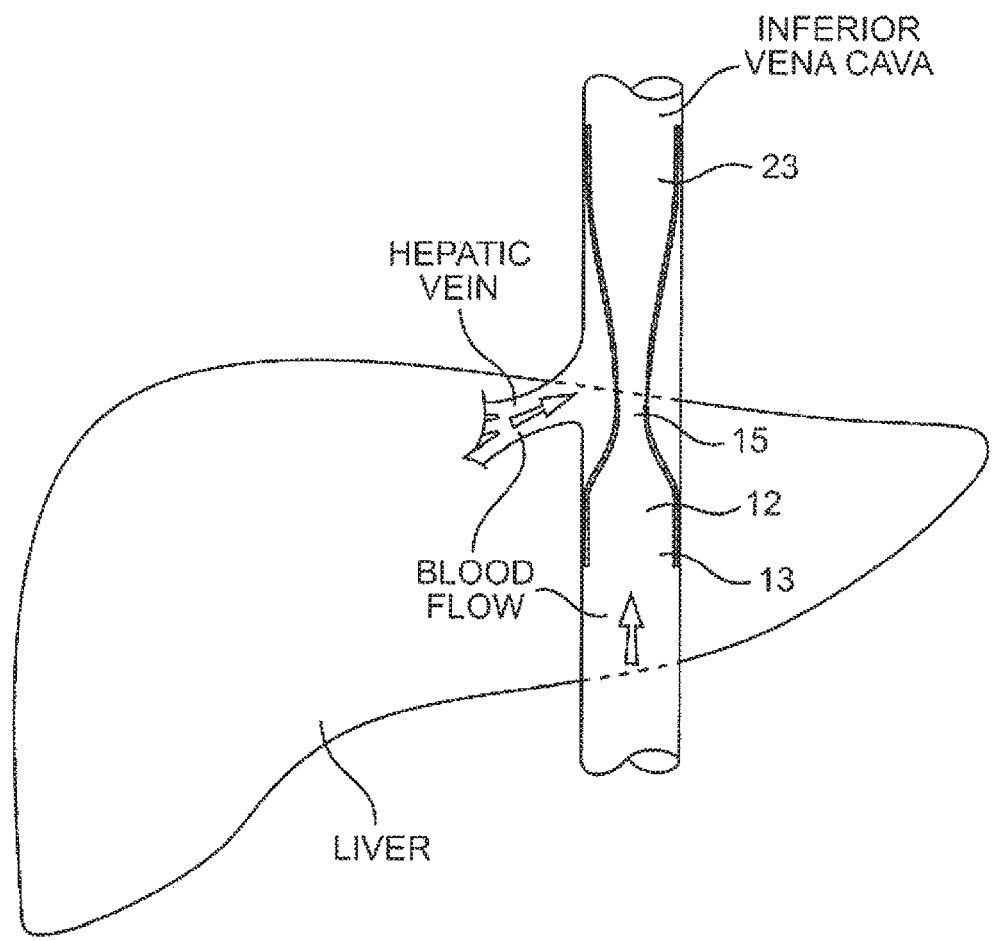
FIG. 47 is a schematic view of a fluid flow modulator installed near a hepatic vein, in accordance with another embodiment of the present invention.

In FIG. 47, flow modulator 10 is shown installed in the inferior vena cava at the branch to a hepatic vein Implanting flow modulator 10 within the body lumen may include implanting upstream component 12 in an inferior vena cava such that inlet 13 is upstream from a branch off to a hepatic vein(s) and downstream component 16 in the inferior vena cava such that exit 23 is downstream from the branch off to the hepatic vein(s). The low pressure area near gap 14 preferably may be positioned at the branch to the hepatic vein(s), thereby inserting blood back to the inferior vena cava and improving splanchnic circulation. Flow modulator 10 implanted within the inferior vena cava at the branch to the hepatic vein(s) is expected to improve liver function and/or may be used instead of, or in parallel to, a TIPS procedure. Advantageously, flow modulator 10 improves hepatic flow to the inferior vena cava allowing blood to enter the liver for natural filtering (in contrast to a TIPS procedure that bypasses blood from the liver). Flow modulator 10, whether used together with a TIPS procedure or in place of a TIPS procedure, is expected to treat conditions such as portal hypertension (often due to liver cirrhosis) which frequently leads to intestinal bleeding, life-threatening esophageal bleeding (esophageal varices), the buildup of fluid within the abdomen (ascites), and/or hepatorenal syndrome.

Figure 48A:
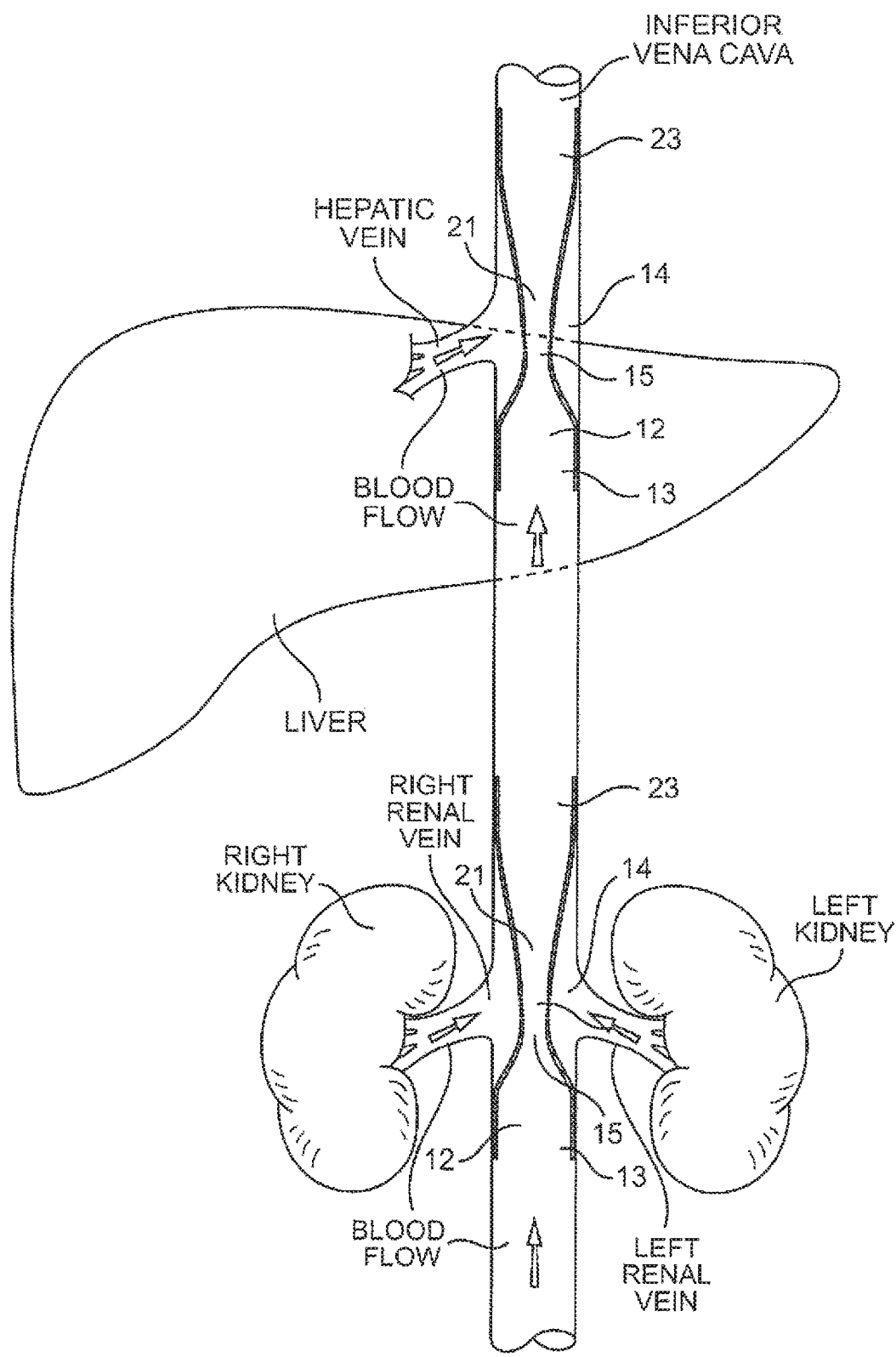
FIGS. 48A and 48B are schematic views of a fluid flow modulator, in accordance with another embodiment of the present invention, installed near both a renal vein and a hepatic vein, either as separate modulators (FIG. 48A) or connected as one (FIG. 48B)
Figure 48B:
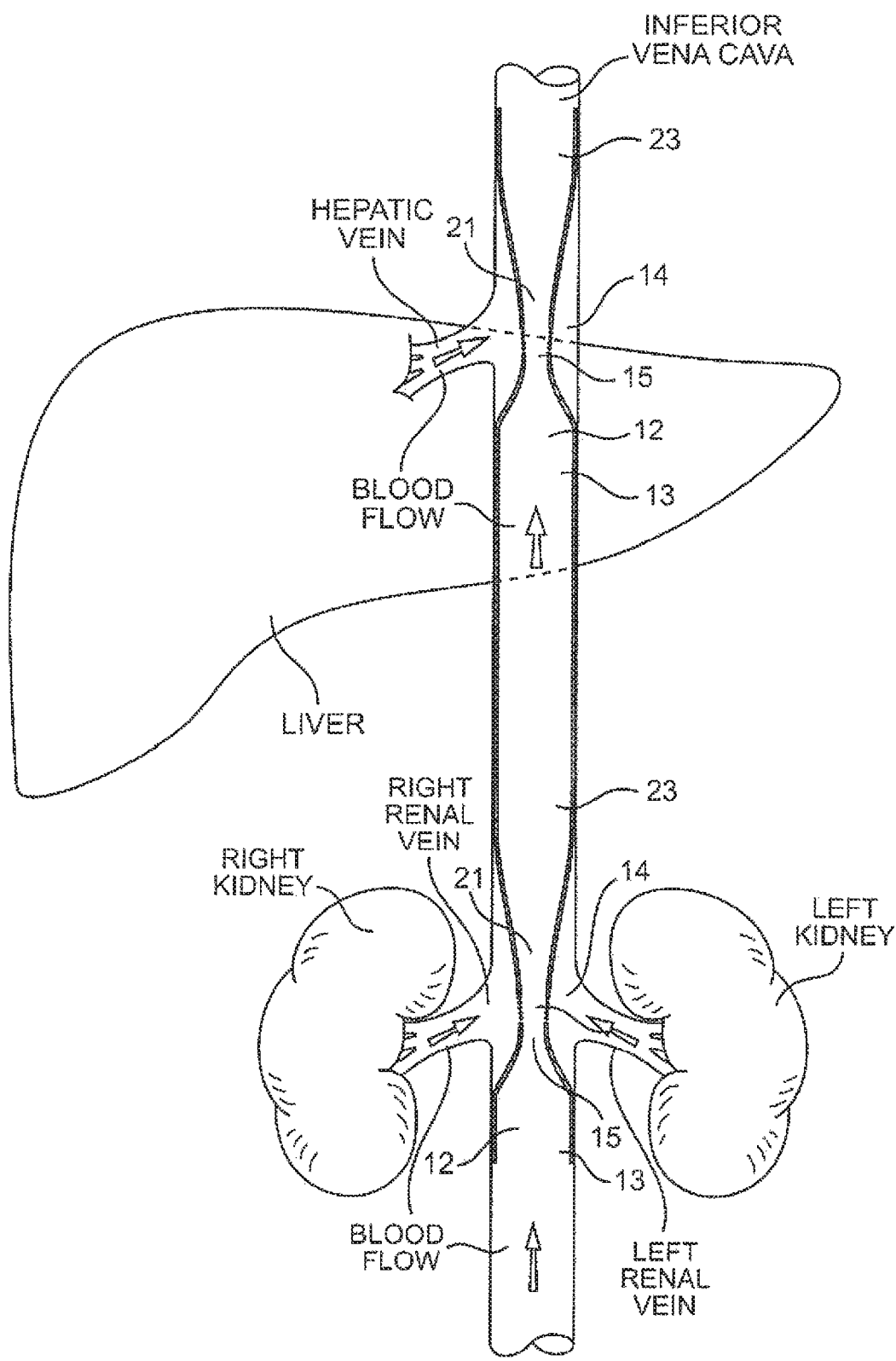

Referring now to FIGS. 48A and 48B, fluid flow modulator 10 is shown deployed in the inferior vena cava such that its gap communicates with a renal vein(s) and a second, discrete flow modulator 10 deployed in the inferior vena cava such that its gap communicates with a hepatic vein(s). In FIG. 48B, single flow modulator 10 is deployed in the inferior vena cava extending across both a renal vein(s) outlet and a hepatic vein(s) outlet. In this latter embodiment, flow modulator 10 is formed as a single unit and configured as two flow modulators; i.e. one frame 178, two upstream components 12, two downstream components 16, and two gaps 14, each to reduce pressure at their respective vein outlets.

Figure 49:
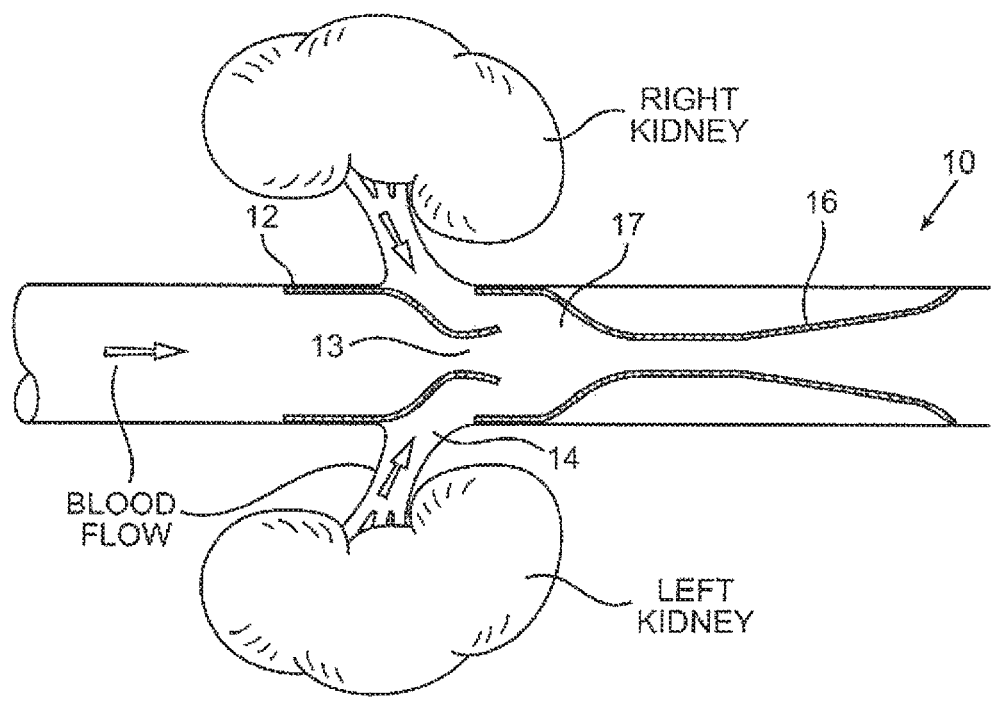
FIG. 49 is a schematic view of a fluid flow modulator, in accordance with another embodiment of the present invention, in which an outlet nozzle of an upstream flow accelerator enters a portion of a downstream flow decelerator.

Referring now to FIG. 49, flow modulator 10 includes upstream component 12 with outlet 13 and downstream component 16, which has an upstream divergent mouth entry 17. Outlet 13 enters entry 17 and this area serves as gap 14. In this example, upstream component 12 may be installed in the inferior vena cava upstream to the branch off to the renal vein(s) and the downstream component 16 may be installed in the inferior vena cava downstream of the branch off to the renal vein(s). Outlet 13 also is downstream of the branch off to the renal vein(s). Upstream component 12 first converges then diverges at outlet 13 to allow for a more arranged and directed flow. Downstream component 16 first converges to continue acceleration of the arranged and directed flow in a more stable and unified form. The straight portion in downstream component 16 may help align the flow before it is diffused and reduce flow separation from the diffuser wall, thereby reducing pressure losses. Preferably, the converging angles are wider than the diverging angles.

Figure 50A:
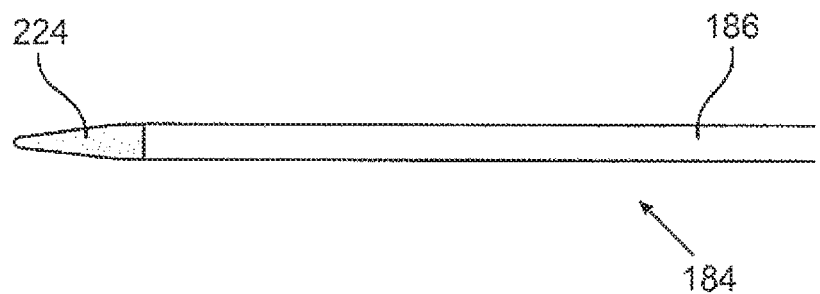
FIGS. 50A-50F illustrate a method of delivering and retrieving a fluid flow modulator, in accordance with another embodiment of the present invention.
Figure 50B:
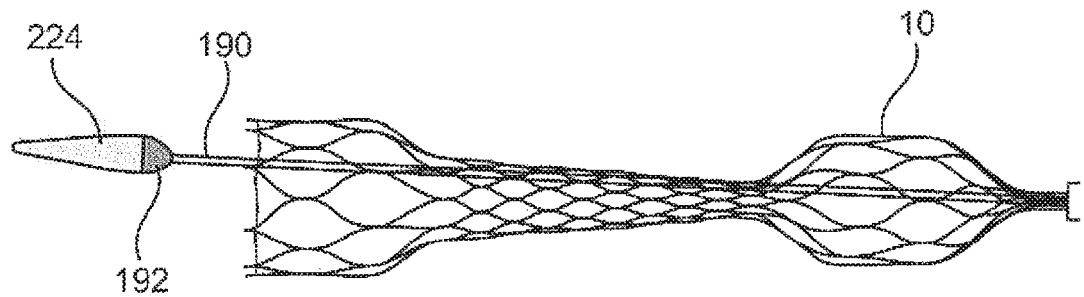
Figure 50C:
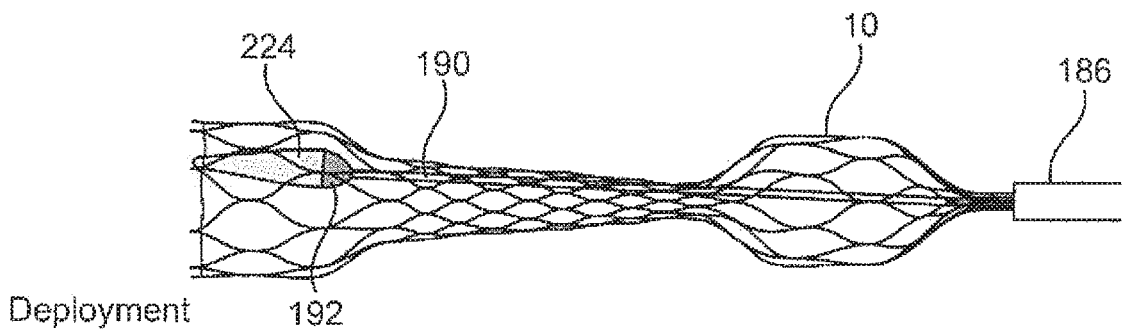
Figure 50D:
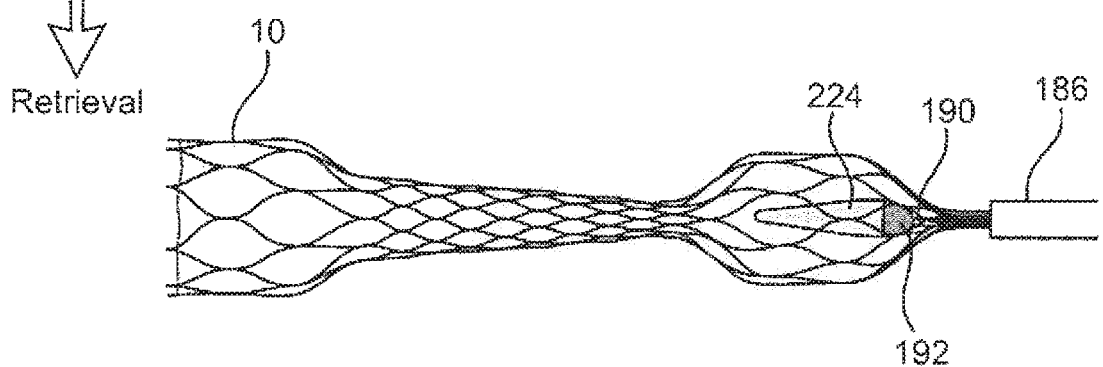
Figure 50E:
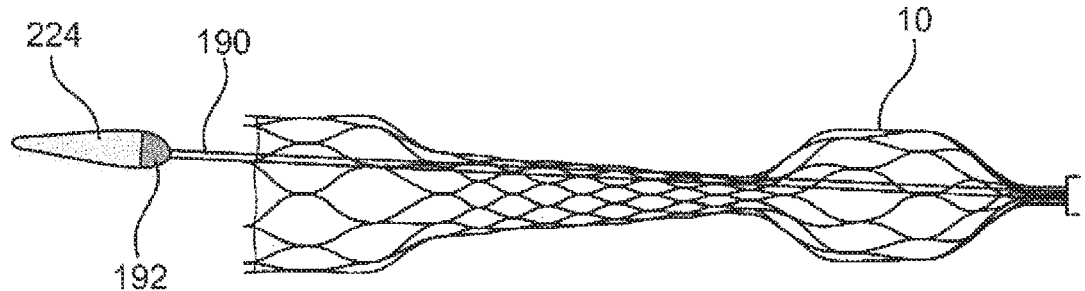
Figure 50F:
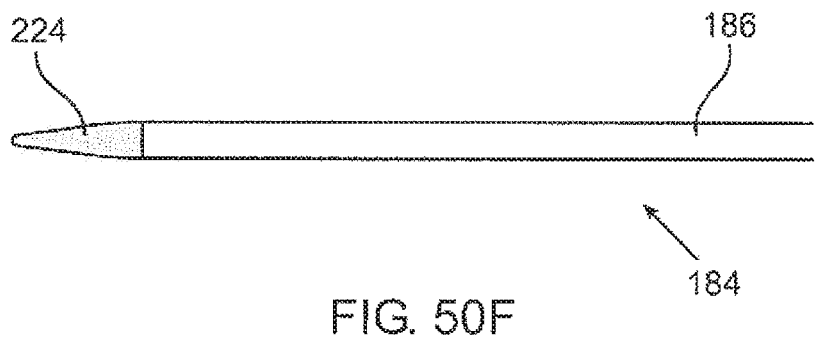

Referring now to FIGS. 50A-50F, the deployment and retrieval of flow modulator 10 from delivery device 184 in the body lumen is described. Similar to FIGS. 42A-F and 43A-F, flow modulator 10 is deployed in a body lumen. Delivery device 184 includes end cap 224 that is part of tip 192 at the distal end of inner assembly 190, allowing for ease of insertion. By pulling sheath 186 proximally while flow modulator 10 and inner assembly 190 remain in place, FIGS. 50A through 50B illustrate flow modulator 10 (shown as a metal stent with biocompatible coating of thermoplastic polyurethane (TPU)) self-expanding to a deployed configuration out the distal end of sheath 186. Alternatively, inner assembly 190 and flow modulator 10 may be pushed distally while sheath 186 is secured in place, thereby deploying flow modulator 10 in the body lumen. FIGS. 50C and 50D illustrate inner assembly 190 moving proximally to secure flow modulator 10 for the acute treatment. To retrieve flow modulator 10, flow modulator 10 may be retracted back into sheath 186, as illustrated in FIGS. 50E through 50F. For example, sheath 186 may be moved distally while inner assembly 190 is held in place to transition flow modulator 10 from the expanded, deployed state to a contracted state within sheath 186. Delivery device 184 then may be moved proximally and out of the patient's body.

Referring now to FIGS. 51A-51C, further alternative embodiments of the flow modulator of the present invention are described. In FIG. 51A, flow modulator 10 is annotated with symbols depicting dimensions in accordance with a preferred embodiment. Exemplary dimensions in accordance with some embodiments are similar to those described above with respect to FIG. 3A. $L_{inlet}$ is the overall length of upstream component 12. $L_{orifice}$ is the distance from outlet 15 of upstream component 12 to entry 21 of downstream component 16. $L_{diffuser}$ is the length of the diverging portion of downstream component 16. Diffuser angle $\alpha/2$ is smaller than converging angle $\beta/2$. Accordingly, the length of the converging region $L_{inlet}$ can be smaller than the diverging region $L_{diffuser}$. Both angles may vary along the longitudinal axis of flow modulator 10, allowing smoother convergence and then divergence of flow, with minimum flow separation and energy loss (i.e. shaped according to Stratford curve). $D_{diffuser-out}$ is the diameter of second diverging portion 176B and $D_{outlet}$ is the diameter of the distal end of flow modulator 10. The length $L_{diffuser}$ may be short enough such that $D_{diffuser-out}$ is less than $D_{outlet}$ or long enough such that $D_{diffuser-out}$ is equal to Daudet. $D_{nozzle}$ is the diameter of outlet 15 of upstream component 12. $D_{diffuser-in}$ is the diameter at entry 21 of downstream component 16. $D_{diffuser-in}$ is equal to or larger than $D_{nozzle}$.

As depicted in FIGS. 51B and 51C, having the diffuser inlet area larger than the nozzle outlet area allows more renal blood flow (RBF) to enter into the diffuser without competing for space with the IVC jet flow. The RBF may enter into the diffuser at entry 21 and surround IVC flow, creating a "ring" flow. A mixture of both flows occurs gradually downstream Importantly, the RBF also acts as a diffuser itself, to some extent, thus "cushioning" the IVC flow.

Figure 52A:
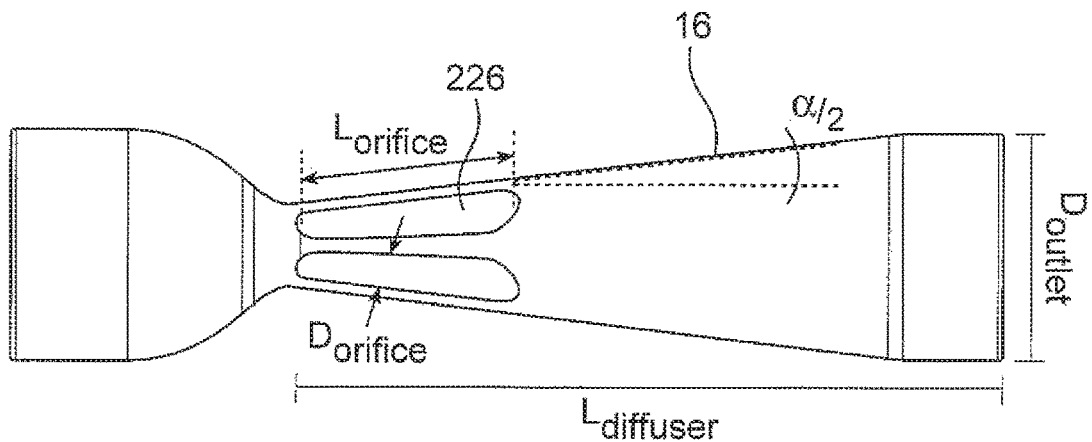
FIGS. 52A-52D are schematic views of a flow modulator with openings, in accordance with another embodiment of the present invention.
Figure 52B:
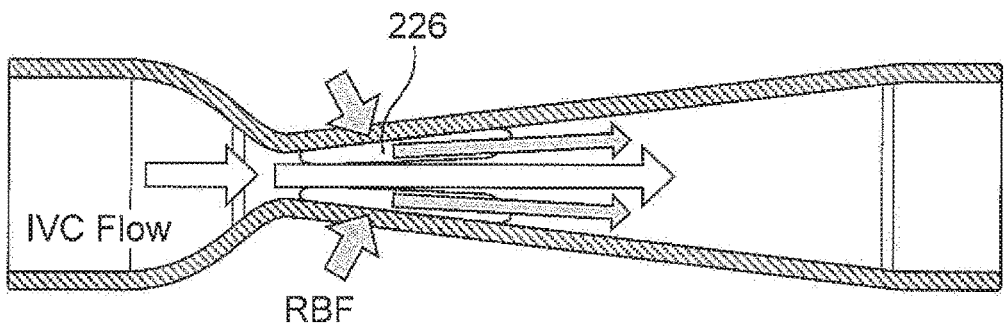
Figure 52C:
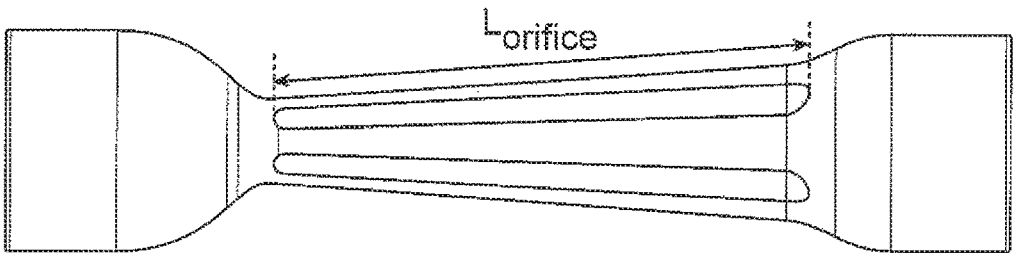
Figure 52D:
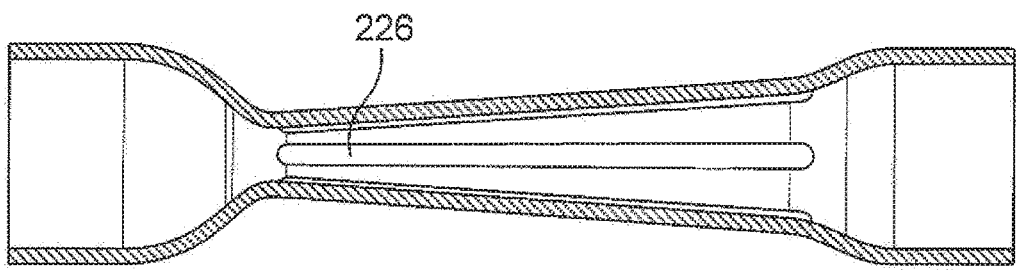

Referring now to FIGS. 52A-52D, a further alternative embodiment of flow modulator 10 includes opening 226. Opening 226 employs multiple longitudinal through-wall slits radially disposed around flow modulator 10 in an entrainment region between the inlet of upstream component 12 and the exit of downstream component 16. For example, the entrainment region may be integrally formed in downstream component 16 or in upstream component 12 or both. The openings from the slits form gaps that permit entrainment of fluid into flow modulator 10 between the inlet of the upstream component and the exit of the downstream component. Constructing multiple longitudinal slits in downstream component 16 keeps IVC jet flow restricted and manipulated by the diffuser, exposes the RBF to the low pressure of the IVC jet flow, and provides additional cross-sectional area in the diffuser for the RBF due to diverging angle α/2 of the diffuser. The slits may be formed in an entrainment region of the device that diverges in the same angle as the downstream component 16 from entry 21 to exit 23. In this manner, the openings formed by the longitudinal slits extend radially away from the central longitudinal axis such that the distance between the opening and the axis gradually increases as opening 226 extends from entry 21 to exit 23. This design maintains the benefits described with respect to the embodiments of FIGS. 51A-51C, while creating less resistance for the RBF and without impairing the diffuser's effect on the IVC jet flow. FIG. 52B is a cross sectional view of flow modulator 10, illustrating RBF entering into opening 226 in a manner that reduces turbulence and/or interference with the IVC flow in the entrainment region and the downstream component. The entrainment region may be formed of a frame coated with a biocompatible material, leaving the openings exposed such that fluid may be entrained into flow modulator 10 via the openings. The entrainment region may be 5-80% coated, preferably 20-60%, to actively stabilize the flow. For instance, a 12 mm nozzle perimeter may have coating over 25%, or 3 mm from the perimeter may be fully coated. This perimeter coating may be maintained to coat over 25% of the full area of flow modulator 10. As shown in FIGS. 52C and 52D, the length $L_{orifice}$ of openings 226 on the diffuser may extend along $L_{diffuser}$ to improve wash-out of the entire diameter of the diffuser $D_{outlet}$, and thus prevent recirculation regions. For example, $L_{orifice}$ may be 5-40 mm, preferably 8-25 mm. Larger diverging angles α/2 also may be used without flow separation and similar diffuser.

Figure 52E:
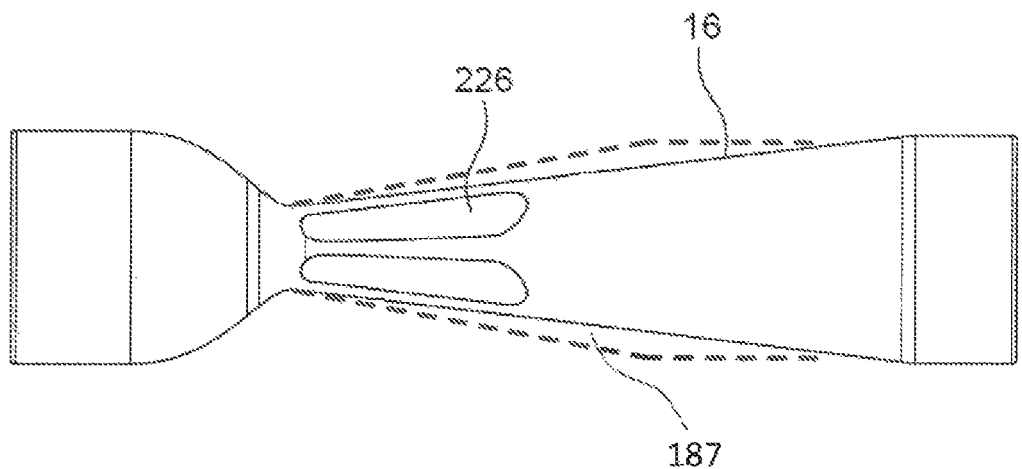
FIG. 52E is a schematic view of a flow modulator with openings, in accordance with yet another embodiment of the present invention, having extra lumen space.
Figure 52F:
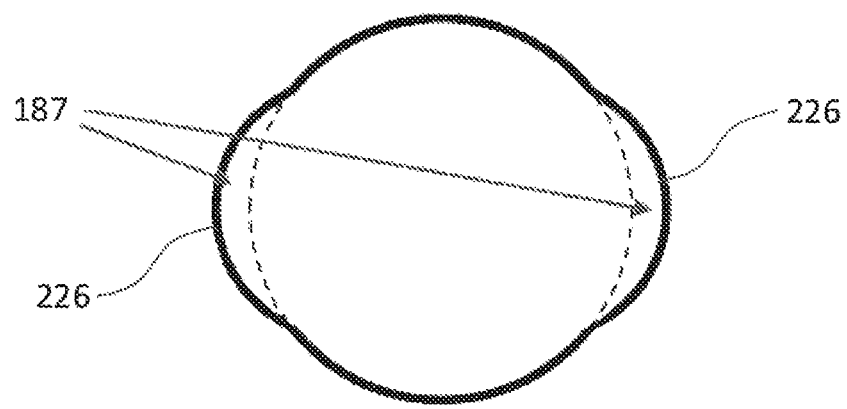

Referring now to FIGS. 52E and 52F, flow modulator 10 may include additional lumen space 187 adjacent openings 226 in accordance with some principles of the present invention. Specifically, as shown in FIG. 52F, the region of downstream component 16 having openings 226 bulge outwardly to provide additional lumen space 187 to flow modulator 10 in the expanded state, thereby allowing less resistance for renal flow as renal blood is gradually entrained into the main lumen of flow modulator 20 via openings 226. Accordingly, downstream component 16 may have a narrower diffuser angle, thereby creating less disturbed flow. The dashed lines in FIG. 52E illustrate the diameter of downstream component 16 as a result of the bulge at openings 226.

Figure 53A:
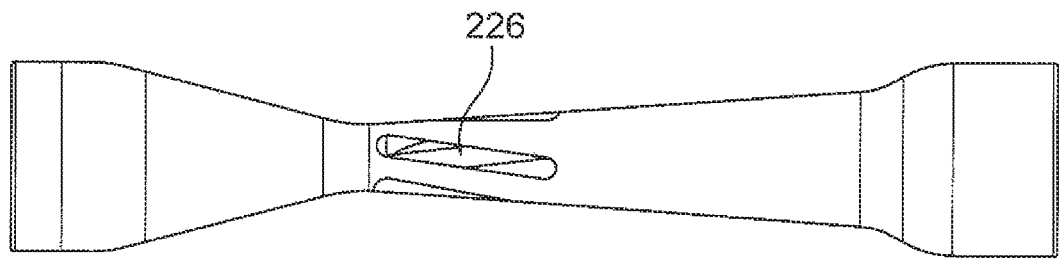
FIGS. 53A-53B are schematic views of a flow modulator with angular openings and corresponding flow pattern, in accordance with another embodiment of the present invention.
Figure 53B:
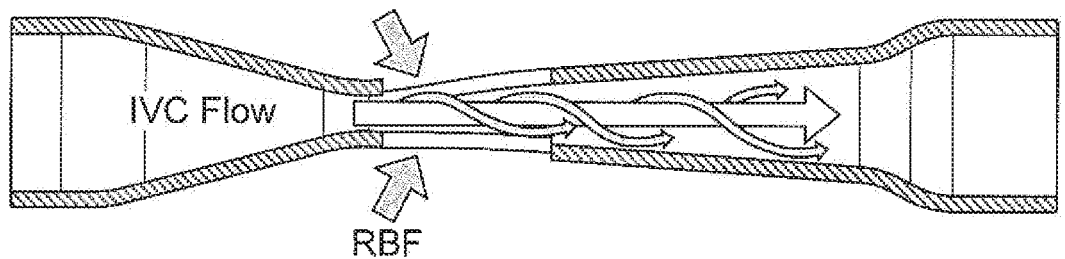

Referring now to FIGS. 53A-53B, openings 226 may be angled relative to the longitudinal axis of flow modulator 10, with the spiral-shaped, or helical, openings inducing a swirling flow pattern of the RBF in the diffuser, thereby creating greater flow stability with less flow disturbance.

Figure 54A:
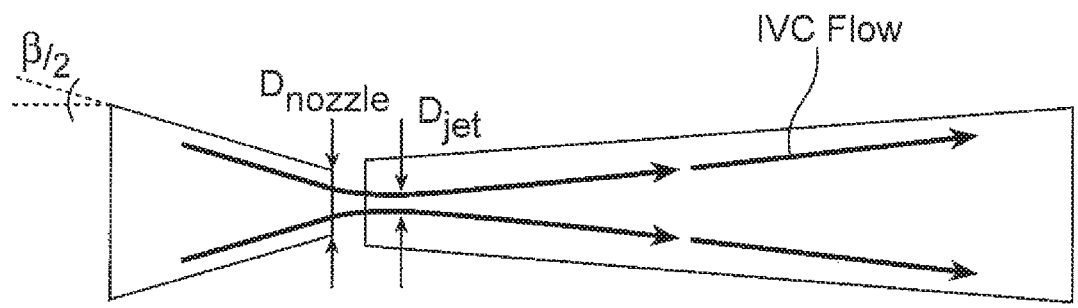
FIGS. 54A-54C are schematic views of a flow modulator manipulator the flow pattern, in accordance with another embodiment of the present invention.
Figure 54B:
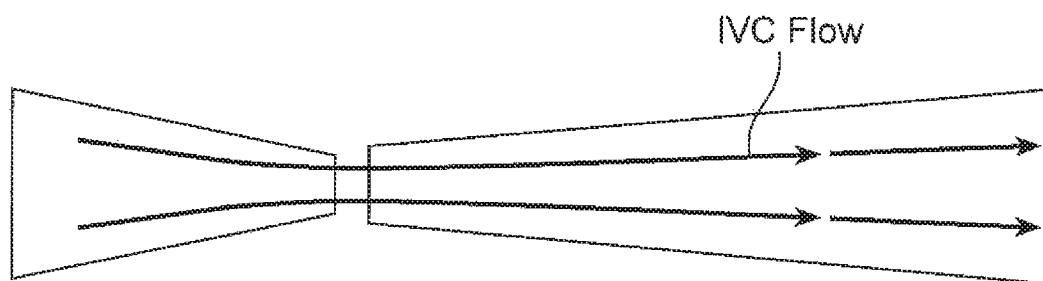
Figure 54C:
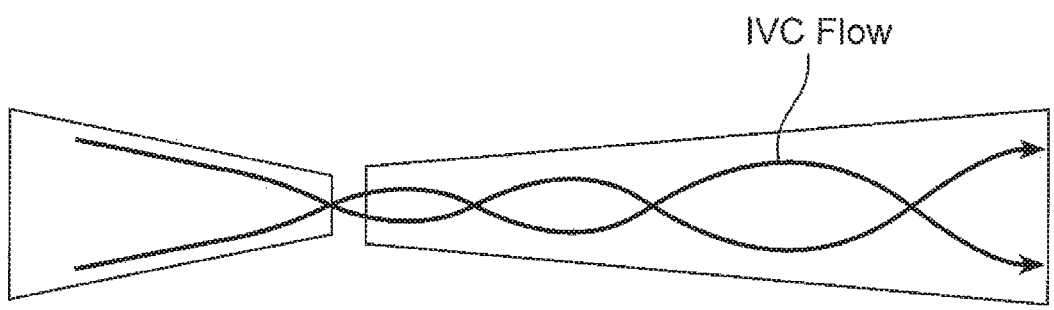

FIGS. 54A-54C depict manipulation of the IVC jet flow pattern by converging angle β/2, which is expected to improve efficiency of the diffuser and improve entrainment of the RBF. For example, in FIG. 54A, converging angle β/2 creates an effect called "vena contracta," in which the smallest diameter of the jet $D_{jet}$ is smaller than the diameter of the nozzle $D_{nozzle}$, and thus achieves faster divergence of the IVC jet flow. In contrast, a sharper converging angle can be used to achieve a more streamlined and stable IVC jet flow, as shown in FIG. 54B. In FIG. 54C, the IVC jet flow is manipulated to induce a swirling flow (circumferential velocity component), which may be achieved, for example, by adding small fins to the luminal side of the device.

Figure 55A:
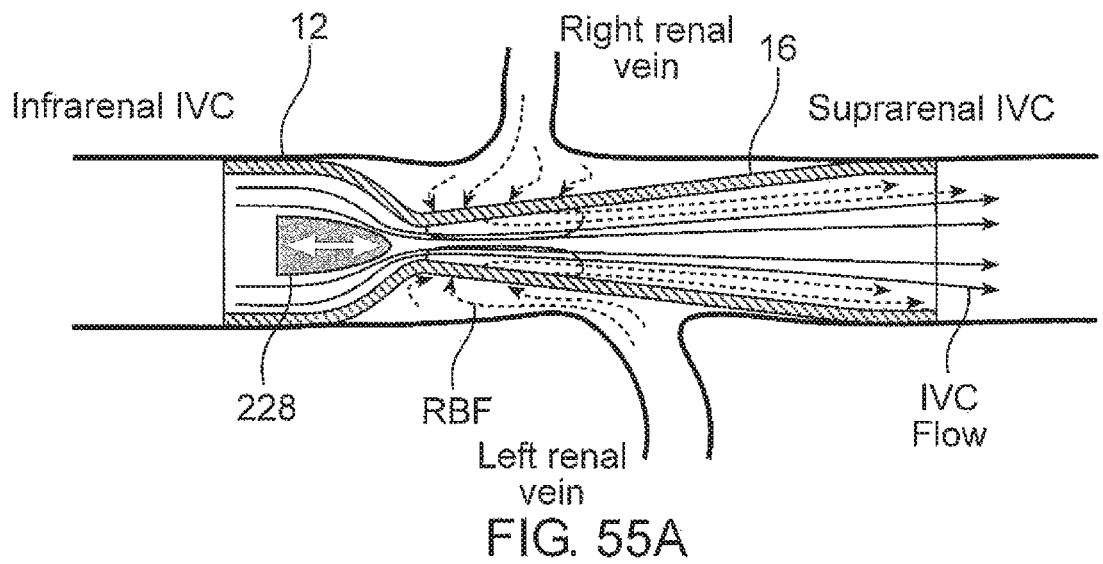
FIGS. 55A-55C are schematic views of an inner core inserted into a flow modulator, in accordance with another embodiment of the present invention.
Figure 55B:
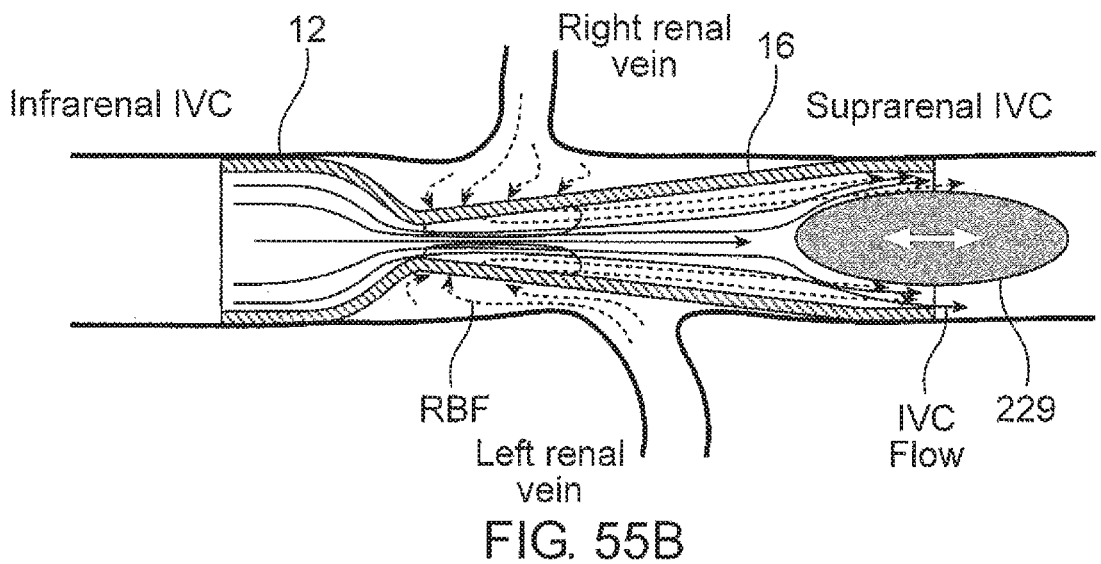
Figure 55C:
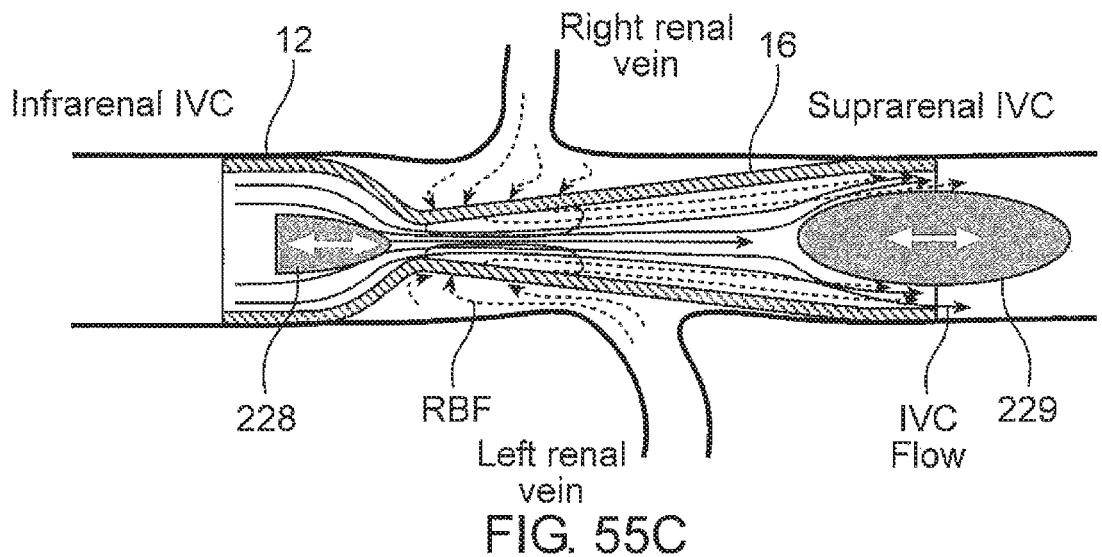

Referring now to FIGS. 55A-55C, a further alternative embodiment of a flow modulator is described in which inner cores 228, 229 are inserted into flow modulator 10. In FIG. 55A inner core 228, when positioned upstream to the nozzle in upstream component 12, can adjust the effective nozzle size. Thus, inner cores 228, 229 may act as plugs that fluid flows around. Inner core 228 thus may be used to maximize device efficacy. For example, advancing inner core 228 downstream toward the nozzle reduces the cross sectional area of the nozzle, achieves stronger reduction of fluid pressure in the nozzle region, and creates better suction (i.e. when IVC flow is relatively low and more suction pressure is needed). Moving inner core 228 upstream, away from the nozzle, increases the effective nozzle size and reduces suction pressure in the nozzle. However, when the starting position of inner core 228 is too far upstream, there will be little to no effect on the flow, and when inner core 228 is moved too close to the nozzle, it may reduce the IVC flow rate, thereby reducing device efficacy. For acute applications, inner core 228 may be disposed on the tip of an in-dwelling catheter (not shown), so that the axial location of inner core 228 may be manipulated by advancing or retracting the catheter tip. For chronic applications, inner core 228 may be suspended in upstream component 12 using a stent-like support that engages the inner surface of the upstream component and includes arms that extend radially inward to engage and support the inner core.

Alternatively, in FIG. 55B, inner core 229, similar in design to inner core 228 (with the cone-shaped tip facing upstream) may be disposed in the distal end of downstream component 16 to manipulate the effective angle α/2 of the diffuser, thus enhancing the IVC and RBF flows. Inner cores 228, 229 also may be disposed simultaneously in both upstream component 12 and downstream component 16, as shown in FIG. 55C. The adjustability of inner cores 228, 229 allows flow modulator 10 to be used compatibly with all patients, regardless of their flow rates, and may be advantageous for both acute and chronic applications.

Figure 56A:
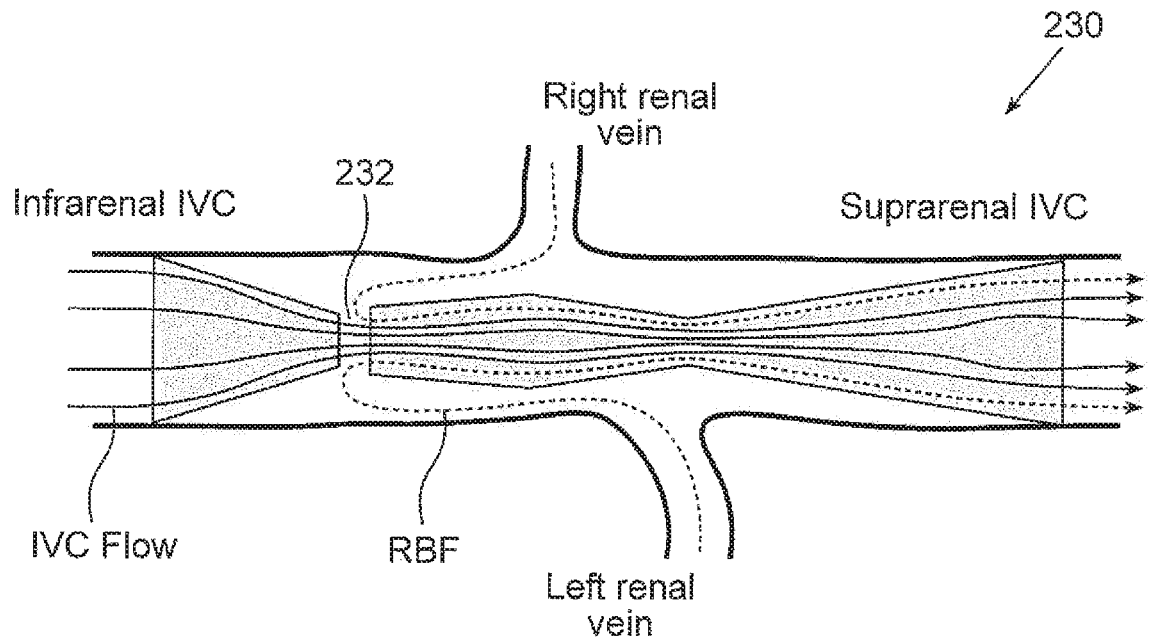
FIGS. 56A-56B are schematic views of a multi-stage flow modulator, in accordance with another embodiment of the present invention.
Figure 56B:
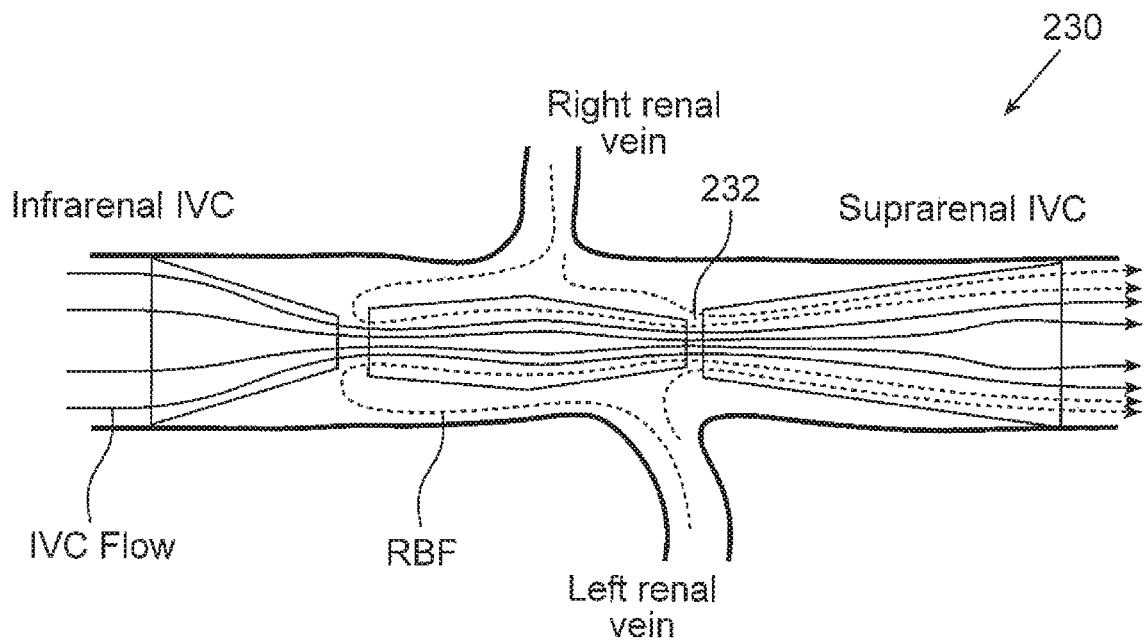

Referring now to FIGS. 56A and 56B, multi-stage flow modulator 230 is depicted with an intermediate nozzle and diffusion section disposed between the upstream component and downstream components of the inventive flow modulator. By employing two or more eductors in tandem in multi-stage flow modulator 230, a converging-diverging flow pattern may be obtained. As depicted in FIG. 56A, modulator 230 includes single gap 232 by which RBF is entrained, although multiple gaps for the RBF may be provided, as shown in FIG. 56B. For instance, gap 232 alternatively may be disposed between the upstream diverging-converging components and/or between the downstream converging-diverging components to achieve desired rates of suction and flow.

Referring now to FIGS. 57A-57C, inner core 234, e.g. balloon, is shown deployed in the IVC lumen at the level of the renal veins in accordance with aspect of the present invention. Inner core 234 may be a compliant, non-compliant, or rigid body. Inner core 234 reduces the cross-sectional area of the IVC, accelerates flow between inner core 234 and the IVC wall, and decreases local fluid pressure. Consequently, the driving pressure to entrain RBF is increased. Inner core 234 advantageously is both simple in design and its shape may be varied in the downstream direction to tailor flow. For instance, inner core 234 may be longer with a trailing edge reaching the region of the Hepatic veins without blocking the flow of other veins that merge into the IVC. Additionally, the diameter of inner core 234 may be changed, thus easily adjust the cross sectional area, and in turn altering pressure and improving performance.

As shown in FIG. 57A, inner core 234 may have an upstream region and a downstream region. The upstream region has a first end, e.g., the most upstream point of inner core 234, and a cross-sectional area that increases from the first end towards the downstream region such that the upstream region of inner core 234 diverges along the direction of IVC flow. The downstream region has a second end, e.g., the most downstream point of inner core 234, and a cross-sectional area that decreases from the upstream region toward the second end such that the downstream region of inner core 234 converges along the direction of IVC flow. In addition, inner core 234 may be symmetric about a longitudinal plane extending along the longitudinal axis of inner core 234. The thickness or diameter of inner core 234 may continuously change from the first end to the second end along the longitudinal axis of inner core 234, having a maximum cross-sectional area at the junction between the upstream region and the downstream region.

As the fluid stream passing around inner core 234 within the blood vessel will have a maximum speed at the maximum cross-sectional area of inner core 234, this will also be the region of inner core 234 having maximum friction. Thus, the constantly changing thickness or diameter of inner core 234 in the direction of fluid flow provides more effective fluid flow modulation while reducing pressure loss and not reducing IVC flow. In contrast, a constant-thickness or constant-diameter portion of inner core 234 would significantly increase pressure loss and cause a reduction in the IVC flow that would result in a smaller maximal flow rate and an overall less efficient flow modulator. Preferably, inner core 234 has no constant-thickness or constant-diameter portion, or alternatively, inner core 234 has at most 15 mm of constant-thickness or constant-diameter.

As shown in FIG. 57A, the cross-sectional area of the upstream region may increase at a larger rate than the rate of decrease of the cross-sectional area of the downstream region, which permits inner core 234 to accelerate the fluid stream passing around the upstream region towards the downstream region between inner core 234 and the branch lumen, e.g., where the right renal vein and the left renal vein intersects the IVC. As shown in FIG. 57A, the maximum cross-sectional area of inner core 234 may be positioned upstream of the branch lumen. Accordingly, the angled-converging downstream portion of inner core 234 extends throughout the entire branch lumen portion of the blood vessel. This permits more renal blood to be entrained into the IVC as the effective lumen area between inner core 234 and the inner wall of the blood vessel increases in proximity to the renal vein ostium and allows extra lumen area for the renal vein flow to join into the IVC branch without competing with the IVC flow. Accordingly, the renal veins are still exposed to reduced flow at their outlet, yet with minimal interference between the two merging flows. In contrast, a constant-thickness or constant-diameter portion of inner core 234 having a maximum cross-sectional area throughout would provide a small effective lumen area for the renal flow to join the IVC flow, and the renal flow and the IVC flow would compete on the same narrowed lumen.

Inner core 234 may block blood flow within the vessel lumen such that blood cannot flow through inner core 234, thereby forcing blood to flow only around inner core 234. Inner core 234 may be completely suspended within the vessel lumen without contacting any portion of the inner wall of the vessel. In addition, as shown in FIG. 57A, the downstream region of inner core 234 may include a first converging region and a second converging region downstream of the first converging region. The first converging region has a cross-sectional area that decreases from the upstream region of inner core 234 to the second diverging region of the downstream region of inner core 234 at a slower rate than the cross-sectional area of the second diverging region of the downstream region of inner core 234.

FIG. 57B is a front view of inner core 234 disposed in the IVC lumen, which permits flow around the entire circumference of the device. Alternative inner core 235 configuration, depicted in FIG. 57C, contacts the IVC wall along most of its circumference, and instead leaves channels adjacent to the renal vein outlets, thereby concentrating the IVC flow adjacent to the renal vein ostia. Such shapes may be created using a non-axisymmetric stent in which a low pressure balloon is deployed, or multi-compartment balloon.

In FIGS. 58A-58F, structures for deploying inner core 234 of FIG. 57A-57C within the IVC are described. Inner core 234 may be disposed within stent 236, which may be deployed within the IVC in a chronic or acute application. Stent 236 centers device 234 in the IVC lumen, and may reduce risk of the IVC wall from collapsing due to the decrease in pressure. Stent 236 also may be used to support the IVC from narrowing due to the suction pressure induced by the flow modulation. In addition, stent 236 may be used to selectively increase or decrease the vessel diameter to thereby determine the needed increase in flow. Stent 236 may have a tapered geometry that enables inner core 234 to be secured at different points along the contour of inner core 234. Stent 236 may allow better control over the space between the vessel wall and inner core 234. This control may be beneficial for pre-defining the device performance Stent 236 further may be used to provide a precise predetermined distance between inner core 234 and the inner wall of the blood vessel. As the inner wall of the IVC is not perfectly circular and does not have a constant area, a rigid stent may provide a control surface area.

Figure 58A:
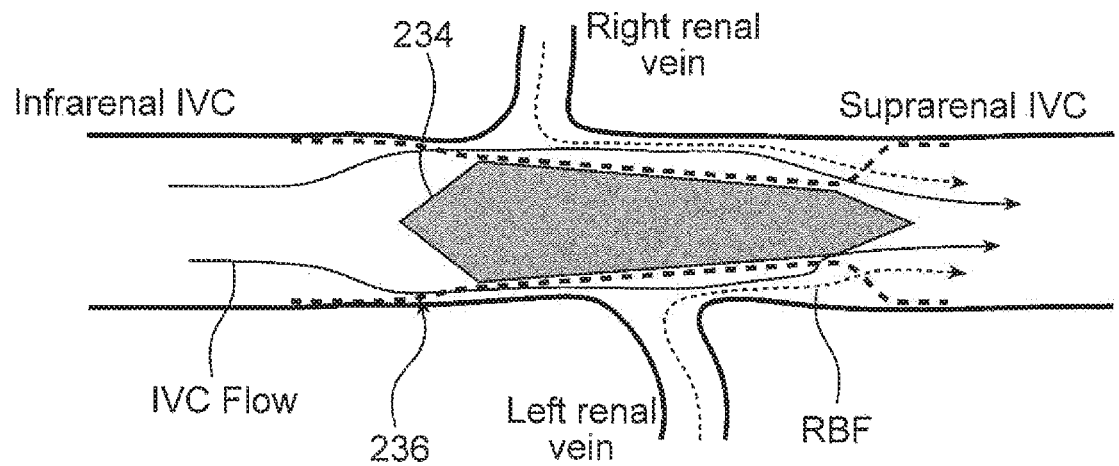
FIGS. 58A-58F are schematic views of an inner core inserted into a flow modulator used with a stent, in accordance with a still further embodiment of the present invention.
Figure 58B:
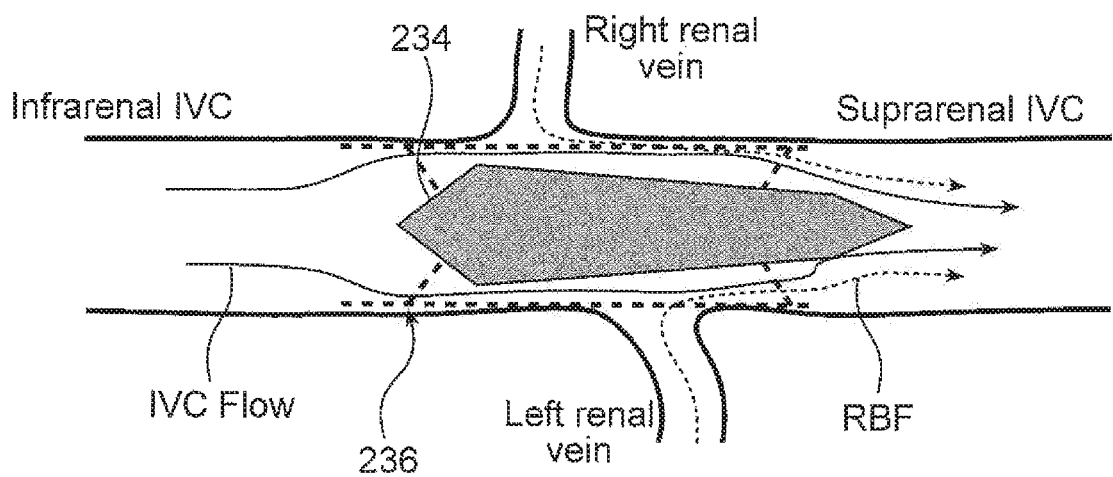
Figure 58C:
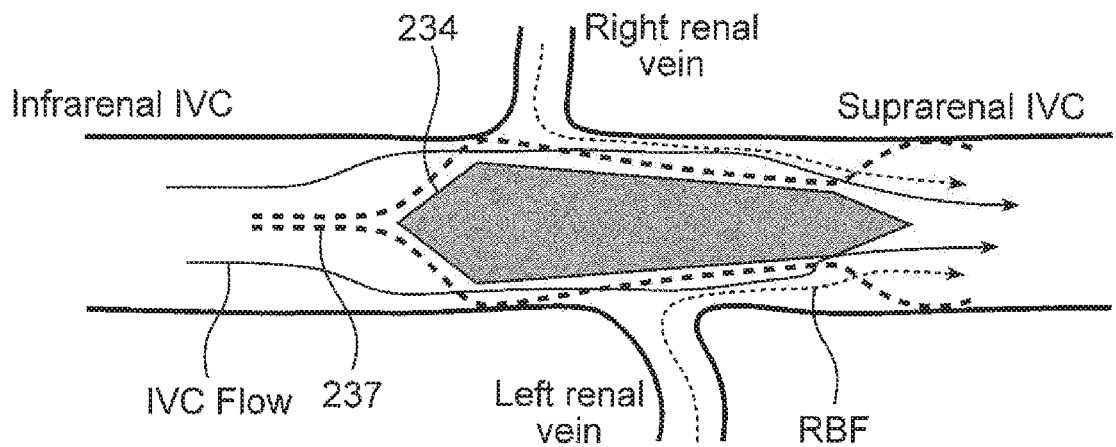
Figure 58D:
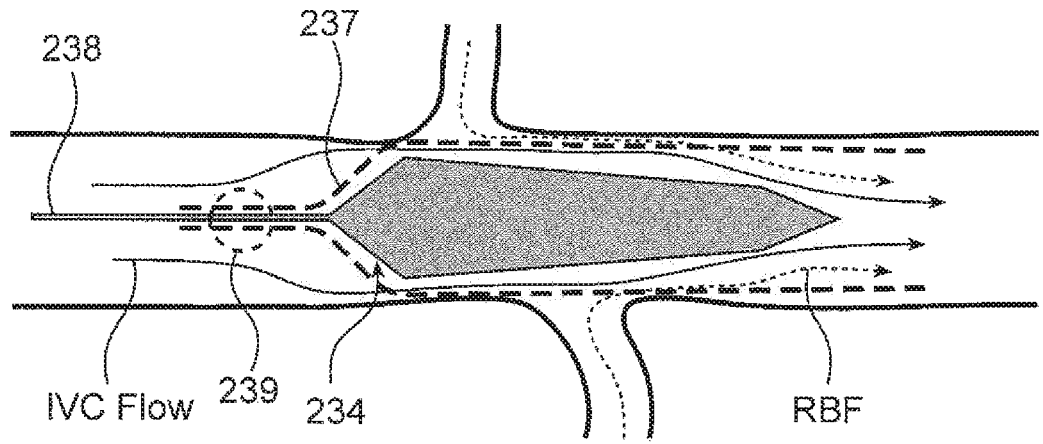
Figure 58E:
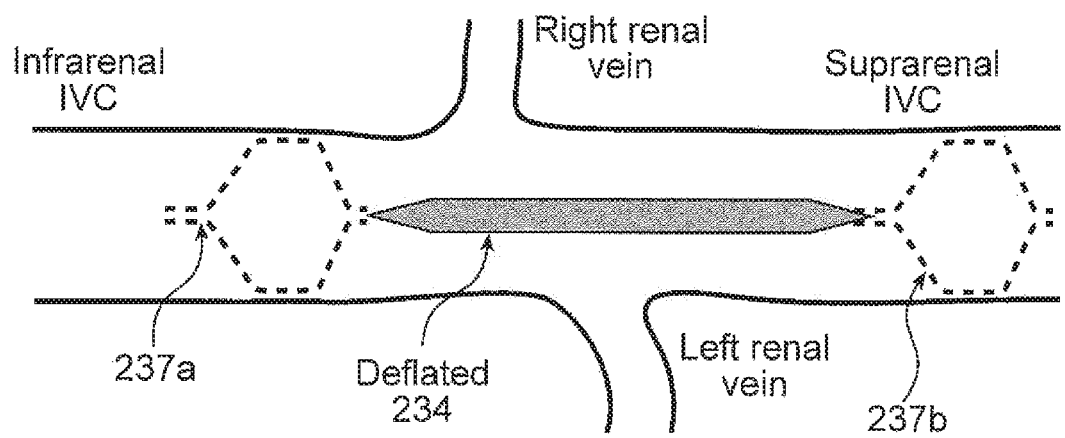
Figure 58F:
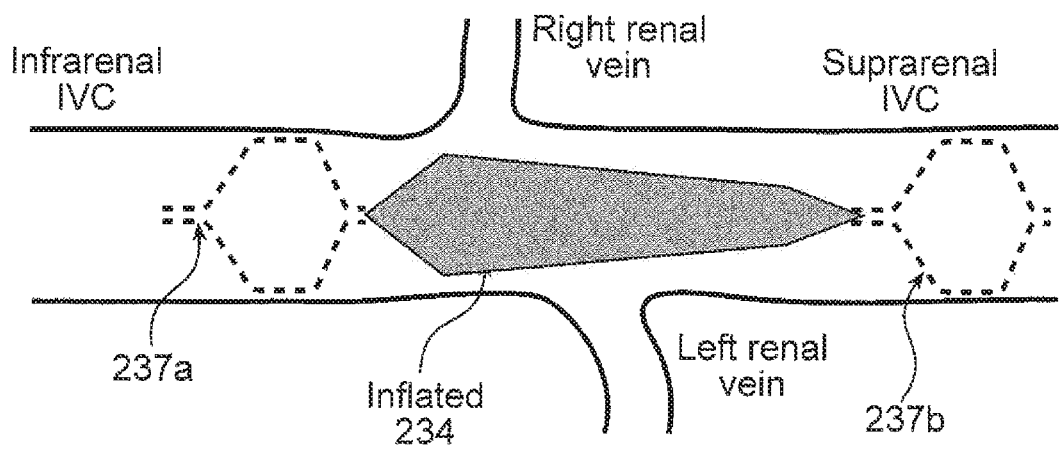

In FIG. 58C, an alternative embodiment of stent 237 is described, in which stent 237 may be a recapturable stent pre-deployed with inner core 234 inflated into it at a later stage to achieve the lumen profile. In FIG. 58D, an alternative embodiment suitable for acute applications is described, in which stent 237 may be coupled to an in-dwelling guide wire 238 at end 239 to secure stent 237 and inner core 234 within the vessel. Stent 236 may be deployed as a single unit or stent 236 may be deployed in the IVC vessel and inner core 234 may be introduced in a later stage. Further, as shown in FIGS. 58E and 58F, more than one stent 237a, 237b may be located proximal to and distal to inner core 234, and positioned as a single unit in the vessel. Once positioned, inner core 234 may be inflated.

Figure 59A:
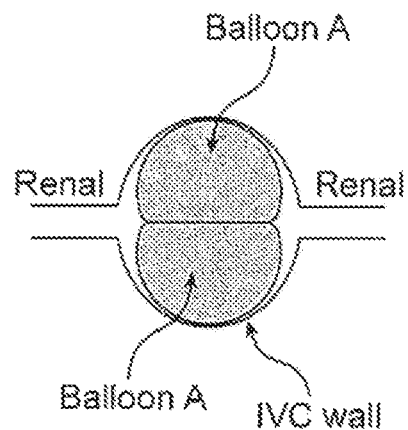
FIGS. 59A-59B are schematic views of more than one inner core inserted into a flow modulator, in accordance with another embodiment of the present invention.
Figure 59B:
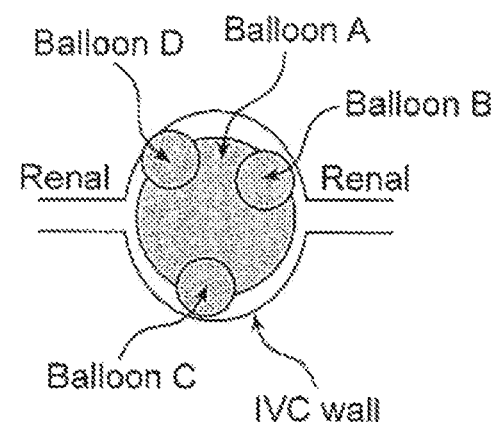

In FIGS. 59A-59B, other alternative designs for securing inner core 234 within the IVC are described. For instance, inner core 234 may be formed from two balloons of approximately equal volume which contact each other in the center region of the vessel, thereby securely positioning the device within the IVC while enabling IVC flow and enhanced renal flow. In FIG. 59A, a cross sectional view of the two balloons Balloon A, Balloon B are depicted each forming a semicircle shape as they make contact in the flattened region, creating a gap for blood flow. In FIG. 59B, inner core 234 includes primary Balloon A and is secured within the IVC by securement Balloons B, C and D. Some of the balloons, for example, may be more compliant than others, therefore conforming to the shape of the IVC more than the less compliant balloons.

Figure 60A:
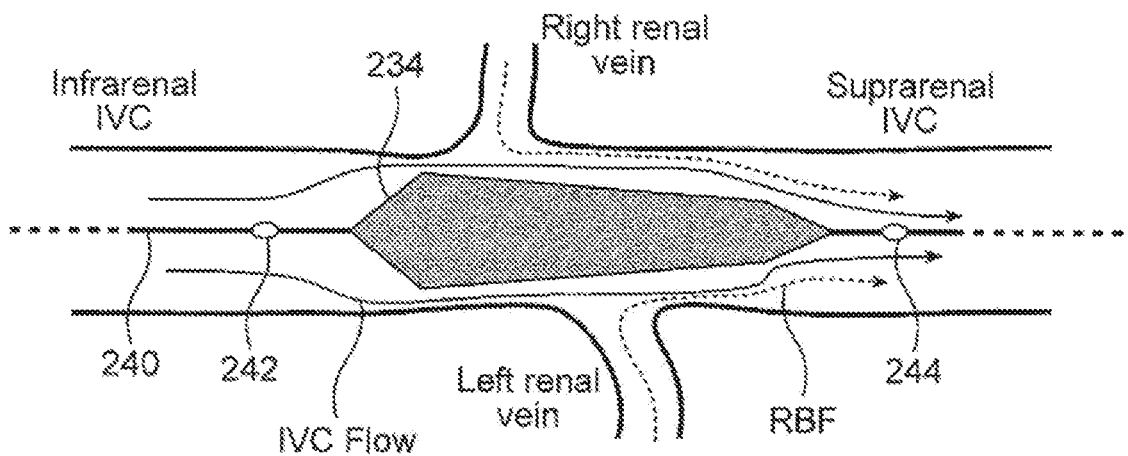
FIG. 60A is a schematic view of an inner core inserted into a flow modulator used with pressure transducers, in accordance with a further embodiment of the present invention.
Figure 60B:
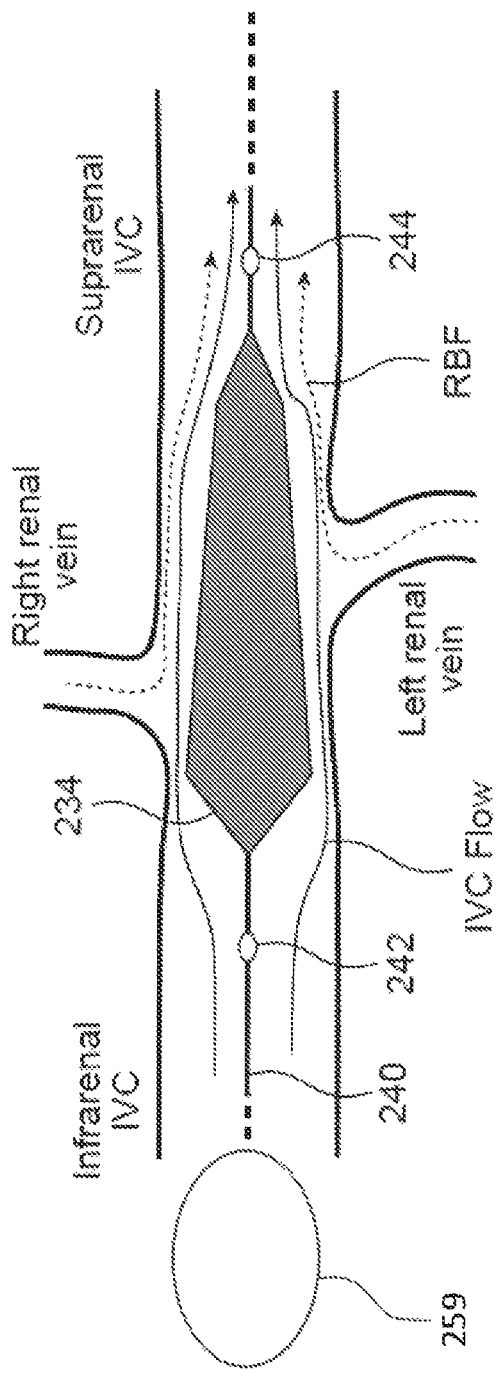
FIG. 60B is a schematic view of an inner core inserted into a flow modulator used with pressure transducers, in accordance with another embodiment of the present invention; having an upstream balloon.

Referring now to FIG. 60A, a further alternative embodiment of a flow modulator of the present invention is described, in which the flow modulator is coupled to guide wire 240 and includes pressure transducers that are disposed on either side of the flow modulator. Guide wire 240, which alternatively may be a multi-lumen catheter, includes two pressure transducers 242, 244, which may be local diaphragm-based sensors, connected via the multi-lumen catheter to sensors at the proximal end of the device, or optical pressure sensor. Alternatively, a single differential pressure transducer may be used that provides a reading of the pressure differential across the two sensor sites. The size of inner core 234 may be adjusted to tailor the performance of the flow characteristics within the vessel, based upon feedback from pressure transducers 242, 244, X-ray angiography, or other readings. The size of inner core 234 may also be adjusted without the use of a pressure transducer. As shown in FIG. 60B, balloon 259 may be coupled to catheter 240, e.g., a multi-lumen catheter having an inflation/deflation lumen(s), upstream of the flow modulator so as to increase the IVC resistance, while not increasing resistance to flow from the kidneys. Accordingly, balloon 259 may be selectively inflated/deflated via inflation/deflation lumen(s) to achieve the desired IVC resistance and/or inner core 234 may be selectively inflated/deflated via inflation/deflation lumen(s). Alternatively, balloon 259 may be coupled to catheter 240 downstream of the flow modulator.

Referring to FIGS. 61A-61B, a self-adjusting flexible nozzle is described in accordance with another aspect of the present invention. In particular, the nozzle may include flexible membrane 246, such as a stent coated with a polymer, Dacron, or other elastic coating. Flexible membrane 246 in the nozzle region may not follow the contour of stent 236, and may instead penetrate into the nozzle lumen, creating free surface 248. Free surface 248 provides a self-adjusting nozzle, such that the cross-sectional area of the nozzle may expand responsive to the IVC flow, as depicted in FIG. 61B. By contrast, when the IVC flow is relatively low, expansion of free surface 248 will be reduced, resulting in a smaller nozzle cross-section. In general, when infrarenal IVC flow is relatively low, a smaller size nozzle is required to create a sufficient jet and local decrease in pressure. When the IVC flow is relatively high (e.g. during exercise), a larger size nozzle is provided to create high renal suction. Moreover, high IVC flow through a relatively small nozzle may create too high of a pressure drop across the eductor, which could result in significant increase of upstream pressure, or significant decrease of pressure downstream of the eductor.

Free surface 248 may include slits that create small flaps. Such flaps are expected to respond to IVC flow, bending outwards when the IVC flow is relatively high and returning inwards when the IVC flow is relatively low. The flaps may be long enough to form a valve, such that, at theoretically zero IVC flow the flaps close the nozzle completely.

With respect to FIGS. 62A-62B, the effect of flow modulator on RBF is described. Generally, flow modulator 10 may be positioned either upstream or downstream. In either configuration, inlet sealing zone 250 and outlet sealing zone 252 are formed. Deploying flow modulator 10 downstream may create inlet sealing zone 250 just before the ostia of the renal veins. By contrast, deploying the eductor upstream creates outlet sealing zone 252, immediately downstream of the renal vein ostia, thereby achieving better wash-out of blood in the cavity that is formed between flow modulator 10 and the IVC. In this latter configuration, the RBF flows along the exterior of the diffuser before it enters into opening 226 and merges with the IVC flow. Benefit also may be gained from deployment of a longer flow modulator, in which the IVC section between the Common Iliac veins and the renal veins may be exploited due to the absence of other major veins. In addition, flow modulator 10 may be designed such that most of its length is the diffuser, ensuring that flow of other veins that merge into the IVC is not blocked. Only inlet and outlet sealing zones 250, 252, which are relatively short, may block flow of merging veins.

Figure 63:
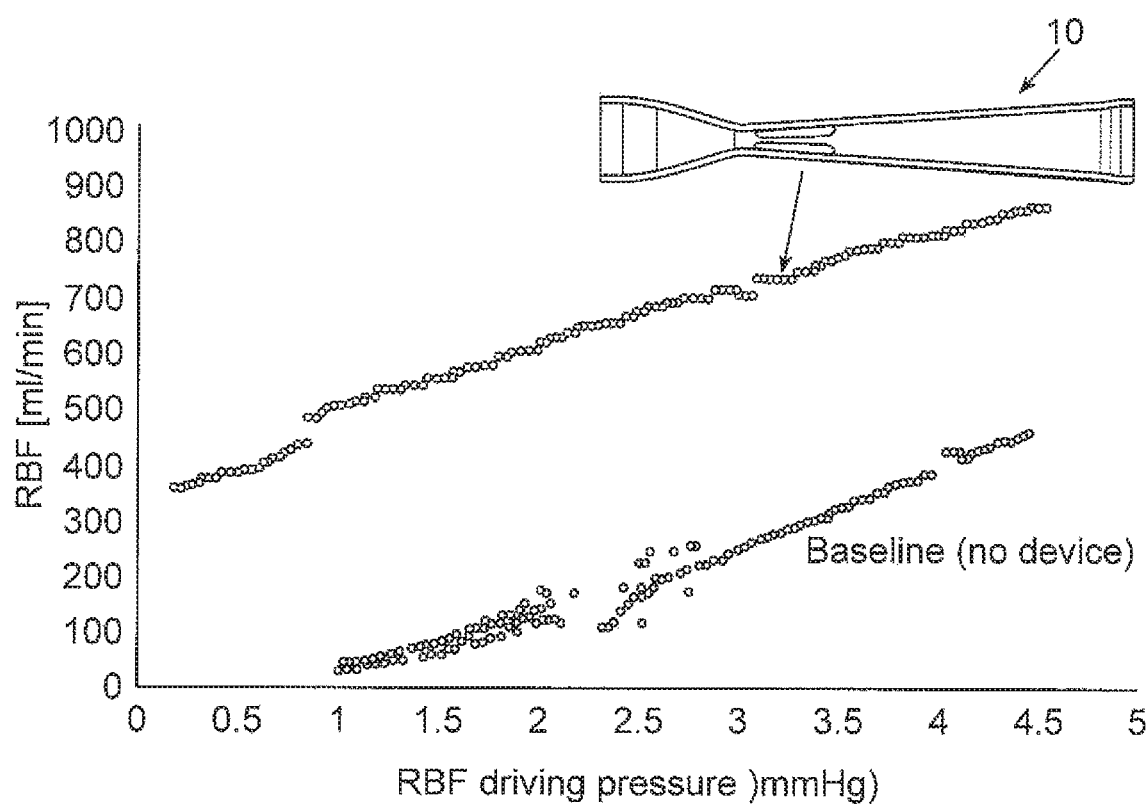
FIG. 63 is a graph of in-vitro results of improvements in simulated RBF using a flow modulator, in accordance with another embodiment of the present invention.

Referring to FIG. 63, a graph of in-vitro results of improvements in simulated RBF using flow modulator 10 of the present invention is described. In this experiment, flow modulator 10 was placed within a mock silicone IVC model that included renal veins. The IVC flow was set to varying flow rate levels. The working fluid was blood analog solution at 37° C., with viscosity of 3.7 cP. For the results shown in FIG. 63, an IVC flow rate of 2 L/min was used. The flow rate exiting the renal veins was measured over a varying range of driving pressures. FIG. 63 shows RBF measured with a flow modulator placed in the mock IVC, compared to a similar experiment without a flow modulator. For example, for an RBF of a patient of 75 ml/min (for driving pressure of 15 mmHg), use of the inventive flow modulator increases RBF to about 550 ml/min, which is 7.3 times bigger.

By adjusting the nozzle size, the device of the present invention can provide a wide range of infrarenal IVC flow rates, for example 0.5 L/min (low rest) to 6.0 L/min. For acute decompensated heart failure patients, the infrarenal IVC flow rate is typically in the 0.5-3.0 L/min range. A ratio range of infrarenal IVC flow rate to the flow modulator nozzle diameter $D_{nozzle}$ is defined as: 0.1-0.75 [L/(min*mm)] This range of ratios covers the combinations of physiological IVC flow rates and nozzle diameters in which the RBF could be practically improved, without significantly increasing the venous pressure. For example, a nozzle size of 5.0 mm and infrarenal IVC flow of 2.0 L/min yields a ratio of 0.4.

Figure 64A:
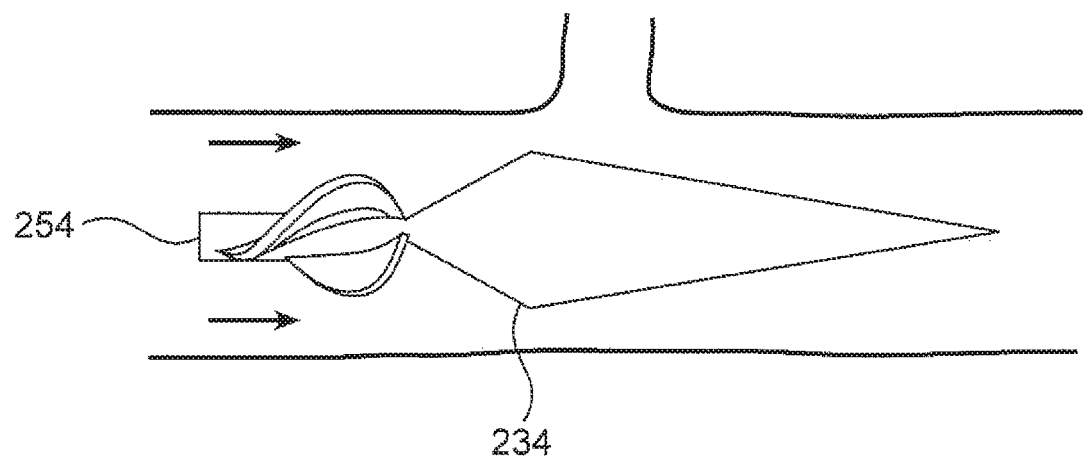
FIGS. 64A-64B are schematic views of an inner core inserted into a flow modulator used with a pump, in accordance with another embodiment of the present invention, coupled downstream and upstream, respectively.
Figure 64B:
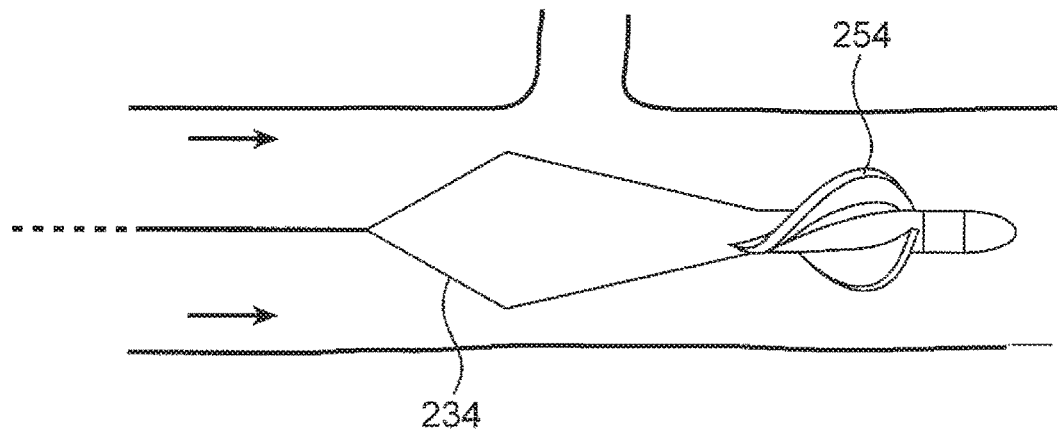
Figure 64C:
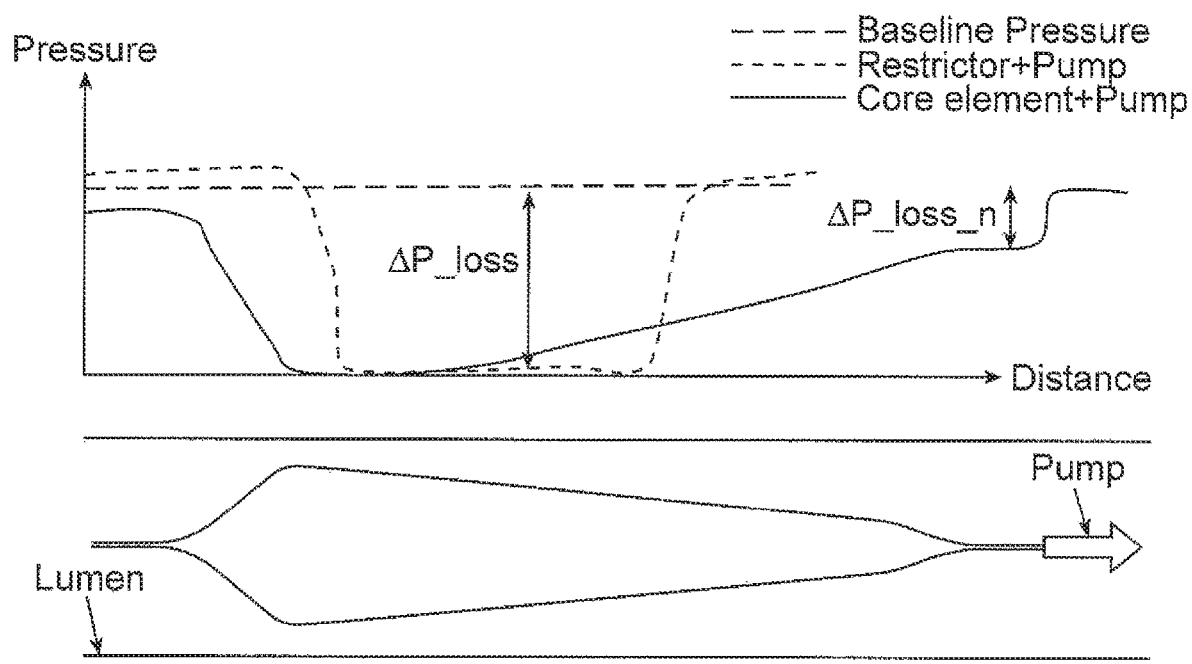
FIG. 64C is a graph of pressure loss results using a flow modulator as described in FIGS. 64A and 64B, in accordance with another embodiment of the present invention.

Referring to FIGS. 64A-64C, an inner core used in conjunction with a pump is described. Any of the designs for flow modulator 10 and/or inner core 234 described herein may be coupled to pump 254. Pump 254 may be any pump that is used to increase flow and/or pressure in a blood vessel and/or the heart. As shown in FIGS. 64A and 64B, pump 254 may be coupled either upstream or downstream to inner core 234. This configuration results in smaller pressure loss, as compared to a known method of using a restrictor and a pump, or two pumps working against each other, to reduce pressure in the renal veins area or in the thoracic duct drainage area (or any other lymph drainage area). There are several advantages of the smaller pressure loss. For instance, a smaller pump is needed and a smaller crimping profile can be achieved. For a similar sized pump, less RPM is required, thus decreasing thrombogenicity. Further, for a chronic application with a battery, a smaller battery can be used. An external source may also be used to increase IVC flow. For instance, devices which mimic the natural action of the ambulatory calf and/or foot pump, that are routinely used to reduce the risk of deep vein thrombosis by increasing peripheral blood flow, may be used as a power source with any of the designs described herein.

In accordance with another aspect of the present invention, pump 254, e.g., an impeller, may be positioned adjacent the maximal cross-sectional area of inner core 234, or extend across the entire length of inner core 234. Pump 254 may rotate together with inner core 234. Preferably, pump 254 rotates independently from inner core 234. Pump 254 may be partially rigid, while inner core 234 is an inflatable balloon as described above when no motor is necessary. Alternatively, both inner core 234 and pump 254 may both be expandable and crimped to the catheter. As described above, a stent may be positioned between inner core 234 and the inner wall of the blood vessel, thereby preventing vessel damage by pump 254.

The graph in FIG. 64C illustrates the pressure loss difference between a baseline, the Restrictor+Pump design, and the Inner Core+Pump configuration described herein. In this schematic, the flow rate is identical in each scenario and the pressure upstream is constant. The baseline represents a constant pressure in the vessel. The Restrictor+Pump line indicates a reduction in pressure due to resistance, and a pump downstream to increase pressure and maintain a constant flow rate. The pressure loss is represented by ΔP_loss. When inner core 234 is used with pump 254, the flow accelerates and pressure reduces as the cross-section of the flow area gets smaller, but the pressure slow recovers as the cross-section of the flow area increases. Pump 234 then increases the pressure back to the baseline pressure. This pressure loss is represented by ΔP_loss_n.

Figure 65:
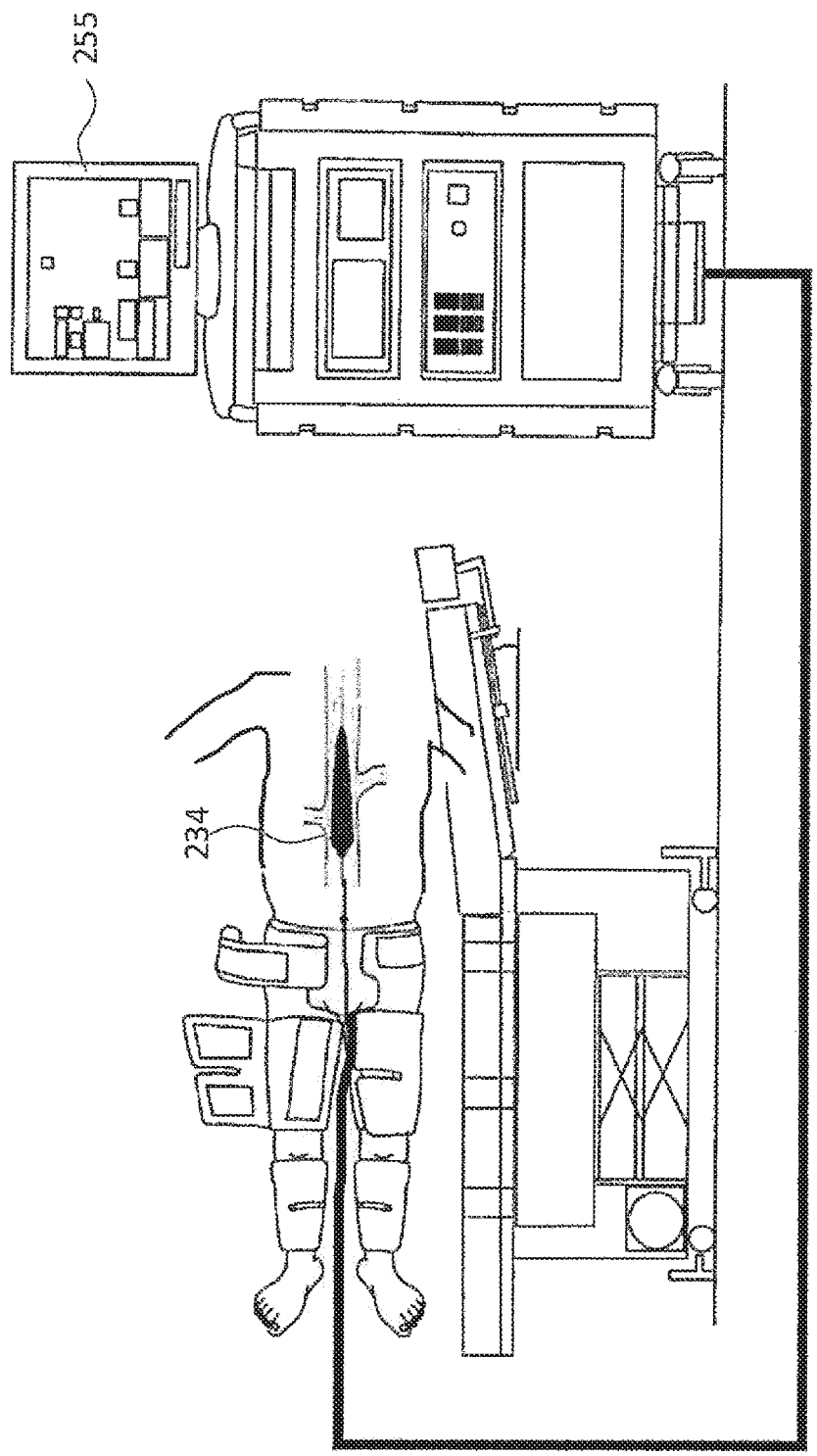
FIG. 65 illustrates a system including the flow modulator having an external pump and control system.

Referring now to FIG. 65, an inner core used in conjunction with an external pump and control system is described. Any of the designs for flow modulator 10 and/or inner core 234 described herein may be coupled to pump 255. Pump 255 may be any pump that is used to increase flow and/or pressure in a blood vessel and/or the heart. For example, pump 255 may be an intermittent pneumatic compression (IPC) or a cardiac enhanced external counter-pulsation (EECP) pump (such as the ArtAssist® device, available by ACI Medical, San Marcos, California). Pump 255 may be programmed to mimic the natural pumping action of an ambulatory calf and/or foot to move blood in the deep veins of the leg, thereby reducing deep vein thrombosis formation. In addition, pump 255 may provide power to the flow modulator.

Figure 66:
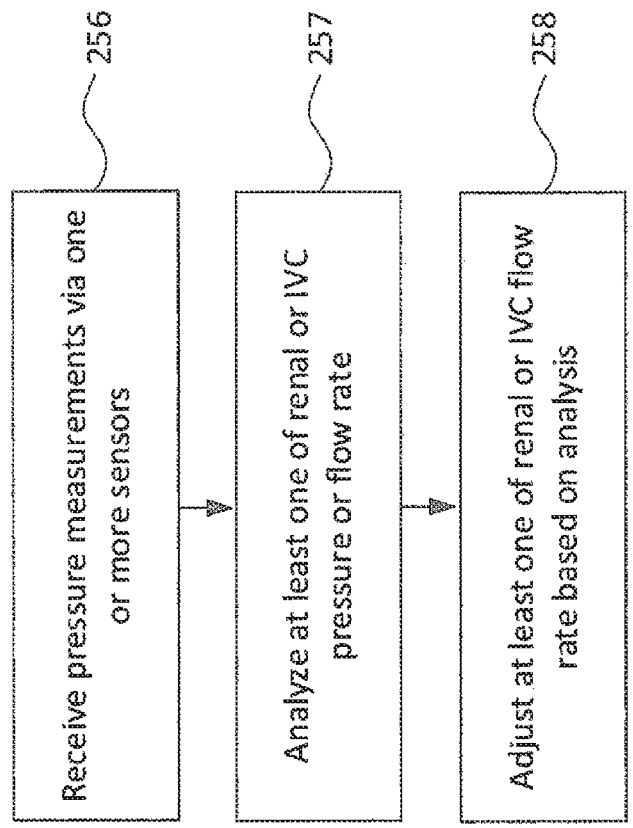
FIG. 66 is a flow chart illustrating the steps of adjusting the parameters of a flow modulator pump system.

Referring now to FIG. 66, method steps for adjusting the parameters of a flow modulator pump system are provided. For example, a control system having a user interface may be used with pump 255 and flow modulator 10 and/or inner core 234 to adjust flow through/across flow modulator 10 and/or inner core 234. At step 256, the control system may receive pressure measurements from the patient from, e.g., pressure sensors P1, P2, P3 described above, and/or renal/IVC flow rates, and/or routinely used pressure ports, e.g., a central line and/or a femoral vein sheath or port. At step 257, the control system analyzes renal and/or IVC pressure and/or flow rates based on the measurements received. For example, the measurements may be compared to parameters and threshold values stored within memory of the control system. Then, at step 257, based on the analysis from step 257, the control system adjusts flow rate or suction pressure of flow modulator 10 and/or inner core 234. For example, the control system may adjust the amplitude and/or frequency of pump 255 and/or inflate/deflate any one of inner core 234 or balloon 259 (if used) until a desired flow rate or suction pressure is achieved. As will be understood by a person having ordinary skill in the art, the control system may work with any of the designs for flow modulator 10 and/or inner core 234 and/or pumps 254 and 255 described herein.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A device for altering fluid flow through a body lumen, the body lumen coupled to a branch lumen, the device comprising:
    a flow modulator configured to be positioned within the body lumen, the flow modulator comprising an upstream component, a downstream component, and an entrainment region, the upstream component having an inlet, an outlet, and a cross-sectional flow area that converges from the inlet towards the outlet, the downstream component having an entry, an exit, and a cross-sectional flow area that diverges from the entry towards the exit, and the entrainment region comprising a diverging portion and a plurality of longitudinally extending openings radially spaced around the diverging portion of the entrainment region, the entrainment region between the inlet of the upstream component and the exit of the downstream component,
    wherein the flow modulator is configured to accelerate a fluid stream passing through the upstream component towards the downstream component to generate a low pressure region in the vicinity of the entrainment region that entrains additional fluid into the fluid stream via the plurality of longitudinally extending openings as the fluid stream passes into the entry of the downstream component.

2. The device of claim 1, wherein the entrainment region diverges at a same angle as at least a portion of the downstream component's divergence angle.

3. The device of claim 1, wherein the entrainment region is integrally formed with the downstream component.

4. The device of claim 1, wherein the entry of the downstream component has a diameter larger than a diameter of the outlet of the upstream component.

5. The device of claim 1, further comprising an inner core advanced into at least one of either the upstream component or the downstream component.

6. The device of claim 1, wherein the upstream component defines a first plurality of cells and the downstream component defines a second plurality of cells having a less flexible structure than the first plurality of cells.

7. The device of claim 6, wherein the downstream component comprises a first diverging portion and a second diverging portion, the first diverging portion upstream from the second diverging portion, and wherein the second diverging portion defines a third plurality of cells, wherein the first and third plurality of cells' average void space areas are greater than the second plurality of cells' average void space area.

8. The device of claim 7, wherein the second plurality of cells is disposed between the first and third pluralities of cells.

9. The device of claim 7, wherein the first plurality of cells' average void space area and third plurality of cells' average void space area are identical.

10. The device of claim 1, wherein the downstream component comprises a first diverging portion and a second diverging portion, the first diverging portion upstream from the second diverging portion, wherein the second diverging portion's average angle of divergence is greater than the first diverging portion's average angle of divergence.

11. The device of claim 1, wherein the upstream portion further comprises a constricted section at an upstream end configured to permit coupling to a delivery device.

12. The device of claim 11, wherein the constricted section is configured to remain coupled to the delivery device for an acute treatment.

13. The device of claim 1, wherein downstream component comprises an atraumatic end.

14. The device of claim 1, wherein the upstream component and the downstream component are at least partially coated with a biocompatible material, thereby exposing the plurality of longitudinally extending openings in the entrainment region.

15. The device of claim 7, wherein the first and third plurality of cells are more flexible than the second plurality of cells.

16. The device of claim 1, wherein the cross-sectional flow area at the outlet of the upstream component is less than the cross-sectional flow area at the entry of the downstream component.

17. The device of claim 1, wherein the upstream component, the downstream component, and the entrainment region comprise a single frame coated with one or more biocompatible materials.

18. The device of claim 1, wherein a length of the downstream component is greater than a length of the upstream component.

19. The device of claim 1, wherein an average angle of convergence of the upstream component is greater than an average angle of divergence of the downstream component.

20. The device of claim 1, wherein the upstream component comprises a nozzle that accelerates the fluid stream passing through the upstream component and the downstream component comprises a diffuser that decelerates the fluid stream having the entrained additional fluid passing through the downstream component.

21. A delivery device for delivering a flow modulator, the delivery device comprising:
 a sheath having a lumen sized to hold the flow modulator therewithin in a contracted, delivery state during delivery; and
 an inner assembly slidably disposed within the lumen of the sheath to facilitate deployment out a distal end of the sheath; and
 wherein the flow modulator is the flow modulator of claim 1.

22. A method for altering fluid flow through a body lumen, the body lumen coupled to a branch lumen, the method comprising:
 positioning a flow modulator within a body lumen, the flow modulator comprising an upstream component, a downstream component, and an entrainment region, the upstream component being positioned in a first body lumen portion and having an inlet, an outlet, and a cross-sectional flow area that converges from the inlet towards the outlet, the downstream component being positioned in a second body lumen portion and having an entry, an exit, and a cross-sectional flow area that diverges from the entry towards the exit, and the entrainment region being positioned in a third body lumen portion between the inlet of the upstream component and the exit of the downstream component, the entrainment region comprising a diverging portion and a plurality of longitudinally extending openings radially spaced around the diverging portion of the entrainment region; and
 accelerating a fluid stream passing through the upstream component towards the downstream component to generate a low pressure region in the vicinity of the entrainment region and to entrain additional fluid into the fluid stream via the plurality of longitudinally extending openings as the fluid stream passes into the entry of the downstream component.

23. The method of claim 22, wherein positioning the flow modulator within the body lumen comprises positioning the upstream component in an inferior vena cava such that the inlet is upstream from a branch off to a renal vein and the downstream component in the inferior vena cava such that the exit is downstream from the branch off to the renal vein, thereby drawing blood from the renal vein and improving kidney functionality.

24. The method of claim 23, wherein drawing the blood from the renal vein to improve kidney functionality further reduces excess fluid to treat heart failure.

25. The method of claim 22, wherein the the plurality of radially spaced longitudinally extending openings are angled relative to the longitudinal axis of the flow modulator, thereby creating a swirling fluid flow pattern.

26. The method of claim 22, wherein positioning the flow modulator within the body lumen comprises positioning the upstream component in an inferior vena cava such that the inlet is upstream from a branch off to a hepatic vein and the downstream component in the inferior vena cava such that the exit is downstream from the branch off to the hepatic vein, thereby drawing blood to the inferior vena cava and improving splanchnic circulation.

27. The method of claim 22, further comprising coupling a constricted section to a delivery device for an acute treatment.

28. The method of claim 22, further comprising advancing an inner core into the flow modulator to further entrain the fluid.

* * * * *